United States Patent
Simpson et al.

(10) Patent No.: US 10,253,107 B2
(45) Date of Patent: Apr. 9, 2019

(54) USE OF ENDOCYTOSIS INHIBITORS AND ANTIBODIES FOR CANCER THERAPY

(71) Applicant: THE UNIVERSITY OF QUEENSLAND, St. Lucia (AU)

(72) Inventors: Fiona Simpson, Paddington (AU); Nicholas Andrew Saunders, Holland Park (AU)

(73) Assignee: THE UNIVERSITY OF QUEENSLAND, St. Lucia (AU)

( * ) Notice: Subject to any disclaimer, the term of this patent is extended or adjusted under 35 U.S.C. 154(b) by 129 days.

(21) Appl. No.: 14/438,440

(22) PCT Filed: Oct. 28, 2013

(86) PCT No.: PCT/AU2013/001246
§ 371 (c)(1),
(2) Date: Apr. 24, 2015

(87) PCT Pub. No.: WO2014/063205
PCT Pub. Date: May 1, 2014

(65) Prior Publication Data
US 2015/0284469 A1    Oct. 8, 2015

(30) Foreign Application Priority Data
Oct. 26, 2012  (AU) .............................. 2012904722

(51) Int. Cl.
| | |
|---|---|
| *A61K 31/18* | (2006.01) |
| *A61K 31/166* | (2006.01) |
| *A61K 31/351* | (2006.01) |
| *A61K 31/505* | (2006.01) |
| *A61K 31/724* | (2006.01) |
| *A61K 31/4706* | (2006.01) |
| *A61K 31/5415* | (2006.01) |
| *A61K 39/00* | (2006.01) |
| *A61K 39/395* | (2006.01) |
| *A61K 45/06* | (2006.01) |
| *C07K 16/28* | (2006.01) |
| *C07K 16/30* | (2006.01) |
| *C07K 16/32* | (2006.01) |
| *G01N 33/574* | (2006.01) |

(52) U.S. Cl.
CPC ............ *C07K 16/32* (2013.01); *A61K 31/166* (2013.01); *A61K 31/18* (2013.01); *A61K 31/351* (2013.01); *A61K 31/4706* (2013.01); *A61K 31/505* (2013.01); *A61K 31/5415* (2013.01); *A61K 31/724* (2013.01); *A61K 39/39558* (2013.01); *A61K 45/06* (2013.01); *C07K 16/2863* (2013.01); *C07K 16/30* (2013.01); *G01N 33/57492* (2013.01); *A61K 2039/505* (2013.01); *C07K 2317/732* (2013.01); *C07K 2317/77* (2013.01)

(58) Field of Classification Search
CPC ................ A61K 45/06; A61K 39/3955; A61K 39/39558; A61K 2300/00; A61K 31/505; A61K 31/4706; A61K 31/5415; A61K 31/166; A61K 31/724; A61K 31/351; A61K 31/18; C07K 16/30; C07K 16/32; C07K 16/2863; C07K 2317/732; G01N 33/57492
See application file for complete search history.

(56) References Cited

U.S. PATENT DOCUMENTS

| | | | |
|---|---|---|---|
| 2005/0137185 A1 | 6/2005 | Lee et al. | |
| 2007/0092512 A1* | 4/2007 | Daaka ................... | A61K 31/65 424/143.1 |
| 2010/0075923 A1 | 3/2010 | Huang et al. | |

FOREIGN PATENT DOCUMENTS

| | | |
|---|---|---|
| WO | 2005/027842 | 3/2005 |
| WO | 2010/033507 | 3/2010 |
| WO | WO2010/132959 | * 11/2010 |

OTHER PUBLICATIONS

Correale P, et al. Cytotoxic drugs up-regulate epidermal growth factor receptor (EGFR) expression in colon cancer cells and enhance their susceptibility to EGFR-targeted antibody-dependent cell-mediated-cytotoxicity (ADCC). European Journal of Cancer, 2010, vol. 46, p. 1703-1711.*
Vieira, A.V. et al. Control of EGF receptor signaling by clathrin-mediated endocytosis. Science, 1996, vol. 274, p. 2086-2089.*
Yang, J. et al. Therapeutic potential and challenges of targeting receptor tyrosine kinase ROR1 with monoclonal antibodies in B-cell malignancies. PLoS One, 2011, vol. 6, No. 6, e21018, p. 1-15.*
Lim, S.H. et al. Fc gamma receptor IIb on target B cells promotes rituximab internalization and reduces clinical efficacy. Blood, 2011, vol. 118, No. 9, p. 2530-2540.*
Daniel, J.A., et al. Phenothiazine-derived antipsychotic drugs inhibit dynamin and clathrin-mediated endocytosis. Traffic, 2015, vol. 16, p. 635-654.*
Van Cutsem, E., et al. Cetuximab and chemotherapy as initial treatment for metastatic colorectal cancer. New England Journal of Medicine, 2009, vol. 360, p. 1408-1417.*
International Search Report for PCT/AU2013/001246, four pages (dated Jan. 2014).
Int'l Preliminary Report on Patentability for PCT/AU2013/001246, seven pages (dated May 2015).
International Search Report for PCT/AU2013/001246, dated Jan. 9, 2014, 4 pages.
Marks et al., "Inhibition of Human Tumor Growth by Intraperitoneal Immunotoxins in Nude Mice", Cancer Res., 1990, vol. 50, No. 2, pp. 288-292.
Ettenson et al., "Comparison of Growth Inhibition of a Human Ovarian Adenocarcinoma Cell Line by Free Monoclonal Antibodies and their Corresponding Antibody Recombinant Ricin A Chain Immunotoxins", Anticancer Res., vol. 8, pp. 833-838.
Mujoo et al., "A Potent and Specific Immunotoxin for Tumor Cells Expressing Disialoganglioside GD2", 1991, Cancer Immunol. Immunother, vol. 34, No. 3, pp. 198-204.

(Continued)

*Primary Examiner* — Robert S Landsman
*Assistant Examiner* — Bruce D. Hissong
(74) *Attorney, Agent, or Firm* — Nixon & Vanderhye P.C.

(57) ABSTRACT

The present invention relates to the use of endocytosis inhibitors, including clathrin-dependent endocytosis inhibitors such as inhibitors of dynamin and antibodies, for enhancing the immune response to cancer, and thereby treating cancers including cancer associated receptor positive cancers.

28 Claims, 36 Drawing Sheets

(56) References Cited

OTHER PUBLICATIONS

Amano et al., "Antigen-Dependent Internalization is related to Rapid Elimination from Plasma of Humanized Anti-HM1.24 Monoclonal Antibody", Drug Metab. Dispos., 2010, vol. 38, No. 12, pp. 2339-2346.
Chung et al. "Cetuximab shows activity in colorectal cancer patients with tumors that do not express the epidermal growth factor receptor by immunohistochemistry" J. Clin. Oncol. vol. 23, No. 9, pp. 1803-1810 (Mar. 2005).
Cunningham et al. "Cetuximab monotherapy and cetuximab plus irinotecan in irinotecan-refractory metastatic colorectal cancer" N. Engl. J. Med. vol. 351, No. 4, pp. 337-345 (Jul. 2004).
Meropol "Epidermal growth factor receptor inhibitors in colorectal cancer: It's time to get back on target" J. Clinical Oncol. vol. 23, No. 9, pp. 1791-1793 (Mar. 2005).
Saltz et al. "Phase II trial of cetuximab in patients with refractory colorectal cancer that expresses the epidermal growth factor receptor" J. Clin. Oncol. vol. 22, No. 7, pp. 1201-1208 (Apr. 2004).
Wang et al. "Nitric oxide regulates endocytosis by S-nitrosylation of dynamin" Proc. Natl. Acad. Sci. USA vol. 103, No. 5, pp. 1295-1300 (Jan. 2006).
De Santes et al. "Radiolabeled antibody targeting of the HER-2/neu oncoprotein" *Cancer Research*, vol. 52, No. 7, pp. 1916-1923 (Apr. 1992).
Van Oosterhout et al. "Cytotoxicity of CD3-ricin a chain immunotoxins in relation to cellular uptake and degradation kinetics" *Cancer Research*, vol. 52, No. 21, pp. 5921-5925 (Nov. 1992).
Extended European search report for related EP 13848409.2, eight pages (dated Mar. 2016).

\* cited by examiner

USE OF ENDOCYTOSIS INHIBITORS AND ANTIBODIES FOR CANCER THERAPY

This application is the U.S. national phase of the International Application No. PCT/AU2013/001246, filed 28 Oct. 2013, which designated the U.S. and claims priority to Australian Provisional Application No. 2012904722 entitled "Agents for Cancer Therapy or Prophylaxis and Uses Therefor" filed 26 Oct. 2012, the contents of each of which are incorporated herein by reference.

FIELD OF THE INVENTION

This invention relates generally to agents for treating or preventing cancers. More particularly, the present invention relates to the use of endocytosis inhibitors, including clathrin-dependent endocytosis inhibitors and dynamin-dependent endocytosis inhibitors for treating cancers including cancer-associated receptor positive cancers. In specific embodiments, the endocytosis inhibitors are used in combination with immunotherapeutic agents to enhance an immune response to a cancer.

Bibliographic details of various citations referred to numerically in the present specification are listed at the end of the description.

BACKGROUND OF THE INVENTION

Antibody therapy has gained widespread acceptance as a promising therapeutic strategy to address several diseases including autoimmune disease and cancer. Despite rapid and exciting progress in developing antibody monotherapies and combination treatments, the disease burden attributable to such illnesses has not significantly abated. The complex nature of the normal and pathologic immunologic processes associated with such diseases, coupled with resistance or acquired resistance to antibody treatment, continue to be some of the obstacles to successful advances in patient outcomes.

For example, antibodies specific for the EGFR are now in clinical use for a number of malignancies. Despite their pro-inflammatory side effects, promising results have been shown in some patients treated with anti-EGFR antibodies, either monotherapy or in combination with radio- or chemotherapy (1). However, a significant proportion of treated patients fail to respond for reasons which have not yet been fully elucidated. An exciting new study in Nature Medicine (2) has shown that some patients carry a mutation in the EGFR which prevents cetuximab binding but not panumitumab binding and thus a further percentage of patients can be screened and be treated with the appropriate anti-EGFR antibody. However, this does not bypass most observed patient resistance. Numerous studies have been carried out to ascertain the mechanism of the noted resistance. EGFR expression is increased in squamous cell carcinoma and other epithelial tumors by several different mechanisms including amplification, gain of expression of the gene and increased rate of EGFR activating mutations.

While specific alterations in EGFR number or function were predicted to affect treatment response, no correlation has been observed in clinical trials (3-7). In 10% of patients resistant to EGFR targeted therapy there are specific activating mutations in the downstream signaling components of the EGFR such as KRAS in the tumors. There is a significant association between absence of response to cetuximab and KRAS status (8-10). A BRAF point mutation, V600E, is one of the most common oncogenic mutations in cells, and a retrospective analysis (11) of patients with metastatic colorectal cancer showed that no BRAF-mutated tumors responded to cetuximab or panitumumab. Analysis of KRAS and BRAF mutational status is now becoming commonplace prior to the use of anti-EGFR antibodies, allowing patients who are unlikely to respond to be selected out and offered alternate treatment such as anti-VEGF therapy. However, these mutations only involve 10% of resistant patients. Mass spectrometry profiling of patient tumor proteomes from responsive versus resistant patients (3) has also been used to predict patient response to EGFR inhibitor treatment but at present the algorithms are not robust enough for use in patient analysis. Attempts to correlate tumor resistance with specific mutations in genes of the EGFR family now involve simultaneous profiling many of genes, which is time-consuming and expensive.

SUMMARY OF THE INVENTION

The present invention is predicated in part on the determination that EGFR positive tumors having impaired or abrogated ligand-induced EGFR internalization (also referred to herein as "disregulated EGFR" or "disregulated EGFR status") are sensitive to anti-EGFR antibody therapy (e.g., cetuximab, panitumumab, etc.), whereas EGFR positive tumors having unimpaired ligand-induced EGFR internalization (also referred to herein as "unimpaired EGFR" or "unimpaired EGFR status") are resistant or refractory to anti-EGFR antibody therapy. The present inventors have also found that patients with tumors having disregulated EGFR showed better clinical outcomes in response to anti-EGFR antibody therapy, as compared to patients with tumors having unimpaired EGFR. Based on these findings, the present inventors hypothesized that inhibition of ligand-induced EGFR internalization in tumors using, for example, inhibitors of receptor-mediated endocytosis would lead to enhanced sensitivity to anti-EGFR antibodies. Surprisingly, in addition to improved sensitivity, they found that inhibition of receptor-mediated endocytosis led to an enhanced immune response, including an enhanced antibody-dependent cellular cytotoxicity (ADCC) response, against the tumor. The present inventors propose generally that impaired trafficking of tumor cell surface antigens such as EGFR into the intracellular compartment will result in more tumor antigen on the surface of a tumor cell, which would, in turn, bind more antibody to the surface antigen and enhance the immune response to the tumor cell.

Thus, the present invention addresses the problem of tumor resistance to antibody therapy by co-administering an inhibitor of receptor-mediated endocytosis with the antibody therapy. This represents a significant advance over current technologies for the management of cancers.

Accordingly, in one aspect, the present invention provides compositions for stimulating an enhanced immune response (e.g., an enhanced antibody-dependent cellular cytotoxicity response) to a tumor in a subject. These compositions generally comprise, consist or consist essentially of an antibody (also referred to herein as a "therapeutic antibody") that binds to a cell surface antigen of the tumor, which antigen is subject to receptor-mediated endocytosis, and an inhibitor of receptor-mediated endocytosis. In some embodiments, the inhibitor of receptor-mediated endocytosis is a clathrin-dependent endocytosis inhibitor, illustrative examples of which include methyl-B-cyclodextrin, a phenothiazine, monodansylcadaverine, chloroquine, monensin and dynamin inhibitors. In some embodiments, the inhibitor of receptor-mediated endocytosis is a dynamin-dependent endocytosis inhibitor, illustrative examples of which include dynamin GTPase inhibitors and dynamin ring stabilizers. Suitably, the cell surface antigen is a tumor associated antigen (e.g., a receptor such as EGFR, VEGFR, FGFR, Her2/neu, CD20, etc.). The inhibitor of receptor-mediated endocytosis and the antibody are suitably administered in the form of one or more compositions each comprising a pharmaceutically acceptable carrier and/or diluent. The composition(s) may be administered by injection, by topical application or by the oral route including sustained-release modes of administration, or a combination thereof, over a period of time and in amounts which are effective for enhancing an immune response to the tumor cell. In some embodiments, the enhanced immune response comprises stimulating or enhancing the expression of MHC class II and class I on the surface of cells of the tumor.

Another aspect of the present invention provides methods for enhancing an immune response (e.g., an enhanced antibody-dependent cellular cytotoxicity response) to a tumor in a subject. These methods generally comprise, consist or consist essentially of administering concurrently to the subject an effective amount an inhibitor of receptor-mediated endocytosis (e.g., a clathrin-dependent endocytosis inhibitor, a dynamin-dependent endocytosis inhibitor, etc.) and an effective amount of an antibody that binds to a cell surface antigen of the tumor, which antigen is subject to receptor mediated endocytosis. In related aspects, the present invention provides methods for treating or preventing a cancer in a subject, wherein the methods generally comprise, consist or consist essentially of concurrently administering to the subject an inhibitor of receptor-mediated endocytosis and an antibody that binds to a cell surface antigen of a tumor associated with the cancer, which antigen is subject to receptor mediated endocytosis, wherein the inhibitor and the antigen are in amounts effective for treatment or prevention the cancer.

Yet another aspect of the present invention provides methods for enhancing the efficacy of an antibody that binds to a cell surface antigen of a tumor in a subject, which antigen is subject to receptor mediated endocytosis. These methods generally comprise, consist or consist essentially of administering to the subject an inhibitor of receptor-mediated endocytosis (e.g., a clathrin-dependent endocytosis inhibitor, a dynamin-dependent endocytosis inhibitor, etc.) in an effective amount to enhance the efficacy of the antibody.

In some embodiments, the methods broadly described above further comprise classifying the tumor into a subtype selected from an antibody sensitive subtype or an antibody resistant subtype and co-administering the inhibitor of receptor-mediated endocytosis and the antibody on the basis that the tumor is classified as an antibody resistant subtype. In illustrative examples of this type, the classification is carried out by a method comprising analyzing the ligand-induced cell surface antigen internalization status of the tumor, wherein an impaired or abrogated ligand-induced cell surface antigen internalization status indicates that the tumor is an antibody sensitive subtype and wherein an unimpaired ligand-induced cell surface antigen internalization of status indicates that the tumor is an antibody resistant subtype. In some embodiments, an impaired or abrogated ligand-induced cell surface antigen internalization is indicated when, suitably after at least 10 minutes (e.g., 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or more minutes) in the presence of a ligand of the cell surface antigen, at least 90% (e.g., 90%, 91%, 92%, 93%, 94%, 95%, 96%, 97%, 98%, 99% or 100%) of the cell surface antigen in cells of the tumor is localized or remains localized to the plasma membrane (e.g., basolateral membrane) of the cells. In some embodiments, an unimpaired ligand-induced cell surface antigen internalization is indicated when, suitably after at least 10 minutes (e.g., 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or more minutes) in the presence of a ligand to the cell surface antigen: (a) less than 100% (e.g., 99%, 98%, 97%, 96%, 95%, 94%, 93%, 92%, 91%, 90%, 85%, 80%, 75%, 70%, 65%, 60%, 55%, 50%, 45%, 40%, 35%, 30%, 25%, 20%, 15%, 10%, 5% or even less) of the cell surface antigen in cell surface antigen-expressing cells of the tumor is localized or remains localized to the plasma membrane (e.g., basolateral membrane) of the cells.

The tumor is generally a cell surface positive tumor and includes pre-cancerous, non-metastatic, metastatic, and cancerous tumors (e.g., early stage cancer). Representative cancers are selected from carcinoma, lymphoma, blastoma, sarcoma, neuroendocrine tumors, mesothelioma, schwannoma, meningioma, adenocarcinoma, melanoma, leukemia, and lymphoid malignancies. In some embodiments, the cancer is selected from lung cancer, hepatocellular cancer, gastric or stomach cancer, pancreatic cancer, glioblastoma, cervical cancer, ovarian cancer, liver cancer, bladder cancer, hepatoma, breast cancer, colon cancer, rectal cancer, colorectal cancer, endometrial and uterine carcinoma, salivary gland carcinoma, kidney cancer, prostate cancer, vulval cancer, thyroid cancer, hepatic carcinoma, anal carcinoma, penile carcinoma, testicular cancer, esophageal cancer, tumors of the biliary tract, and head and neck cancer. In specific embodiment, the tumor is of an epithelial origin, non-limiting examples of which include cancer of the lung, colon, prostate, ovary, breast, and skin (e.g., squamous cell carcinoma (SCC)).

In a related aspect, the methods broadly described above may optionally further comprise stratifying the subject into a treatment subgroup selected from responder to the antibody and non-responder to the antibody and co-administering the inhibitor of receptor-mediated endocytosis and the antibody on the basis that the subject is stratified as a non-responder. In illustrative examples of this type, the stratification is carried out by a method comprising classifying the tumor according to the tumor classification methods broadly described above, and identifying the subject as a responder to the antibody if the tumor of the subject is analyzed as having an impaired or abrogated ligand-induced cell surface antigen internalization status or identifying the subject as a non-responder to the antibody if the tumor of the subject is analyzed as having an unimpaired ligand-induced cell surface antigen internalization status. In some embodiments, the methods further comprise obtaining a tumor sample from the subject for the analysis.

The above methods for stratification of the subject into treatment subgroups are not necessary. Accordingly, the present invention further contemplates co-administering the therapeutic antibody and inhibitor of receptor-mediated endocytosis to a subject regardless of whether the subject is, is known or is suspected to be a responder or non-responder as the administration of inhibitor will stimulate the development, enhance or otherwise maintain an antibody responder status in the subject.

In some embodiments, the methods further comprise co-administering an ancillary cancer therapy to the subject. In some embodiments, the ancillary therapy is selected from radiotherapy, surgery, chemotherapy, hormone ablation therapy, pro-apoptosis therapy and immunotherapy other than the antibody.

Yet another aspect of the present invention provides the use of an inhibitor of receptor-mediated endocytosis (e.g., a clathrin-dependent endocytosis inhibitor, a dynamin-dependent endocytosis inhibitor, etc.) and an antibody that binds a cell surface antigen of a tumor, which antigen is subject to receptor mediated endocytosis optionally in the manufacture of a medicament for enhancing an immune response (e.g., an enhanced antibody-dependent cellular cytotoxicity response) to a tumor or for treating or preventing a cancer in a subject.

The present invention also extends to the use of inhibitors of receptor-mediated endocytosis identified by any suitable screening method. In some embodiments, the screening method comprises (1) contacting a preparation with a test agent, wherein the preparation comprises (i) a polypeptide comprising an amino acid sequence corresponding to at least a biologically active fragment of a dynamin polypeptide; or (ii) a polynucleotide comprising a nucleotide sequence from which a transcript of a dynamin gene or portion thereof is producible, or (iii) a polynucleotide comprising at least a portion of a genetic sequence that regulates the expression of a dynamin gene, which is operably linked to a reporter gene; and (2) detecting a change in the level or functional activity of the polypeptide, the polynucleotide or an expression product of the reporter gene, relative to a reference level or functional activity in the absence of the test agent. A detected reduction in the level and/or functional activity of the polypeptide, transcript or transcript portion or an expression product of the reporter gene, relative to a normal or reference level and/or functional activity in the absence of the test agent, indicates that the agent is a dynamin inhibitor. In illustrative examples of this type, this is confirmed by analyzing or determining whether the test agent enhances the antibody-dependent cellular cytotoxicity response to a tumor having a cell surface receptor that is subject to receptor-mediated endocytosis (e.g., EGFR, VEGFR, FGFR, Her/neu2, CD20 etc.), optionally in combination with an antibody to the cell surface receptor.

In some embodiments, inhibitors of receptor-mediated endocytosis are identified by methods that assay dynamin ring stabilization. These methods may comprise incubating a test agent with a dynamin polypeptide under conditions suitable for the formation of dynamin rings; and evaluating whether the test agent promotes accumulation of dynamin rings and/or inhibits disassembly of dynamin rings, the accumulation of dynamin rings and/or inhibition of disassembly of dynamin rings increasing basal dynamin GTPase activity. The evaluation of whether the test agent promotes the accumulation of dynamin rings or inhibits disassembly of dynamin rings can involve assaying for an increase in basal dynamin GTPase activity, and/or release of dynamin that is indicative of dynamin ring disassembly.

Still another aspect of the present invention provides methods of producing an agent for enhancing the antibody-dependent cellular cytotoxicity response to a tumor having a cell surface receptor that is subject to receptor-mediated endocytosis (e.g., EGFR, VEGFR, FGFR, Her/neu2, CD20 etc.). These methods generally comprise: testing an agent suspected of inhibiting receptor-mediated endocytosis as broadly described above and elsewhere herein; and synthesizing the agent on the basis that it tests positive for the inhibition. Suitably, the method further comprises derivatizing the agent, and optionally formulating the derivatized agent with a pharmaceutically acceptable carrier and/or diluent, to improve the efficacy of the agent for enhancing the antibody-dependent cellular cytotoxicity response to a tumor having a cell surface receptor that is subject to receptor-mediated endocytosis.

$$\% \text{ of untreated cells} = (\text{experimental } OD - PBMC\ OD)/(A431\text{ maximum } OD - \text{medium } OD) \times 100\%$$

Figure 25:
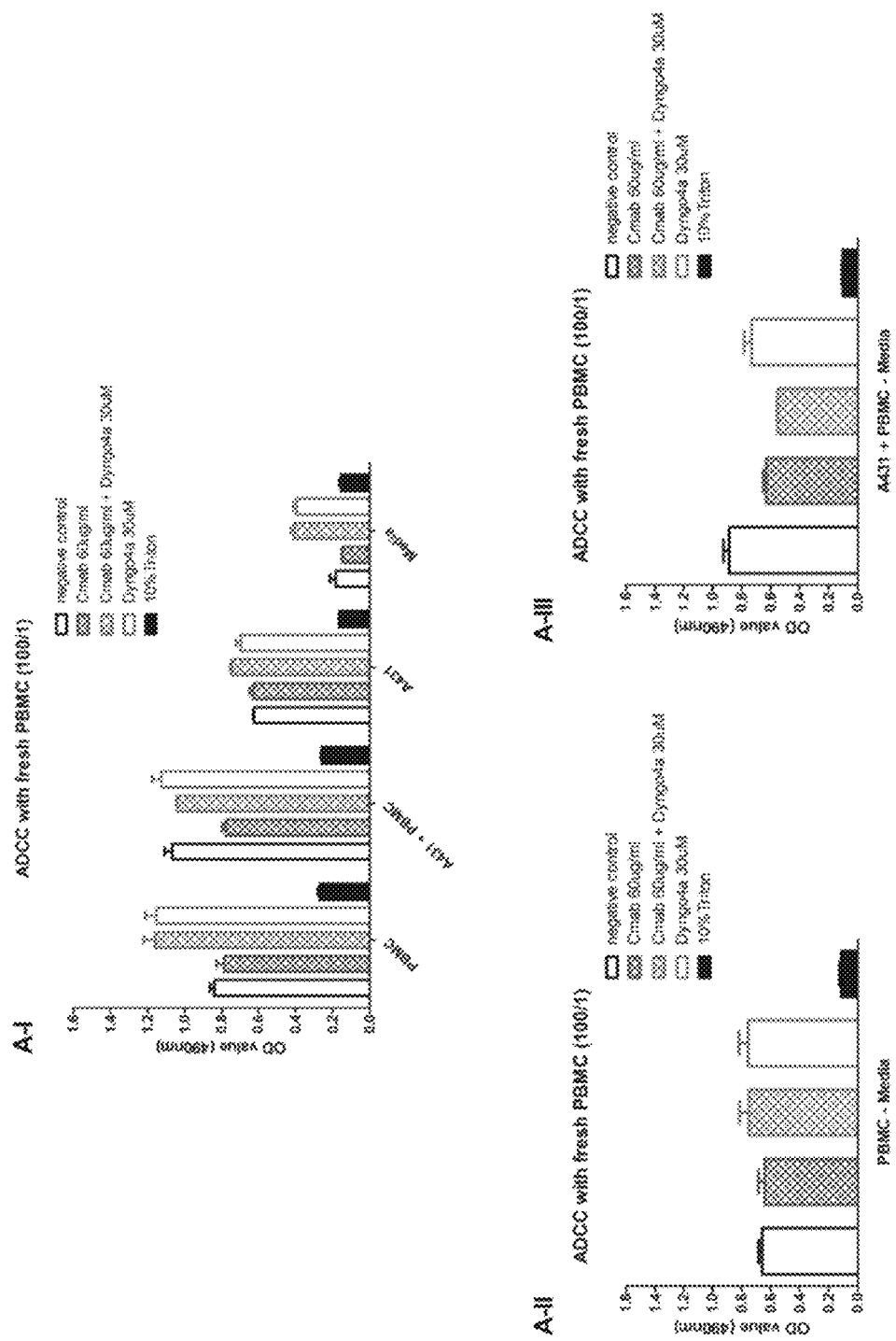

FIG. 25 is a graphical representation showing that the dynamin inhibitor, Dyngo4a, enhances cetuximab mediated ADCC effect without causing viability reduction of effector cells. (AI-III) To test the effect of Dyngo4a on cetuximab mediated ADCC, 2500 A431 cells were incubated with fresh PBMCs (E/T=100/1) and 60 µg/mL cetuximab for 24 hours. Dyngo4a (0 and 30 µM) was added at the end of the incubation. 10% Triton was added to A431 cells after 24-hour incubation with PBMCs for cell death control. The ADCC effects were measured by MTS assay. The cell viability was presented as OD values at 490 nm. The average of OD values released from background was subtracted from effector cell controls (A-II) and target/effector tests (A-III). (A-II) Addition of Dyngo4a did not cause a viability reduction of effector cells. (C-III) Addition of Dyngo4a enhances cetuximab mediated ADCC.

Figure 26:
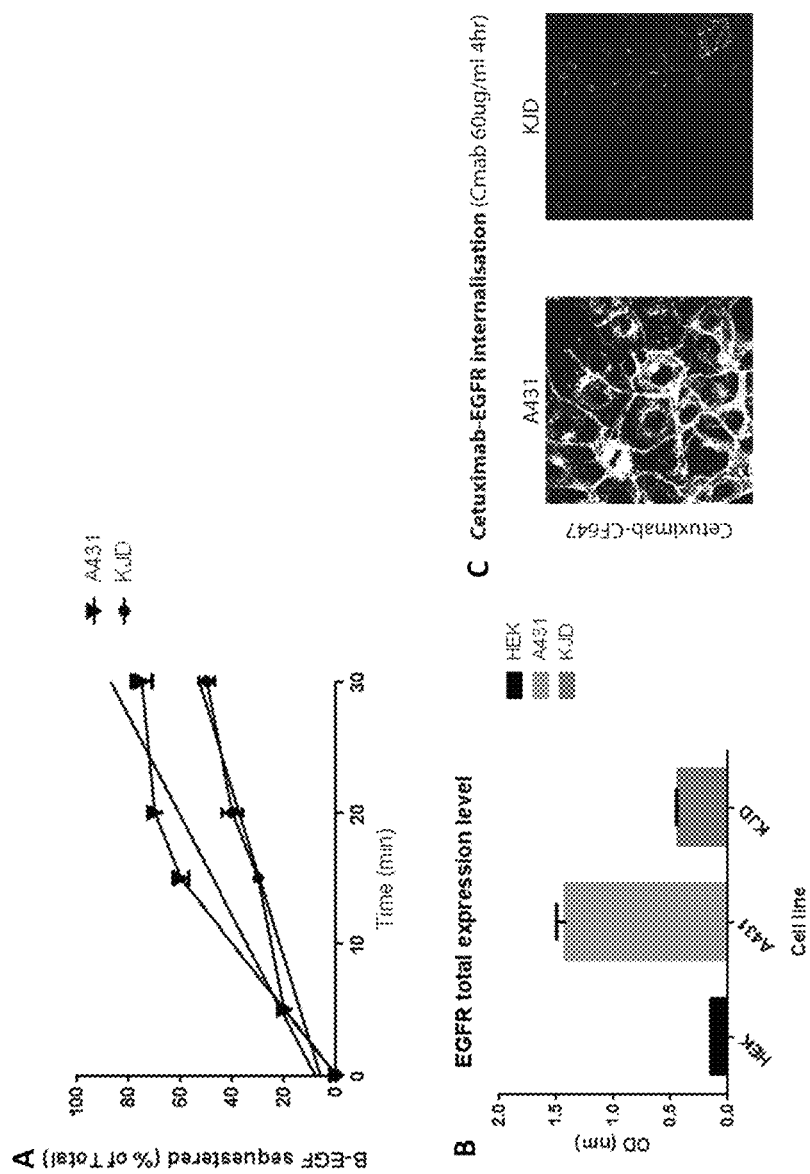

FIG. 26 is a graphical and photographic representation showing EGFR total expression levels and EGFR endocytosis rates in A431 and KJD cell lines. (A) Rates of EGF internalization in SCC cell lines are variable and exhibit disregulation in initial uptake. (Panel A) Biotin-EGF uptake was performed in SCC cell lines for the time points indicated. Endocytosis was measured as avidin inaccessibility as a percentage of total at 15 min. Assays were performed as described in Methods Online. Data shown are the average of 3 experiments+/−SEM. (B) Levels of EGFR expression in both A431 and KJD SCC cell lines are increased compared to HEK cells. Equal protein concentrations of SCC and HEK cell lysates were subjected to ELISA assay for EGFR levels (Methods Online). Data shown are an average of 3 experiments+/−SEM by non-paired T-test. (C) A431 and KJD cells were incubated at 37° C. for 4 hours with 60 µg/mL cetuximab anti-EGFR monoclonal antibody prior to fixation and post-fixation labeling with anti-human-CF$^{647}$. While surface-bound cetuximab is still clearly visible in A431 cells, plasma membrane exposed Cetuximab is reduced in KJD cells.

FIG. 27 is a photographic and graphical representation of a multi-parametric FACS analysis showing that manipulation of EGFR trafficking with dynamin inhibitors results in increased ADCC in cetuximab-sensitive cells. (A) Immunofluorescence imaging of cetuximab trafficking status in A431 cells. (B) A431 cells were labeled with 0.5 nM CFSE and then incubated with fresh PBMCs (E/T=50/1) under indicated conditions: cetuximab (60 µg/mL) treatment for 4 hours; addition of Dyngo4a (30 µM) followed by co-incubation with cetuximab (60 µg/mL) for 4 hours; addition of Dyngo4a (30 µM) followed by co-incubation with cetuximab (60 µg/mL) for 4 hours and a second Dyngo4a (30 µM) treatment for the last two hours; Cetuximab (60 µg/mL) treatment for 3 hours followed by addition of Dyngo4a (30 µM) for one hour co-incubation. 7-AAD was added at the end of the 4-hour assay to label dead cells prior to FACS analysis. Gating strategies used for the assessment of specific target cell death are shown. FITC indicates CFSE while PerCP-Cy5.5 indicates 7-AAD. The dead target cells appear in the upper right quadrant, CFSE painted and 7-AAD positive. (C.1) A431 cell death under different conditions. (C.2) The percentage of specific A431 cell death was calculated. Data shown are an average of 3 experiments+/−SEM by Two-Way ANOVA with Bonferroni post test. **: $P \leq 0.0001$; *: $P \leq 0.001$; **: $P \leq 0.01$; *: $P \leq 0.05$. ns: no significance.

Figure 28A:
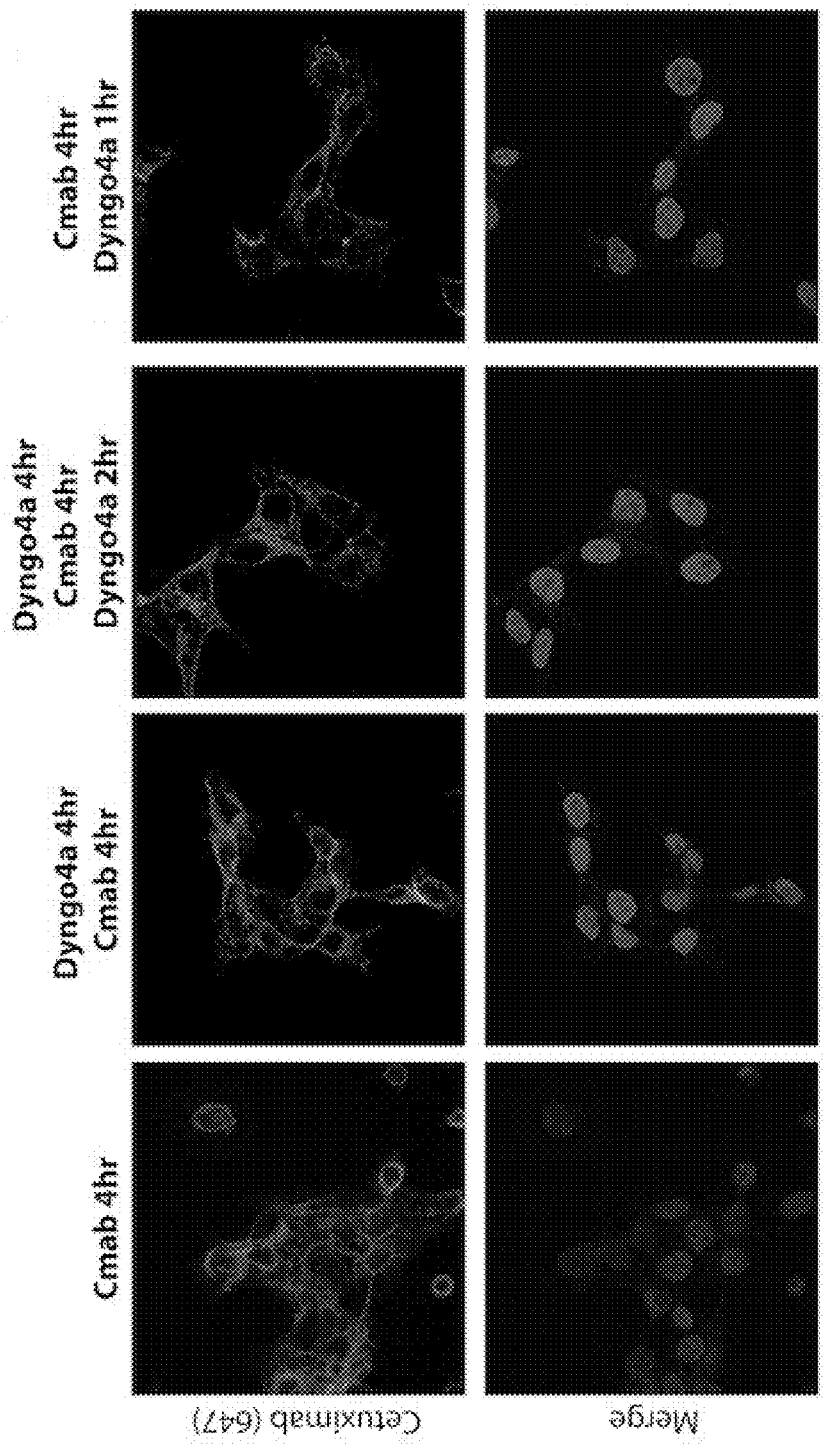
Figure 28B:
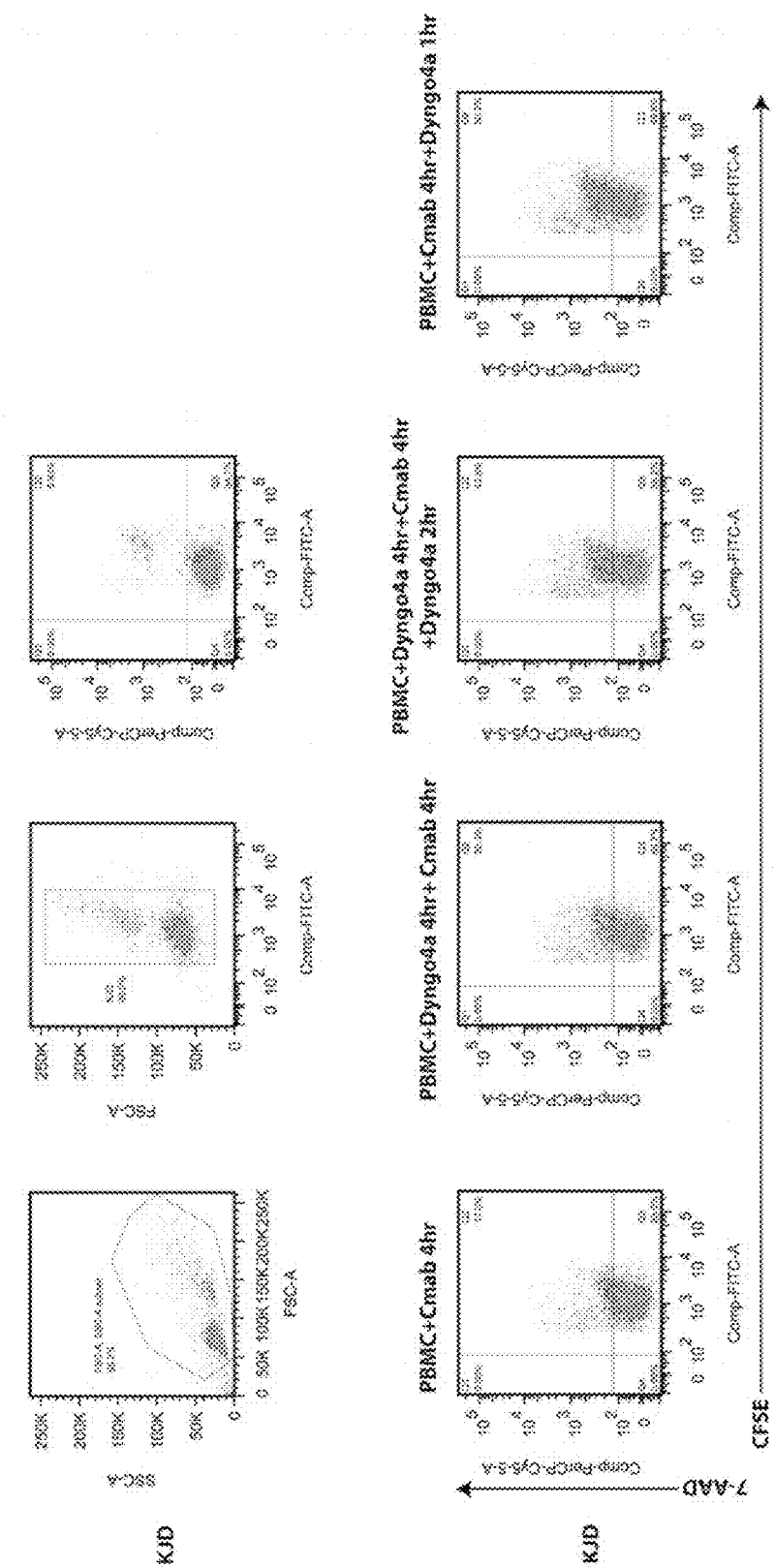

FIG. 28 is a photographic and graphical representation of a multi-parametric FACS analysis showing that manipulation of EGFR trafficking with dynamin inhibitors results in improved ADCC in cetuximab-insensitive cells. (A) Immunofluorescence imaging of cetuximab trafficking status in KJD cells. (B) KJD cells were labeled with 0.5 nM CFSE and then incubated with fresh PBMCs (E/T=50/1) under indicated conditions: cetuximab (60 µg/mL) treatment for 4 hours; addition of Dyngo4a (30 µM) followed by co-incubation with cetuximab (60 µg/mL) for 4 hours; addition of Dyngo4a (30 µM) followed by co-incubation with cetuximab (60 µg/mL) for 4 hours and a second Dyngo4a (30 µM) treatment for the last two hours; Cetuximab (60 µg/mL) treatment for 3 hours followed by addition of Dyngo4a (30 µM) for one hour co-incubation. 7-AAD was added at the end of the 4-hour assay to label dead cells prior to FACS analysis. (B) Gating strategies used for the assessment of specific target cell death. FITC indicates CFSE while PerCP-Cy5.5 indicates 7-AAD. The dead target cells appear in the upper right quadrant, CFSE painted and 7-AAD positive. (C.1) KJD cell death under different conditions. (C.2) The percentage of specific KJD cell death was calculated. Data shown are an average of 3 experiments+/−SEM by Two-Way ANOVA with Bonferroni post test. **: $P \leq 0.0001$; *: $P \leq 0.001$; **: $P \leq 0.01$; *: $P \leq 0.05$. ns: no significance.

Figure 29:
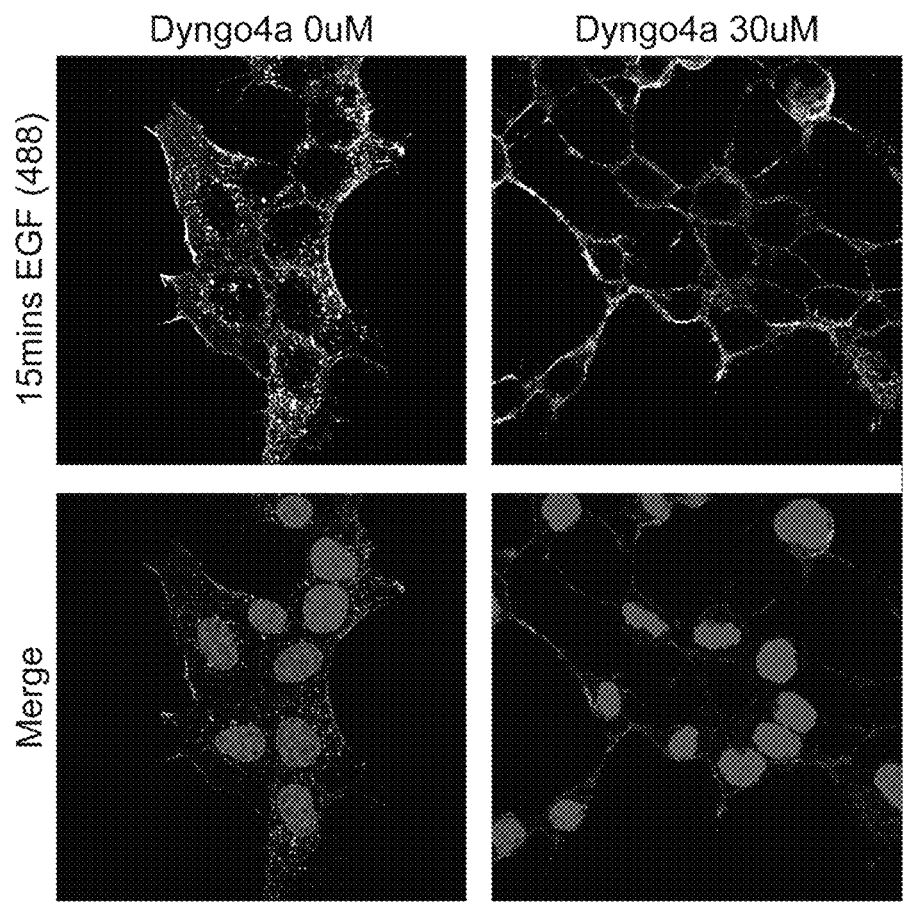

FIG. 29 is a photographic representation showing Dyngo4a inhibition of EGFR endocytosis. The dynamin inhibitor Dyngo4a shows an inhibitory effect on the ligand-induced EGFR endocytosis. Immunofluorescence was conducted to confirm the manipulation of EGFR trafficking using Dyngo4a. A431 cells were serum-starved for 3 hours and then treated with different concentrations of (A) Dyngo4a (0 and 30 µM) for 30 min. Fifteen-minute EGF-Alexa$^{488}$ (100 ng/mL) uptakes were performed to monitor the trafficking of the ligand bound EGFRs (in green). The nuclei are shown in blue.

FIG. 30 is a graphical representation of a multi-parametric FACS analysis showing that manipulation of EGFR trafficking with dynamin inhibitors, Dyngo4a and Pyrimidyn-7, results in enhanced ADCC in cetuximab-sensitive and insensitive cells. cetuximab-dependent ADCC assays were performed essentially according to the procedures outlined in FIGS. 27 and 28. (A) Percentage of specific A431 cell death is shown in the presence of dynamin inhibitors with cetuximab in the absence of PBMC to test non-ADCC cell death. (B) (I) Percentage of specific A431 cell death is shown in the absence and presence of Dyngo4a inhibitor and cetuximab in the presence of PBMC. (II) Percentage of specific A431 cell death is shown in the absence and presence of Pyrimidyn-7 inhibitor and cetuximab in the presence of PBMC. (C) Percentage of specific KJD cell death is shown in the presence of dynamin inhibitors only. (D) Percentage of specific KJD cell death is shown in the presence of dynamin inhibitors and cetuximab. (E) An MTS assay was conducted in the absence of PBMC to assess toxicity of compounds in the absence of ADCC. Graph E shows test of cetuximab-sensitive A431 cells. Dyngo4a combined with cetuximab has no significant toxicity on A431 cells, while Pyrimidyn-7 shows significant death of A431 cells in the absence of ADCC. Triton X100 is added as a control for maximum cell death. (F) An MTS assay was conducted in the absence of PBMC to assess toxicity of compounds in the absence of ADCC. Graph F shows test of cetuximab-insensitive KJD cells. Dyngo4a combined with cetuximab has no significant toxicity on KJD cells, while Pyrimidyn-7 shows significant death of KJD cells in the absence of ADCC. Triton X100 is added as a control for maximum cell death. (G) An MTS assay was conducted to assess possible toxicity of dynamin inhibitors to PBMC cells. The data show that Dyngo4a has no significant toxicity or effect on. PBMC viability while Pyrimidyn-7 shows toxicity. Triton X100 is added as a control for maximum cell death.

Figure 31:
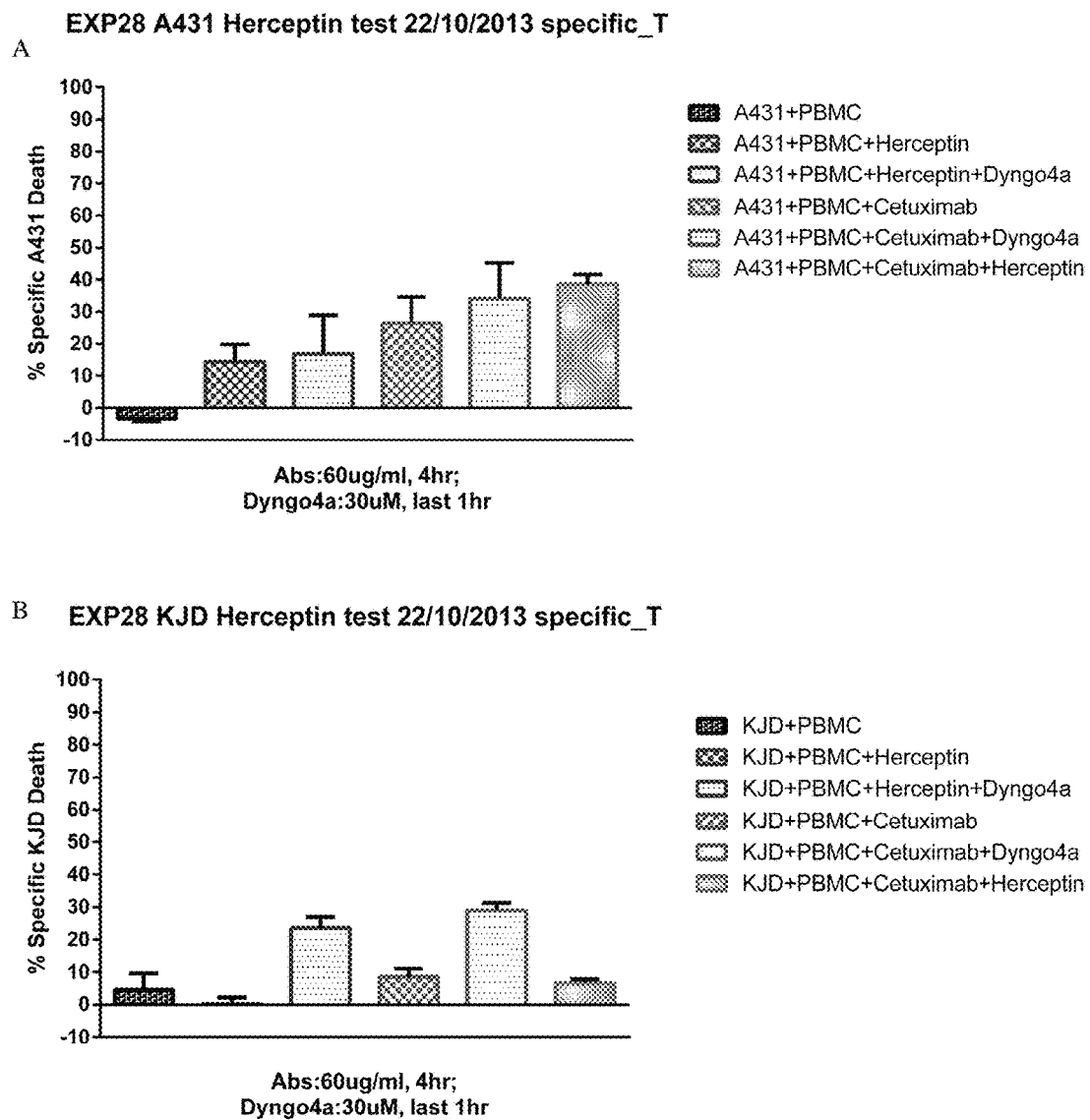

FIG. 31 is a graphical representation of a multi-parametric FACS analysis showing that manipulation of EGFR trafficking with Dyngo4a results in enhanced ADCC in Herceptin-sensitive and insensitive cells. As for cetuximab, A431 cells express some ErbB2 receptor and this is expressed on the plasma membrane, although at a lower level than EGFR (ErbB1) and are sensitive to Herceptin-mediated ADCC. KJD cells express low levels of ErbB2 which is largely localized in internal cellular compartments, therefore KJD are insensitive to Herceptin-mediated ADCC. Translocating the ErbB2 receptor to the plasma membrane during the course of the ADCC assay using by addition of Dyngo4a improves ADCC in the sensitive A431 cells and also causes KJD to become sensitive to Herceptin-mediated ADCC.

Figure 32:
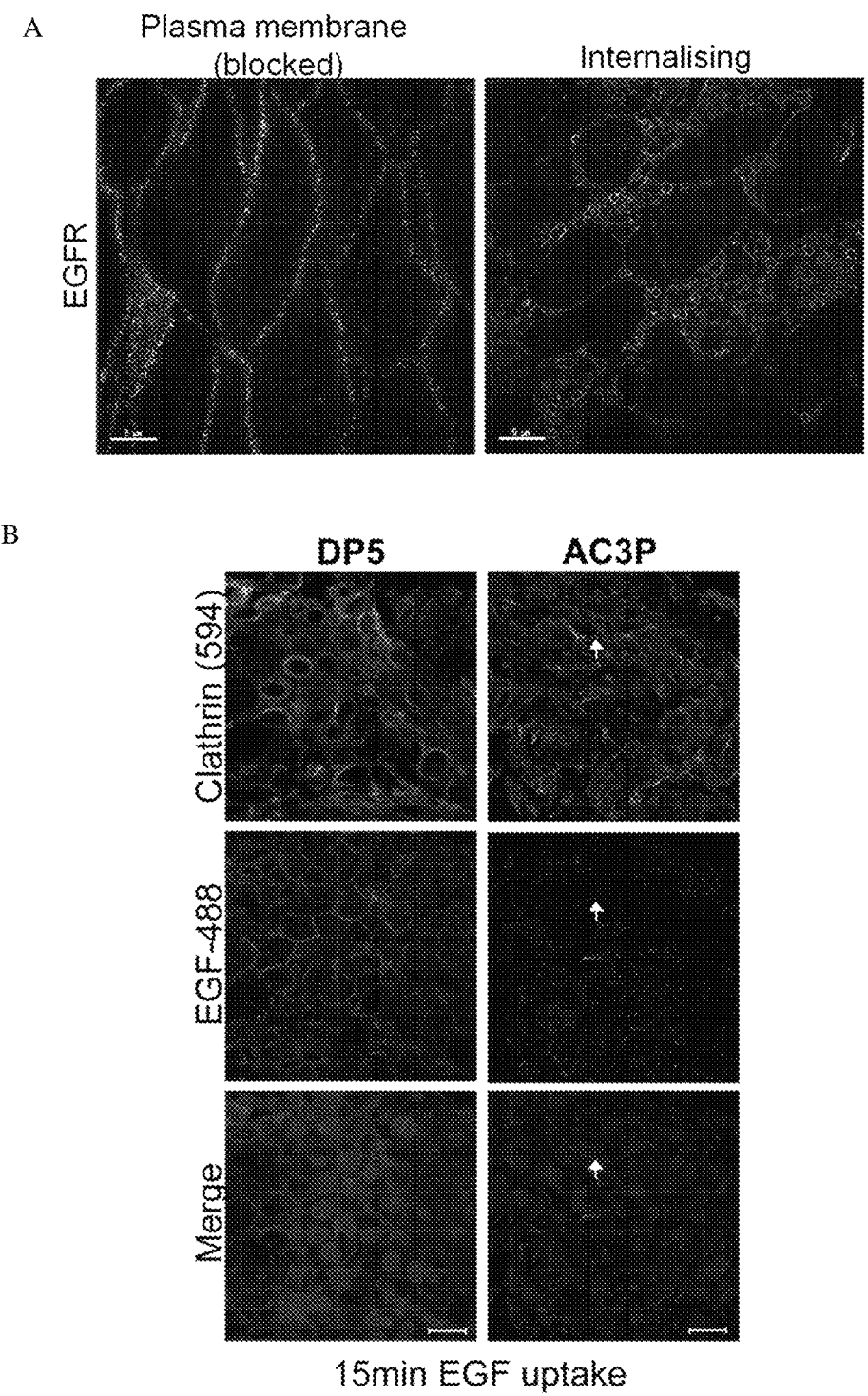

FIG. 32 is a photographic representation showing Super-resolution microscopy of human tumor EGFR endocytosis. (A) Super-resolution microscopy of a human SCC in which EGFR does not undergo normal ligand-induced internalization (Plasma membrane (blocked) and a human SCC in which EGFR retains ligand-induced internalization function. At this resolution the different distribution of EGF-Alexa$^{488}$ in the two samples could be clearly observed. Nuclei are indicated by white dotted lines. The endosomal structures in the human tissue appear quite large in comparison to similar structures observed in tissue culture cells. Scale bars: 5 µm. (B) Co-localization of clathrin and internalized EGF-Alexa488 in tumors AC3P and DP5.

Some figures and text contain color representations or entities. Color illustrations are available from the Applicant upon request or from an appropriate Patent Office. A fee may be imposed if obtained from a Patent Office.

DETAILED DESCRIPTION OF THE INVENTION

1. Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The use of numerical values in the various ranges specified in this application, unless expressly indicated otherwise, are stated as approximations as though the minimum and maximum values within the stated ranges were both preceded by the word "about." In this manner, slight variations above and below the stated ranges (e.g., less than or equal to 10%, 9%, 8%, 7%, 6%, 5%, 4%, 3%, 2%, 1%) can be used to achieve substantially the same results as values within the ranges. Also, the disclosure of these ranges is intended as a continuous range including every value between the minimum and maximum values.

The articles "a" and "an" are used herein to refer to one or to more than one (i.e. to at least one) of the grammatical object of the article. By way of example, "an element" means one element or more than one element.

The terms "administration concurrently" or "administering concurrently" or "co-administering" and the like refer to the administration of a single composition containing two or more actives, or the administration of each active as separate compositions and/or delivered by separate routes either contemporaneously or simultaneously or sequentially within a short enough period of time that the effective result is equivalent to that obtained when all such actives are administered as a single composition. By "simultaneously" is meant that the active agents are administered at substantially the same time, and desirably together in the same formulation. By "contemporaneously" it is meant that the active agents are administered closely in time, e.g., one agent is administered within from about one minute to within about one day before or after another. Any contemporaneous time is useful. However, it will often be the case that when not administered simultaneously, the agents will be administered within about one minute to within about eight hours and suitably within less than about one to about four hours. When administered contemporaneously, the agents are suitably administered at the same site on the subject. The term "same site" includes the exact location, but can be within about 0.5 to about 15 centimeters, preferably from within about 0.5 to about 5 centimeters. The term "separately" as used herein means that the agents are administered at an interval, for example at an interval of about a day to several weeks or months. The active agents may be administered in either order. The term "sequentially" as used herein means that the agents are administered in sequence, for example at an interval or intervals of minutes, hours, days or weeks. If appropriate the active agents may be administered in a regular repeating cycle.

The term "antibody" herein is used in the broadest sense and specifically covers monoclonal antibodies, polyclonal antibodies, multispecific antibodies (e.g., bispecific antibodies), antibody fragments, or any other antigen-binding molecule so long as they exhibit the desired biological activity.

The term "monoclonal antibody" as used herein refers to an antibody from a population of substantially homogeneous antibodies, i.e., the individual antibodies comprising the population are identical and/or bind the same epitope(s), except for possible variants that may arise during production of the monoclonal antibody, such variants generally being present in minor amounts. Such monoclonal antibody typically includes an antibody comprising a polypeptide sequence that binds a target (e.g., a target antigen), wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones or recombinant DNA clones. It should be understood that the selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations which typically include different antibodies directed against different determinants (epitopes), each monoclonal antibody of a monoclonal antibody preparation is directed against a single determinant on an antigen. In addition to their specificity, the monoclonal antibody preparations are advantageous in that they are typically uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method (e.g., Kohler et al., Nature, 256:495 (1975); Harlow et al., Antibodies: A Laboratory Manual, (Cold Spring Harbor Laboratory Press, 2nd ed. 1988); Hammerling et al., in: Monoclonal Antibodies and T-Cell Hybridomas 563-681, (Elsevier, N.Y., 1981)), recombinant DNA methods (see, e.g., U.S. Pat. No. 4,816,567), phage display technologies (see, e.g., Clackson et al. (1991) *Nature* 352:624-628; Marks et al. (1991). *J. Mol. Biol.* 222:581-597; Sidhu et al. (2004) *J. Mol. Biol.* 338(2):299-310; Lee et al. (2004) *J. Mol. Biol.* 340(5):1073-1093; Fellouse (2004) *Proc. Nat. Acad Sci. USA* 101(34):12467-12472; and Lee et al. (2004) *J. Immunol. Methods* 284(1-2):119-132, and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al. (1993) *Proc. Natl. Acad. Sci. USA* 90:2551; Jakobovits et al. (1993) *Nature* 362:255-258; Bruggemann et al. (1993) *Year in Immuno.* 7:33; U.S. Pat. Nos. 5,545,806; 5,569,825; 5,591,669 (all of GenPharm); U.S. Pat. No. 5,545,807; WO 1997/17852; U.S. Pat. Nos. 5,545,807; 5,545,806; 5,569,825; 5,625,126; 5,633,425; and 5,661,016; Marks et al. (1992) *Bio/Technology* 10: 779-783; Lonberg et al. (1994) *Nature* 368: 856-859; Morrison (1994) *Nature,* 368: 812-813; Fishwild et al. (1996) *Nature Biotechnology* 14: 845-851; Neuberger (1996) *Nature Biotechnology* 14: 826; and Lonberg and Huszar (1995) *Intern. Rev. Immunol.* 13: 65-93).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al. (1984) *Proc. Natl. Acad Sci. USA* 81:6851-6855). Chimeric antibodies of interest herein include "primatized" antibodies comprising variable domain antigen-binding sequences derived from a non-human primate (e.g., Old World Monkey, Ape etc.) and human constant region sequences, as well as "humanized" antibodies.

"Humanized" forms of non-human (e.g., rodent) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fe), typically that of a human immunoglobulin. For further details, see Jones et al. (1986) *Nature* 321:522-525; Riechmann et al. (1988) *Nature* 332:323-329; and Presta (1992) *Curr. Op. Struct. Biol.* 2:593-596.

"Antibody fragments" comprise a portion of an intact antibody, suitably comprising the antigen binding region thereof. Examples of antibody fragments include Fab, Fab', F(ab)$_2$, and Fv fragments; diabodies; linear antibodies; single-chain antibody molecules; and multispecific antibodies formed from antibody fragment(s).

An antibody "that binds" an antigen of interest (e.g., a tumor surface antigen such as EGFR) is one that binds the antigen with sufficient affinity such that the antibody is useful as a therapeutic agent in targeting a cell or tissue expressing the antigen, and does not significantly cross-react with other proteins. In such embodiments, the extent of binding of the antibody to a "non-target" protein will be less than about 10% of the binding of the antibody, oligopeptide or other organic molecule to its particular target protein as determined by fluorescence activated cell sorting (FACS) analysis or radioimmunoprecipitation (RIA). With regard to the binding of an antibody to a target molecule, the term "specific binding" or "specifically binds to" or is "specific for" a particular polypeptide or an epitope on a particular polypeptide target means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target, for example, an excess of non-labeled target. In this case, specific binding is indicated if the binding of the labeled target to a probe is competitively inhibited by excess unlabeled target.

"Antibody-dependent cell-mediated cytotoxicity" and "ADCC" refer to a cell-mediated reaction in which nonspecific cytotoxic cells that express Fc receptors (FcRs) (e.g., Natural Killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and Fc. 7RIII. FcR expression on hematopoietic cells in summarized is Table 3 on page 464 of Ravetch and Kinet, (1991) *Annu. Rev. Immunol.* 9:457-92. To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. (1998) *Proc. Natl. Acad. Sci. USA* 95:652-656.

As used herein an "antibody sensitive tumor" refers to a tumor in which at least 30%, 40%, 50%, 60%, 70%, 80%, 90%, 95% or up to 100% of cells in the tumor, which express a cell surface antigen to which an antibody binds, have an impaired or abrogated ligand-induced cell surface antigen internalization.

As used herein an "antibody resistant tumor" refers to tumor in which at least 30%, 40%, 50%, 60%, 70%, 80%, 90%, 95% or up to 100% of cells in the tumor, which express a cell surface antigen to which an antibody binds, have an unimpaired ligand-induced cell surface antigen internalization.

The term "antigen" as used herein, means a molecule which is reactive with a specific antibody.

By "antigen-binding molecule" is meant a molecule that has binding affinity for a target antigen. It will be understood that this term extends to immunoglobulins, immunoglobulin fragments and non-immunoglobulin derived protein frameworks that exhibit antigen-binding activity.

The term "cell surface antigen-expressing cell." as used herein refers to cells that express an antigen n their surface. "Cell surface antigen expression" refers to conversion of the information encoded in by a gene encoding the cell surface antigen into messenger RNA (mRNA) and then to the cell surface antigen polypeptide.

The term "cell surface antigen-positive tumor" as used herein refers to a tumor that contains at least 1%, particularly at least 2%, 3%, 4% or 5%, particularly at least 10%, 20%, 30%, 40%, 50%, 60%, 70%, 80%, 90% cell surface antigen-expressing cells, detected e.g. by an immunohistochemistry test. In specific embodiments, the cell surface antigen positive cells overexpress the cell surface antigen. By "overexpression of cell surface antigen" and the like is intended to mean an abnormal level of expression of cell surface antigen in a cell from a tumor within a specific tissue or organ of a patient relative to the level of expression in a normal cell from that tissue or organ. Patients having a cancer characterized by overexpression of the cell surface antigen can be determined by standard assays known in the art, as for example noted above. Cancers characterized by cell surface antigen-positive tumor are referred to herein as "cell surface antigen-positive cancers."

Throughout this specification, unless the context requires otherwise, the words "comprise," "comprises" and "comprising" will be understood to imply the inclusion of a stated step or element or group of steps or elements but not the exclusion of any other step or element or group of steps or elements. Thus, use of the term "comprising" and the like indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

By "effective amount," in the context of treating or preventing a disease or condition (e.g., a cancer) is meant the administration of an amount of active agent to a subject, either in a single dose or as part of a series or slow release system, which is effective for the treatment or prevention of that disease or condition. The effective amount will vary depending upon the health and physical condition of the subject and the taxonomic group of individual to be treated, the formulation of the composition, the assessment of the medical situation, and other relevant factors.

The term "impaired ligand-induced cell surface antigen internalization" or "impaired internalization of cell surface antigen" refers to reduced or abrogated internalization of a cell surface antigen in a cell surface antigen positive cell from a tumor when the cell surface antigen is bound by a cognate ligand (e.g., in the case of EGFR as the cell surface antigen, the cognate ligand may be selected from EGF, TGF-α, amphiregulin, heparin-binding EGF-like growth factor, betacellulin, and epiregulin), as compared with internalization of the cell surface antigen in a normal cell surface antigen-expressing cell when the cell surface antigen is bound by the same ligand. In specific embodiments, an impaired or abrogated ligand-induced internalization of the cell surface antigen is indicated when, suitably after at least 10 minutes (e.g., 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or more minutes) in the presence of a cell surface antigen ligand, at least 90% (e.g., 90%, 91%, 92%, 93%, 94%, 95%, 96%, 97%, 98%, 99% or 100%) of the cell surface antigen in cells of the tumor is localized or remains localized to the plasma membrane (e.g., basolateral membrane localization) of the cells. By contrast, an "unimpaired ligand-induced cell surface antigen internalization" or "unimpaired internalization of cell surface antigen" refers to the same, similar or greater internalization of the cell surface antigen in a cell surface antigen positive or negative cell from a tumor when the cell surface antigen is bound by a cognate ligand, as compared with internalization of the cell surface antigen in a normal cell surface antigen-expressing cell when the cell surface antigen is bound by the same ligand. In some embodiments, an unimpaired ligand-induced internalization of a cell surface antigen is indicated when, suitably after at least 10 minutes (e.g., 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or more minutes) in the presence of a cell surface antigen ligand, less than 90%, 85%, 80%, 75%, 70%, 65%, 60%, 55%, 50%, 45%, 40%, 35%, 30%, 25%, 20%, 15%, 10% or even less of the cell surface antigen in cells of the tumor is localized or remains localized to the plasma membrane (e.g., basolateral membrane localization) of the cells.

As used herein, the terms "label" and "detectable label" refer to a molecule capable of being detected, where such molecules include, but are not limited to, radioactive isotopes, fluorescers (fluorophores), chemiluminescers, chromophores, enzymes, enzyme substrates, enzyme cofactors, enzyme inhibitors, dyes, metal ions, metal sols, ligands (e.g., biotin, avidin, streptavidin or haptens), intercalating dyes and the like. The term "fluoresces" or "fluorophore" refers to a substance or a portion thereof which is capable of exhibiting fluorescence in a detectable range.

The term "ligand" as used herein refers to a naturally occurring or synthetic compound that binds to a cell surface antigen (e.g., a receptor such as EGFR, VEGFR, FGFR, Her2/neu, CD20, etc.). Upon binding to a cell surface antigen, ligands generally lead to the modulation of activity of the cell surface antigen. The term is intended to encompass naturally occurring compounds, synthetic compounds and/or recombinantly produced compounds. As used herein, this term can encompass agonists, antagonists, and inverse agonists.

As used herein, the terms "ligand-induced internalization," "ligand-induced receptor internalization," "ligand-induced receptor-mediated endocytosis," "ligand-induced cell surface antigen internalization," "ligand-induced cell surface antigen-mediated and the like are used interchangeably to refer to a process by which a ligand binds to a cell surface antigen, which is generally a receptor, on the surface of the cell membrane and the resulting ligand-cell surface antigen complex is internalized by the cell, i.e., moves into the cytoplasm of the cell (e.g., a cancer cell) or a compartment within the cytoplasm of the cell (endosomes, vesicles etc.) without causing irreparable damage to the cell membrane. Internalization may be followed up by dissociation of the resulting complex within the cytoplasm.

The terms "patient," "subject," "host" or "individual" used interchangeably herein, refer to any subject, particularly a vertebrate subject, and even more particularly a mammalian subject, for whom therapy or prophylaxis is desired. Suitable vertebrate animals that fall within the scope of the invention include, but are not restricted to, any member of the subphylum Chordata including primates (e.g., humans, monkeys and apes, and includes species of monkeys such from the genus *Macaca* (e.g., cynomologus monkeys such as *Macaca fascicularis*, and/or rhesus monkeys (*Macaca mulatta*)) and baboon (*Papio ursinus*), as well as marmosets (species from the genus *Callithrix*), squirrel monkeys (species from the genus *Saimiri*) and tamarins (species from the genus *Saguinus*), as well as species of apes such as chimpanzees (*Pan troglodytes*)), rodents (e.g., mice, rats, guinea pigs), lagomorphs (e.g., rabbits, hares), bovines (e.g., cattle), ovines (e.g., sheep), caprines (e.g., goats), porcines (e.g., pigs), equines (e.g., horses), canines (e.g., dogs), felines (e.g., cats), avians (e.g., chickens, turkeys, ducks, geese, companion birds such as canaries, budgerigars), marine mammals (e.g., dolphins, whales), reptiles (e.g., snakes, frogs, lizards), and fish. In specific embodiments, the subject is a primate such as a human. However, it will be understood that the aforementioned terms do not imply that symptoms are present.

As used herein, the terms "prevent," "prevented," or "preventing," refer to a prophylactic treatment which increases the resistance of a subject to developing the disease or condition or, in other words, decreases the likelihood that the subject will develop the disease or condition as well as a treatment after the disease or condition has begun in order to reduce or eliminate it altogether or prevent it from becoming worse. These terms also include within their scope preventing the disease or condition from occurring in a subject which may be predisposed to the disease or condition but has not yet been diagnosed as having it.

Protein "expression" refers to conversion of the information encoded in a gene into messenger RNA (mRNA) and then to the protein. Herein, a sample or cell that "expresses" a protein of interest (e.g., a cell surface antigen such as EGRF) is one in which mRNA encoding the protein, or the protein, including fragments thereof, is determined to be present in the sample or cell.

The term "receptor" as used herein refers to a protein normally found on the surface of a cell (e.g., EGFR, VEGFR, FGFR, Her2/neu, CD20, etc.) which, when activated, leads to a signaling cascade in the cell.

As used herein, in the context of a cancer, the term "responder" refers to a patient who exhibits or is more likely to exhibit a beneficial clinical response following treatment with an EGFR antagonist. By contrast, the term "non-responder," as used herein, refers to a patient who is does not exhibit or is less likely to be exhibit a beneficial response following treatment with an EGFR antagonist. As used herein in the context of patient response to treatment with an EGFR antagonist, the terms "beneficial response," "beneficial patient response," and "clinically beneficial response," "clinical benefit," and the like, are used interchangeably and refer to favorable patient response to a drug as opposed to unfavorable responses, i.e., adverse events. In individual patients, beneficial response can be expressed in terms of a number of clinical parameters, including loss of detectable tumor (complete response, CR), decrease in tumor size and/or cancer cell number (partial response, PR), tumor growth arrest (stable disease, SD), enhancement of antitumor immune response, possibly resulting in regression or rejection of the tumor; relief, to some extent, of one or more symptoms associated with the tumor; increase in the length of survival following treatment; and/or decreased mortality at a given point of time following treatment. Continued increase in tumor size and/or cancer cell number and/or tumor metastasis is indicative of lack of beneficial response to treatment. Evaluation of patients in assessing symptoms and/or severity of the disease may be carried out by various methods, which are known in the art. The evaluation may take into account numerous criteria, as determined by suitable biochemical, physiological, and/or behavioral factors.

The term "reversible inhibitor", as used herein, refers to a compound that binds a target protein (e.g., a protein involved in receptor mediated endocytosis) with non-covalent interactions such as hydrogen bonds, hydrophobic interactions and ionic bonds. Multiple weak bonds between the inhibitor and the active site combine to produce strong and specific binding. In contrast to substrates and irreversible inhibitors, reversible inhibitors generally do not undergo chemical reactions when bound to the enzyme and can be easily removed by dilution or dialysis.

As used herein, the terms "treatment," "treating," and the like, refer to administering an agent, or carrying out a procedure (e.g., radiation, a surgical procedure, etc.) to obtain a desired pharmacologic and/or physiologic effect. The effect may be prophylactic in terms of completely or partially preventing a disease or symptom thereof and/or may be therapeutic in terms of effecting a partial or complete cure for a disease and/or symptoms of the disease. The effect may be therapeutic in terms of a partial or complete cure for a disease or condition (e.g., a cancer) and/or adverse effect attributable to the disease or condition. These terms also cover any treatment of a condition or disease in a mammal, particularly in a human, and include: (a) preventing the disease or a symptom of a disease from occurring in a subject which may be predisposed to the disease but has not yet been diagnosed as having it (e.g., including diseases that may be associated with or caused by a primary disease; (b) inhibiting the disease, i.e., arresting its development; (c) relieving the disease, i.e., causing regression of the disease; (d) reducing the severity of a symptom of the disease and/or (e) reducing the frequency of a symptom of the disease or condition.

The term "tumor," as used herein, refers to any neoplastic cell growth and proliferation, whether malignant or benign, and all pre-cancerous and cancerous cells and tissues. The terms "cancer" and "cancerous" refer to or describe the physiological condition in mammals that is typically characterized in part by unregulated cell growth and include As used herein, the term "cancer" refers to non-metastatic and metastatic cancers, including early stage and late stage cancers. The term "precancerous" refers to a condition or a growth that typically precedes or develops into a cancer. By "non-metastatic" is meant a cancer that is benign or that remains at the primary site and has not penetrated into the lymphatic or blood vessel system or to tissues other than the primary site. Generally, a non-metastatic cancer is any cancer that is a Stage 0, I, or II cancer, and occasionally a Stage III cancer. By "early stage cancer" is meant a cancer that is not invasive or metastatic or is classified as a Stage 0, I, or II cancer. The term "late stage cancer" generally refers to a Stage III or Stage IV cancer, but can also refer to a Stage II cancer or a substage of a Stage II cancer. One skilled in the art will appreciate that the classification of a Stage II cancer as either an early stage cancer or a late stage cancer depends on the particular type of cancer. Illustrative examples of cancer include, but are not limited to, colorectal cancer, breast cancer, ovarian cancer, lung cancer, prostate cancer, hepatocellular cancer, gastric cancer, pancreatic cancer, cervical cancer, liver cancer, bladder cancer, cancer of the urinary tract, thyroid cancer, renal cancer, carcinoma, melanoma, brain cancer, non-small cell lung cancer, squamous cell cancer of the head and neck, endometrial cancer, multiple myeloma, rectal cancer, and esophageal cancer. In an exemplary embodiment, the cancer is squamous cell carcinoma.

The term "tumor sample" as used herein means a sample comprising tumor material obtained from a cancerous patient. The term encompasses clinical samples, for example tissue obtained by surgical resection and tissue obtained by biopsy, such as for example a core biopsy or a fine needle biopsy. The term also encompasses samples comprising tumor cells obtained from sites other than the primary tumor, e.g., circulating tumor cells, as well as well as preserved tumor samples, such as formalin-fixed, paraffin-embedded tumor samples or frozen tumor samples. The term encompasses cells that are the progeny of the patient's tumor cells, e.g., cell culture samples derived from primary tumor cells or circulating tumor cells. The term encompasses samples that may comprise protein or nucleic acid material shed from tumor cells in vivo, e.g., bone marrow, blood, plasma, serum, and the like. The term also encompasses samples that have been enriched for tumor cells or otherwise manipulated after their procurement and samples comprising polynucleotides and/or polypeptides that are obtained from a patient's tumor material.

As used herein, the term "tumor associated antigen" or "TAA" refers to an antigen capable of expression by a tumor cell, or on cells of the same lineage as the tumor. The TAA in tumor may be expressed in amounts greater than normal relative to a non-tumor (normal) cell counterpart, or may be expressed at similar levels, or at levels less than normal cell counterparts, particularly if the gene encoding the TAA is down-modulated in the tumor cell. Tumor associated antigens are antigenic molecules whose expression facilitates interaction of immune cells or immune molecules (e.g., antibodies) with tumor cells. TAAs are molecules or portions of the molecules that immune targeting molecules (i.e., receptors on immune cells, antibodies, etc.) bind. As discussed, TAAs may be present in or on normal cells; tumor TAA expression may but need not deviate from normal (non-tumor) counterpart cells (e.g., a normal cell not expressing TAA, expressing less of the TAA than a tumor cell, or expressing the same or more TAA than tumor). However, TAA that are suitable in the practice of the present invention are expressed or are expressible on the surface the tumor cell (i.e., cell surface TAA) so that they are able to bind an antibody (e.g., a therapeutic antibody). A tumor associated antigen can be expressed during an earlier developmental or different differentiation stage of the cell; after progressing through the developmental stage, expression of the TAA is typically altered.

Each embodiment described herein is to be applied mutatis mutandis to each and every embodiment unless specifically stated otherwise.

2. Abbreviations

| Ab | Antibody |
|---|---|
| ADCC | Antibody Dependent Cellular Cytotoxicity |
| CDC | Complement Dependent Cytotoxicity |
| CDK | Cyclin Dependent Kinase |
| CR | Cysteine-Rich |
| EGF | Epidermal Growth Factor |
| EGFR | Epidermal Growth Factor Receptor |
| EGFRvIII | EGFR variant III |
| ER | Endoplasmic Reticulum |
| FACS | Fluorescence-Activated Cell Sorting |
| FcγR | Fcγ Receptor |
| FDA | Food and Drugs Administration |
| FISH | Fluorescence In Situ Hybridization |
| GPCR | G-Protein-Coupled Receptor |
| Grb2 | Growth Factor Receptor-Bound Protein 2 |
| HLA | Human Leukocyte Antigen |
| HNSCC | Head and Neck Squamous Cell Carcinoma |
| HUVEC | Human Umbilical Vascular Endothelial Cell |
| IF | Immunofluorescence |
| IHC | Immunohistochemistry |
| IL | Interleukin |
| mAb | Monoclonal Antibody |
| MAPK | Mitogen-Activated Protein Kinase |
| MHC | Major Histocompatibility Complex |
| NK | Natural Killer |
| OD | Optical Density |
| PBMC | Peripheral Blood Mononuclear Cell |
| PTB | Phosphtyrosine-Binding |
| PtdIns (4,5) $P_2$ | Phosphatidylinositol 4,5-Bisphosphate, also known as $PIP_2$ |
| RTK | Receptor Tyrosine Kinases |
| SCC | Squamous Cell Carcinoma |

3. Compositions for Stimulating an Enhanced Immune Response to a Tumor

The present invention provides compositions for stimulating an enhanced immune response including an enhanced antibody-dependent cellular cytotoxicity response to a tumor in a subject. These compositions generally employ (1) a therapeutic antibody that binds a cell surface antigen of the tumor, which antigen is subject to receptor mediated endocytosis, and (2) an inhibitor of receptor-mediated endocytosis.

3.1 Cell Surface Antigens and Antibodies

The cell surface antigen targeted by the antibody is suitably a tumor-associated antigen, illustrative examples of which include Her2/neu, EGFR, Epcam, VEGFR, MGFR, MUC-I, CA 125, CEA, MAGE, CD20, CD19, CD40, CD33, A3, antigen specific to A33 antibodies, BrE3 antigen, CD1, CD1a, CD5, CD8, CD14, CD15, CD16, CD21, CD22, CD23, CD30, CD33, CD37, CD38, CD40, CD45, CD46, CD52, CD54, CD74, CD79a, CD126, CD138, CD154, B7, Ia, Ii, HM1.24, HLA-DR (e.g., HLA-DR10), NCA95, NCA90, HCG and sub-units, CEA (CEACAM5), CEACAM-6, CSAp, EGP-I, EGP-2, Ba 733, KC4 antigen, KS-I antigen, KS1-4, Le-Y, MUC2, MUC3, MUC4, PIGF, ED-B fibronectin, NCA 66a-d, PAM-4 antigen, PSA, PSMA, RS5, S1OO, TAG-72, T1O1, TAG TRAIL-R1, TRAIL-R2, p53, tenascin, insulin growth factor-1 (IGF-I), Tn antigen etc.

Any suitable antibody that can be used in therapy and that binds the cell surface antigen expressed by the tumor is contemplated for use in the practice of the present invention. Non-limiting examples of such antibodies include: anti-EGFR antibodies such as but not limited to include MAb 579 (ATCC CRL HB 8506), MAb 455 (ATCC CRL HB8507), MAb 225 (ATCC CRL 8508), MAb 528 (ATCC CRL 8509) (see, U.S. Pat. No. 4,943,533, Mendelsohn et al.) and variants thereof, such as chimerized 225 (C225 or cetuximab; ERBITUX™) and reshaped human 225 (H225) (see, WO 96/40210, Imclone Systems Inc.); IMC-11F8, a fully human, EGFR-targeted antibody (Imclone); antibodies that bind type II mutant EGFR (U.S. Pat. No. 5,212,290); humanized and chimeric antibodies that bind EGFR as described in U.S. Pat. No. 5,891,996; and human antibodies that bind EGFR, such as ABX-EGF or panitumumab (see, WO98/50433, Abgenix/Amgen); EMD 55900 (Stragliotto et al. Eur. J. Cancer 32A:636-640 (1996)); EMD7200 (matuzumab) a humanized EGFR antibody directed against EGFR that competes with both EGF and TGF-α for EGFR binding (EMD/Merck); human EGFR antibody, HuMax-EGFR (GenMab); fully human antibodies known as E1.1, E2.4, E2.5, E6.2, E6.4, E2.11, E6.3 and E7.6.3 and described in U.S. Pat. No. 6,235,883; MDX-447 (Medarex Inc); and mAb 806 or humanized mAb 806 (Johns et al. (2004) *J. Biol. Chem.* 279(29):30375-30384); anti-HER2 antibodies, illustrative examples of which include HERCEPTIN™ (trastuzumab) (Genentech, Calif.); PANOREX™ which is a murine anti-17-IA cell surface antigen IgG2a antibody (Glaxo Wellcome/Centocor); BEC2 which is a murine anti-idiotype (GD3 epitope) IgG antibody (ImClone System); VITAXIN™ which is a humanized anti-αVβ3 integrin antibody (Applied Molecular Evolution/Medimmune); Campath 1H/LDP-03 which is a humanized anti CD52 IgG1 antibody (Leukosite); Smart M195 which is a humanized anti-CD33 IgG antibody (Protein Design Lab/Kanebo); RITUXAN™ (rituximab) which is a chimeric anti-CD20 IgG1 antibody (IDEC Pharm/Genentech, Roche/Zettyaku); LYMPHOCIDE™ which is a humanized anti-CD22 IgG antibody (Immunomedics); ICM3 is a humanized anti-ICAM3 antibody (ICOS Pharm); ZEVALIN™ is a radiolabelled murine anti-CD20 antibody (IDEC/Schering AG); and IDEC-152 (lumiliximab) is a primatized anti-CD23 antibody (IDEC/Seikagaku).

3.2 Inhibitors of Receptor-Mediated Endocytosis

Inhibitors of receptor mediated endocytosis contemplated by the present invention encompass any agent that inhibits or abrogates by any means endocytosis or internalization of a cell surface antigen to which a therapeutic antibody is directed. Suitably, the receptor mediated endocytosis inhibitor is a reversible receptor mediated endocytosis inhibitor. In specific embodiments, the receptor mediated endocytosis inhibitor is a clatlirin-dependent endocytosis inhibitor, illustrative examples of which include methyl-β-cyclodextrin (β-CD), hydrophobic amines (such as phenothiazines, monodansylcadaverine and chloroquine), monensin, hyperosmotic sucrose and dynasore. Phenothiazines include, but are not limited to, chlorpromazine, fluphenazine, mesoridazine, perphenazine, prochlorperazine, promazine, thioridazine, trifluoperazine and triflupromazine. β-CD inhibits clathrin-dependent endocytosis by selectively removing cholesterol from the plasma membrane. Hydrophobic amines inhibit clathrin-dependent endocytosis by affecting the function of clathrin and clathrin-coated vesicles. Monensin inhibits clathrin-dependent endocytosis by dissipating a proton gradient. Hyperosmotic sucrose inhibits clathrin-dependent endocytosis by preventing clathrin and adaptors from interacting. Dynasore inhibits dynamin GTPase which facilitates the formation of coated pits.

In specific embodiments, the receptor mediated endocytosis inhibitor is a dynamin-dependent endocytosis inhibitor. In non-limiting examples of this type, dynamin-dependent endocytosis inhibitor is a dynamin GTPase inhibitor, illustrative examples of which are selected from compounds described by McCluskey et al. in U.S. Pat. Appl. Pub. No. 2007/0225363, which is expressly incorporated herein by reference in its entirety. These compounds are represented by formula (I), or a physiologically acceptable salt thereof:

M-Sp-M'     (I)

wherein:

M and M' are each independently a moiety of formula II and are the same or different, and Sp is a spacer;

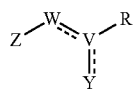
(II)

V is C or CH;

W is CH or a linker group; and

Y is hydrogen, cyano, nitro, NH, amino, oxo, halo, hydroxy, sulfhydryl, carboxy, thiocarboxy, sulfur, or an unsubstituted $C_1$-$C_3$ group or $C_1$-$C_3$ group substituted with at least one group independently selected from cyano, nitro, NH, amino, oxo, halo, hydroxy, sulfhydryl, carhoxy, thiocarboxy and sulfur; or W, V and Y form a 5 or 6 membered substituted or unsubstituted heterocyclic or carbocyclic ring fused with Z, wherein the heterocyclic ring includes from 1 to 3 heteroatoms selected from O, N and S, and the carbocyclic or heterocyclic ring, when substituted, has at least one substituent selected from cyano, nitro, NH, amino, oxo, halo, hydroxy, sulfhydryl, carboxy, thiocarboxy, sulfur, or an unsubstituted $C_1$-$C_3$ group or $C_1$-$C_3$ group substituted with at least one group independently selected from cyano, nitro, NH, amino, oxo, halo, hydroxy, sulfhydryl, carboxy, thiocarboxy and sulfur; and R is $CH_2R'$, CXR' or CHX'R;

X is O or S;

X' is cyano, nitro, amino, halo, hydroxy, sulfhydryl, carboxy, thiocarboxy, or an unsubstituted $C_1$-$C_3$ group or $C_1$-$C_3$ group substituted with at least one group independently selected from cyano, nitro, NH, amino, oxo, halo, hydroxy, sulfhydryl, carboxy, thiocarboxy and sulfur;

R' is NH, O or S bonded to the spacer; and

Z is selected from:

(a) an unsubstituted heterocyclic group consisting of one or two rings independently having 5 or 6 ring members including up to 3 heteroatoms selected from O, N and S;

(b) an unsubstituted carbocyclic group consisting of one or two rings independently having 5 or 6 ring members;

(c) a heterocyclic group consisting of one or two rings independently having 5 or 6 ring members including up to 3 heteroatoms selected from O, N and S wherein, the heterocyclic group has one or more substituents independently selected from:

(i) nitro, NH, amino, cyano, halo, hydroxy, carboxy, oxo, sulfur, sulfhydryl, $C_1$-$C_2$ alkoxy and $C_1$-$C_2$ acyl; and (ii) a $C_1$-$C_2$ alkyl or $C_1$-$C_2$ alkenyl group with at least one substituent selected from nitro. NH, amino, cyano, halo, hydroxy, carboxy, oxo, sulfur, sulfhydryl, $C_1$-$C_2$ alkoxy and $C_1$-$C_2$ acyl; and (d) a carbocyclic group consisting of one or two rings independently having 5 or 6 ring members, and at least two substituents when W is CH or a linker group or W, V and Y form an unsubstituted carbocyclic group, or at least one substituent when W, V and Y form a heterocyclic group, independently selected from:

(i) nitro, NH, amino, cyano, halo, hydroxy, carboxy, oxo, sulfur, sulfhydryl, $C_1$-$C_2$ alkoxy and $C_1$-$C_2$ acyl; and (ii) a $C_1$-$C_2$ alkyl or $C_1$-$C_2$ alkenyl group with at least one substituent selected from nitro, NH, amino, cyano, halo, hydroxy, carboxy, oxo, sulfur, sulfhydryl, $C_1$-$C_2$ alkoxy and $C_1$-$C_2$ acyl; and wherein when Z of one of M or M' is selected from (b), Z of the other of M or M' is selected from (a), (c) or (d).

In specific embodiments, the compound of formula I is a dimeric tyrphostin.

In other embodiments, the dynamin-dependent endocytosis inhibitor is selected from dynamin ring stabilizers, which inhibit dynamin ring disassembly thereby prolonging dynamin ring lifetime and promoting dynamin ring accumulation. Exemplary dynamin ring stabilizers are disclosed for example by Robinson et al. in U.S. Pat. Appl. Pub. No. 2012/0122968, which is expressly incorporated herein by reference in its entirety. Representative compounds disclosed by Robinson et al. are selected from helical dynamin GTPase inhibitors, dimeric tyrphostins, dimeric benzylidenemalonitrile tyrphostins, iminochromenes, monomeric tyrphostins and 3-substituted naphthalene-2-carboxylic acid (benzylidene) hydrazides, non limiting examples of which include:

Bis-tyrphostin-22 (Bis-T-22), which is a dimeric tyrphostin and is a potent in vitro inhibitor of dynamin when dynamin is activated by phosphatidylserine (PS) liposomes to assemble into a flexible helix. In the absence of PS liposomes, dynamin can only assemble into single rings. Surprisingly, while Bis-T-22 inhibits the activity of helical dynamin it also uniquely, simultaneously stimulates basal dynamin GTPase activity by preventing disassembly of dynamin rings. The structure of Bis-T-22 is shown below. Bis-T has the same structure as Bis-T-22 but has an additional hydroxyl substituent on the C5 carbon atom of each terminal phenyl group.

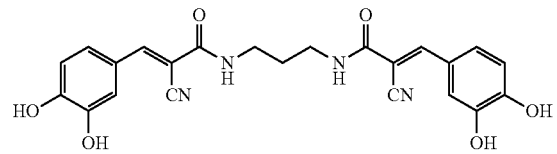 [SMILES: N#C/C(=C\c1ccc(O)c(O)c1)C(=O)NCCCNC(=O)/C(C#N)=C/c1ccc(O)c(O)c1]

Structure of Bis-Tyrphostin (Bis-T-22)

Particularly suitable dimeric tyrphostins useful as dynamin ring stabilizers include those Bis-T compounds in which two of the C3-C5 carbon atoms of at least one terminal phenyl ring have hydroxyl (OH) substituents, suitably in a catechol arrangement (e.g., as in Bis-T-22), or all three of the carbon atoms are substituted with hydroxyl (e.g., as in Bis-T-23). Illustrative examples of such compounds include 2-cyano-N-{3-[2-cyano-3-(3,4-dihydroxyphenyl)-acryloylamino]-ethyl}-3-(3,-4-dihydroxyphenyl)-acrylamide, 2-cyano-N-{3-[2-cyano-3-(3,4,5-trihydroxyphenyl)-acryloylamino]-ethyl}-3-(3,4,5-trihydroxyphenyl)-acrylamide, 2-cyano-N-{3-[2-cyano-3-(3,4-dihydroxy-4-methoxyphenyl)-acryloylamino]-ethyl}-3-(3,4-dihydroxy-5-methoxyphenyl)-acrylamide, 2-cyano-N-{3-[2-cyano-3-(3,4-dihydroxyphenyl)-acryloylamino]-propyl}-3-(3-,4-dihydroxyphenyl)-acrylamide (Bis-T-22), 2-cyano-N-{3-[2-cyano-3-(3,4,5-trihydroxyphenyl)-acryloylamino]-propyl}-3-(3,4,5-trihydroxyphenyl)-acrylamide (Bis-T-23), 2-cyano-N-{3-[2-cyano-3-(3,4-dihydroxy-5-methoxyphenyl)-acryloylamino]-propyl}-3-(3,4-dihydroxy-5-methoxyphenyl)-acrylamide, 2-cyano-N-{3-[2-cyano-3-(3,4-dihydroxyphenyl)-acryloylamino]-butyl}-3-(3,-4-dihydroxyphenyl)-acrylamide, 2-cyano-N-{3-[2-cyano-3-(3,4,5-trihydroxyphenyl)-acryloylamino]-butyl}-3-(3,4,5-trihydroxyphenyl)-acrylamide, 2-cyano-N-{3-[2-cyano-3-(3,4-dihydroxy-5-methoxyphenyl)-acryloylamino]-butyl}-3-(3,4-dihydroxy-5-methoxyphenyl)-acrylamide, 2-cyano-N-{3-[2-cyano-3-(3,4-dihydroxyphenyl)-acryloylamino]-pentyl}-3-(3-,4-dihydroxyphenyl)-acrylamide, 2-cyano-N-{3-[2-cyano-3-(3,4,5-trihydroxyphenyl)-acryloylamino]-pentyl}-3-(3,4,5-trihydroxyphenyl)-acrylamide, 2-cyano-N-{3-[2-cyano-3-(3,4-dihydroxy-5-methoxyphenyl)-acryloylamino]-pentyl}-3-(3,4-dihydroxy-5-methoxyphenyl)-acrylamide, 2-cyano-N-{3-[2-cyano-3-(3,4-dihydroxyphenyl)-acryloylamino]-hexyl}-3-(3,-4-dihydroxyphenyl)-acrylamide, 2-cyano-N-{3-[2-cyano-3-(3,4,5-trihydroxyphenyl)-acryloylamino]-hexyl}-3-(3,4,5-trihydroxyphenyl)-acrylamide, and 2-cyano-N-{3-[2-cyano-3-(3,4-dihydroxy-5-methoxyphenyl)-acryloylamino]-hexyl}-3-(3,4-dihydroxy-5-methoxyphenyl)-acrylamide.

Further dynamin ring stabilizers include those in which a substituent on the C2 carbon atom of at least one terminal phenyl ring of a Bis-T compound and the position occupied by an adjacent cyanyl group (CN) are cyclized as described in WO 2005/049009, which is incorporated by reference herein in its entirety. For instance, when the substituent is hydroxy, the hydroxy group can react with the cyanyl group to form an iminochromene as follows:

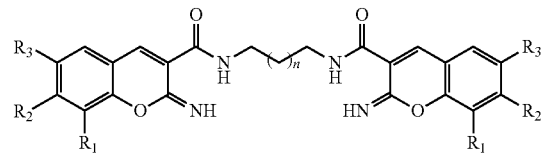

where for example, $R_1$ is OH, $R_2$ is OH and $R_3$ is H; $R_1$ is H, $R_2$ is OH and $R_3$ is OH; or $R_1$, $R_2$ and $R_3$ are OH; and n is usually 0, 1, 2 or 3, and most usually 1.

Other non-limiting examples of dynamin ring stabilizers disclosed by Robinson et al. include 3-hydroxynaphthalene-2-carboxylic acid (3,4-dihydroxybenzylidene) hydrazide (dynasore) and analogs thereof. The structure for dynasore is as follows

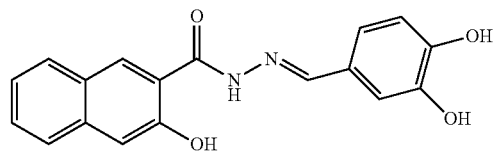

Structure of Dynasore

Examples of further 3-substituted naphthalene-2-carboxylic acid (benzylidene) hydrazide analogs of dynasore (named Dyngo compounds) are disclosed by Robinson et al., which are described as exhibiting improved dynamin inhibitory potency, as compared to dynasore. These analogs are shown in the following are shown in Table A below.

TABLE A

| | DYNGO COMPOUNDS | | | |
|---|---|---|---|---|
| Compound | Structure | MW (g/mol) | IC$_{50}$ (µM) | IC$_{50}$ (µM) |
| Dynasore (Dyngo-7a) | | | Full-length Dyn I (7 nM, 2 µg/mol PS) With tween 80 | Full-length Dyn I (7 nM, 2 µg/mol PS) With tween 80 |
| Dyngo-4a | | 338.32 | 2.7 ± 0.7 | 0.31 ± 0.05 |
| Dyngo-6a | | 322.31 | 19.8 | 22.1 |

TABLE A-continued

DYNGO COMPOUNDS

| Compound | Structure | MW (g/mol) | IC$_{50}$ (μM) | IC$_{50}$ (μM) |
|---|---|---|---|---|
| Dyngo-1a | 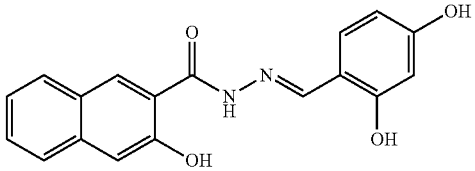 [SMILES: O=C(N/N=C/c1ccc(O)cc1O)c1cc2ccccc2cc1O] | 322.31 | 200 | 37.3 |
| Dyngo-5a | 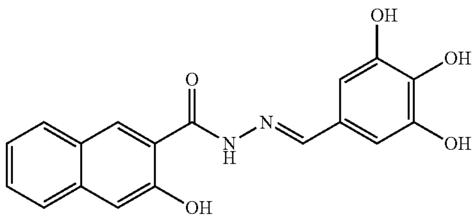 [SMILES: O=C(N/N=C/c1cc(O)c(O)c(O)c1)c1cc2ccccc2cc1O] | 338.32 | ~468 | 4.4 |
| Dyngo-2a | 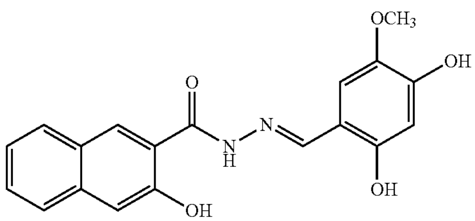 [SMILES: COc1cc(/C=N/NC(=O)c2cc3ccccc3cc2O)c(O)cc1O] | 352.35 | 1170 | 3.6 |
| Dyngo-3a | 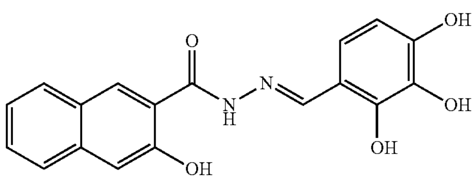 [SMILES: O=C(N/N=C/c1ccc(O)c(O)c1O)c1cc2ccccc2cc1O] | 338.32 | Not Active | 31. |
| Dyngo-8a | 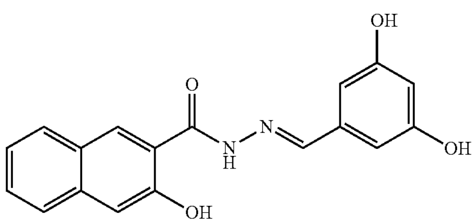 [SMILES: O=C(N/N=C/c1cc(O)cc(O)c1)c1cc2ccccc2cc1O] | 322.31 | Not Active | 39.8 |

Further dynamin ring stabilizers are disclosed by Robinson et al., which are also encompassed by the present invention for inhibiting receptor mediated endocytosis, including clathrin-dependent receptor mediated endocytosis and a dynamin-dependent receptor-mediated endocytosis.

The invention not only encompasses known inhibitors of receptor-mediated endocytosis (e.g., clathrin-dependent endocytosis inhibitors, dynamin-dependent endocytosis inhibitors, etc.) but receptor-mediated endocytosis inhibitors identified by any suitable screening assay. Accordingly, the present invention extends to methods of screening for modulatory agents that are useful for inhibiting receptor-mediated endocytosis and, in turn, for enhancing the antibody-dependent cellular cytotoxicity response to a tumor having a cell surface receptor that is subject to receptor-mediated endocytosis (e.g., EGFR, VEGFR, FGFR, Her/neu2, CD20 etc.). In some embodiments, the screening methods comprise (1) contacting a preparation with a test agent, wherein the preparation comprises (i) a polypeptide comprising an amino acid sequence corresponding to at least a biologically active fragment of a dynamin polypeptide (e.g., a dynamin polypeptide comprising an amino acid sequence as set forth for example in GenBank Accession No. AAA88025); or (ii) a polynucleotide comprising a nucleotide sequence from which a transcript of a dynamin gene (e.g., a dynamin gene comprising a nucleotide sequence as set forth for example in GenBank Accession No. L36983) or portion thereof is producible, or (iii) a polynucleotide comprising at least a portion of a genetic sequence (e.g., a promoter) that regulates the expression of a dynamin gene, which is operably linked to a reporter gene; and (2) detecting a change in the level or functional activity of the polypeptide, the polynucleotide or an expression product of the reporter gene, relative to a reference level or functional activity in the absence of the test agent. A detected reduction in the level and/or functional activity of the polypeptide, transcript or transcript portion or an expression product of the reporter gene, relative to a normal or reference level and/or functional activity in the absence of the test agent, indicates that the agent is a dynamin inhibitor and potentially useful for enhancing the antibody-dependent cellular cytotoxicity response to a tumor having a cell surface receptor that is subject to receptor-mediated endocytosis (e.g., EGFR, VEGFR, FGFR, Her/neu2, CD20 etc.). Suitably, this is confirmed by analyzing or determining whether the test agent enhances the antibody-dependent cellular cytotoxicity response to a tumor having a cell surface receptor that is subject to receptor-mediated endocytosis (e.g., EGFR, VEGFR, FGFR, Her/neu2, CD20 etc.), optionally in combination with an antibody to the cell surface receptor.

In specific embodiments, inhibitors of receptor-mediated endocytosis are identified by methods that assay dynamin ring stabilization, as described for example by McCluskey et al. (supra) and which is incorporated herein by reference in its entirety. These methods generally comprise incubating a test agent with a dynamin polypeptide (e.g., a dynamin polypeptide comprising an amino acid sequence as set forth for example in GenBank Accession No. AAA88025, or biologically active fragment thereof) under conditions suitable for the formation of dynamin rings; and evaluating whether the test agent promotes accumulation of dynamin rings and/or inhibits disassembly of dynamin rings, the accumulation of dynamin rings and/or inhibition of disassembly of dynamin rings increasing basal dynamin GTPase activity. The evaluation of whether the test agent promotes the accumulation of dynamin rings or inhibits disassembly of dynamin rings can involve assaying for an increase in basal dynamin GTPase activity, and/or release of dynamin that is indicative of dynamin ring disassembly.

Modulators falling within the scope of the present invention include inhibitors of receptor-mediated endocytosis (e.g., clathrin-dependent endocytosis inhibitors, dynamin-dependent endocytosis inhibitors, etc.), including antagonistic antibodies, antibody fragments, inhibitory peptide fragments, antisense molecules, ribozymes, RNAi molecules and co-suppression molecules as well as polysaccharide and lipopolysaccharide inhibitors of a polypeptides that mediate receptor-mediated endocytosis (e.g., clathrin, dynamin, etc.).

Candidate agents encompass numerous chemical classes, though typically they are organic molecules, preferably small organic compounds having a molecular weight of more than 50 and less than about 2,500 Dalton. Candidate agents comprise functional groups necessary for structural interaction with proteins, particularly hydrogen bonding, and typically include at least an amine, carbonyl, hydroxyl or carboxyl group, desirably at least two of the functional chemical groups. The candidate agent often comprises cyclical carbon or heterocyclic structures or aromatic or polyaromatic structures substituted with one or more of the above functional groups. Candidate agents are also found among biomolecules including, but not limited to: peptides, saccharides, fatty acids, steroids, purines, pyrimidines, derivatives, structural analogues or combinations thereof.

Small (non-peptide) molecule inhibitors of receptor-mediated endocytosis (e.g., a clathrin-dependent endocytosis inhibitor, a dynamin-dependent endocytosis inhibitor, etc.) are particularly advantageous. In this regard, small molecules are desirable because such molecules are more readily absorbed after oral administration, have fewer potential antigenic determinants, or are more likely to cross the cell membrane than larger, protein-based pharmaceuticals. Small organic molecules may also have the ability to gain entry into an appropriate cell and affect the expression of a gene (e.g., by interacting with the regulatory region or transcription factors involved in gene expression); or affect the activity of a gene by inhibiting or enhancing the binding of accessory molecules.

Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogues.

Screening may also be directed to known pharmacologically active compounds and chemical analogues thereof.

Compounds may be further tested in the animal models to identify those compounds having the most potent in vivo effects. These molecules may serve as "lead compounds" for the further development of pharmaceuticals by, for example, subjecting the compounds to sequential modifications, molecular modeling, and other routine procedures employed in rational drug design.

Generally, the inhibitor of receptor mediated endocytosis and therapeutic antibody (also referred to herein collectively as "therapeutic agents") are administered in the form of pharmaceutical compositions that optionally comprise a pharmaceutically acceptable carrier, excipient and/or stabilizer (Remington's Pharmaceutical Sciences 16th edition, Osol, A. Ed. (1980)). These compositions are generally in the form of lyophilized formulations or aqueous solutions. Antibody crystals are also contemplated (see, U.S. Pat. Appl. 2002/0136719). Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). Lyophilized antibody formulations are described in WO 97/04801.

The pharmaceutical compositions contain the active compounds as necessary for the particular indication being treated, desirably those with complementary activities that do not adversely affect each other. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nanoparticles and nanocapsules)

or in macroemulsions. Such techniques are disclosed in Remington's Pharmaceutical Sciences 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and .gamma. ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(–)-3-hydroxybutyric acid.

The compositions of the present invention are thus suitable for treating an individual who has been diagnosed with a cancer, who is suspected of having a cancer, who is known to be susceptible and who is considered likely to develop a cancer, or who is considered likely to develop a recurrence of a previously treated cancer.

In some embodiments, and dependent on the intended mode of administration, the compositions will generally contain about 0.000001% to 90%, about 0.0001% to 50%, or about 0.01% to about 25%, by weight of receptor mediated endocytosis inhibitor, the remainder being the therapeutic antibody and suitable pharmaceutical carriers or diluents etc. In some embodiments, and dependent on the intended mode of administration, the compositions will generally contain about 0.000001% to 90%, about 0.0001% to 50%, or about 0.01% to about 25%, by weight of therapeutic antibody, the remainder being the receptor mediated endocytosis inhibitor and suitable pharmaceutical carriers or diluents etc. The dosage of the receptor mediated endocytosis inhibitor and therapeutic antibody can depend on a variety of factors, such as mode of administration, the species of the affected subject, age, sex, weight and general health condition, and can be easily determined by a person of skill in the art using standard protocols. The dosages will also take into consideration the binding affinity of the receptor mediated endocytosis inhibitor and therapeutic antibody to their target molecules, their bioavailability and their in vivo and pharmacokinetic properties. In this regard, precise amounts of the agents for administration can also depend on the judgment of the practitioner. In determining the effective amount of the agents to be administered in the treatment or prevention of a hyperproliferative cell disorder, the physician or veterinarian may evaluate the progression of the disease or condition over time. In any event, those of skill in the art may readily determine suitable dosages of the agents of the invention without undue experimentation. The dosage of the actives administered to a patient should be sufficient to effect a beneficial response in the patient over time such as impairment or abrogation in the proliferation, migration, invasion, survival or viability of hyperproliferative cells and/or in the treatment and/or prevention of a hyperproliferative cell disorder. The dosages may be administered at suitable intervals to ameliorating the symptoms of the hematologic malignancy. Such intervals can be ascertained using routine procedures known to persons of skill in the art and can vary depending on the type of active agent employed and its formulation. For example, the interval may be daily, every other day, weekly, fortnightly, monthly, bimonthly, quarterly, half-yearly or yearly.

For any compound used in the methods of the invention, the therapeutically effective dose can be estimated initially from cell culture assays. For example, a dose can be formulated in animal models to achieve a circulating concentration range that includes the IC50 as determined in cell culture (e.g., the concentration of an inhibitor of receptor mediated endocytosis, which achieves a half-maximal inhibition in ligand induced cell surface antigen internalization). Such information can be used to more accurately determine useful doses in mammals, including humans.

Dosage amount and interval may be adjusted individually to provide plasma levels of the active agent, which are sufficient to maintain receptor mediated endocytosis-inhibitory effects and/or to maintain therapeutic antibody effects. Usual patient dosages for systemic administration range from 1-2000 mg/day, commonly from 1-250 mg/day, and typically from 10-150 mg/day. Stated in terms of patient body weight, usual dosages range from 0.02-25 mg/kg/day, commonly from 0.02-3 mg/kg/day, typically from 0.2-1.5 mg/kg/day. Stated in terms of patient body surface areas, usual dosages range from 0.5-1200 mg/m$^2$/day, commonly from 0.5-150 mg/m$^2$/day, typically from 5-100 mg/m$^2$/day.

It is conceivable that more than one administration of either receptor mediated endocytosis inhibitor and/or therapeutic antibody will be desired. Various combinations may be employed, where the receptor mediated endocytosis inhibitor is "A" and the therapeutic antibody is "B", as exemplified below:

A/B/A B/A/B B/B/A A/A/B B/A/A A/A/B B/B/B/A BIB/ A/B A/A/B/B A/B/A/B A/B/B/A B/B/A/A B/A/B/A B/A/ A/B B/B/B/A A/A/A/B B/A/A/A A/B/A/A A/A/B/A A/B/ BIB B/A/B/B B/B/A/B.

Other combinations are contemplated. Again, both agents are delivered to a subject in a combined amount effective to enhance an immune response to a cancer or tumor as compared to the administration of the same amount of therapeutic antibody alone.

The receptor mediated endocytosis inhibitor and therapeutic antibody may be administered concurrently with at least one ancillary therapy that treats or ameliorates the symptoms or reverses or inhibits the development or progression of a cancer in a subject. The inhibitor and antibody may be used therapeutically after the ancillary therapy or may be used before the therapy is administered or together with the therapy. Accordingly, the present invention contemplates combination therapies, which employ a receptor mediated endocytosis inhibitor, therapeutic antibody and concurrent administration of an ancillary therapy (e.g., medical treatment), non-limiting examples of which include radiotherapy, surgery, chemotherapy, hormone ablation therapy, pro-apoptosis therapy and immunotherapy.

3.3 Radiotherapy

Radiotherapies include radiation and waves that induce DNA damage for example, γ-irradiation, X-rays, UV irradiation, microwaves, electronic emissions, radioisotopes, and the like. Therapy may be achieved by irradiating the localized tumor site with the above described forms of radiations. It is most likely that all of these factors effect a broad range of damage DNA, on the precursors of DNA, the replication and repair of DNA, and the assembly and maintenance of chromosomes.

Dosage ranges for X-rays range from daily doses of 50 to 200 roentgens for prolonged periods of time (3 to 4 weeks), to single doses of 2000 to 6000 roentgens. Dosage ranges for radioisotopes vary widely, and depend on the half life of the isotope, the strength and type of radiation emitted, and the uptake by the neoplastic cells.

Non-limiting examples of radiotherapies include conformal external beam radiotherapy (50-100 Grey given as fractions over 4-8 weeks), either single shot or fractionated, high dose rate brachytherapy, permanent interstitial brachytherapy, systemic radio-isotopes (e.g., Strontium 89). In some embodiments the radiotherapy may be administered in combination with a radiosensitizing agent. Illustrative examples of radiosensitizing agents include but are not limited to efaproxiral, etanidazole, fluosol, misonidazole, nimorazole, temoporfin and tirapazamine.

3.4 Chemotherapy

Chemotherapeutic agents may be selected from any one or more of the following categories:

(i) antiproliferative/antineoplastic drugs and combinations thereof, as used in medical oncology, such as alkylating agents (e.g., cis-platin, carboplatin, cyclophosphamide, nitrogen mustard, melphalan, chlorambucil, busulphan and nitrosoureas); antimetabolites (e.g., antifolates such as fluoropyridines like 5-fluorouracil and tegafur, raltitrexed, methotrexate, cytosine arabinoside and hydroxyurea; anti-tumor antibiotics (e.g., anthracyclines like adriamycin, bleomycin, doxorubicin, daunomycin, epirubicin, idarubicin, mitomycin-C, dactinomycin and mithramycin); antimitotic agents (e.g., vinca alkaloids like vincristine, vinblastine, vindesine and vinorelbine and taxoids like paclitaxel and docetaxel; and topoisomerase inhibitors (e.g., epipodophyllotoxins like etoposide and teniposide, amsacrine, topotecan and camptothecin);

(ii) cytostatic agents such as antioestrogens (e.g., tamoxifen, toremifene, raloxifene, droloxifene and iodoxyfene), oestrogen receptor down regulators (for example fulvestrant), antiandrogens (e.g., bicalutamide, flutamide, nilutamide and cyproterone acetate), UH antagonists or LHRH agonists (e.g., goserelin, leuprorelin and buserelin), progestogens (e.g., megestrol acetate), aromatase inhibitors (e.g., as anastrozole, letrozole, vorazole and exemestane) and inhibitors of 5α-reductase such as finasteride;

(iii) agents which inhibit cancer cell invasion (e.g., metalloproteinase inhibitors like marimastat and inhibitors of urokinase plasminogen activator receptor function);

(iv) inhibitors of growth factor function, for example such inhibitors include growth factor antibodies, growth factor receptor antibodies (e.g., the anti-erbb2 antibody trastuzumab [Herceptin™] and the anti-erbb1 antibody cetuximab [C225]), famesyl transferase inhibitors, MEK inhibitors, tyrosine kinase inhibitors and serine/threonine kinase inhibitors, for example other inhibitors of the epidermal growth factor family (for example other EGFR family tyrosine kinase inhibitors such as N-(3-chloro-4-fluorophenyl)-7-methoxy-6-(3-morpholinopropoxy)quinazolin-4-amine (gefitinib, AZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)quinazoli-n-4-amine (CI 1033)), for example inhibitors of the platelet-derived growth factor family and for example inhibitors of the hepatocyte growth factor family;

(v) anti-angiogenic agents such as those which inhibit the effects of vascular endothelial growth factor, (e.g., the anti-vascular endothelial cell growth factor antibody bevacizumab [Avastin™], compounds such as those disclosed in International Patent Applications WO 97/22596, WO 97/30035, WO 97/32856 and WO 98/13354) and compounds that work by other mechanisms (e.g., linomide, inhibitors of integrin αvβ3 function and angiostatin);

(vi) vascular damaging agents such as Combretastatin A4 and compounds disclosed in International Patent Applications WO 99/02166, WO00/40529, WO 00/41669, WO01/92224, WO02/04434 and WO02/08213;

(vii) antisense therapies, for example those which are directed to the targets listed above, such as ISIS 2503, an anti-ras antisense; and (viii) gene therapy approaches, including for example approaches to replace aberrant genes such as aberrant p53 or aberrant. GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy.

3.5 Immunotherapy

Immunotherapy approaches, include for example ex-vivo and in-vivo approaches to increase the immunogenicity of patient tumor cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumor cell lines and approaches using anti-idiotypic antibodies. These approaches generally rely on the use of immune effector cells and molecules to target and destroy cancer cells. The immune effector may be, for example, an antibody specific for some marker on the surface of a malignant cell. The antibody alone may serve as an effector of therapy or it may recruit other cells to actually facilitate cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a malignant cell target. Various effector cells include cytotoxic T cells and NK cells.

3.6 Other Therapies

Examples of other cancer therapies include phototherapy, cryotherapy, toxin therapy or pro-apoptosis therapy. One of skill in the art would know that this list is not exhaustive of the types of treatment modalities available for cancer and other hyperplastic lesions.

4. Methods of Classifying Tumors and Stratifying Subjects According to that Classification The present invention also contemplates the use of methods of classifying tumors into therapeutic antibody sensitive and therapeutic antibody resistant subtypes in order to better manage a subject that is a non-responder to the therapeutic antibody. In accordance with the present invention, these classification methods involve analyzing the ligand-induced cell surface antigen (e.g., receptor) internalization status of the tumor. A detected ligand-induced cell surface antigen internalization that is impaired or abrogated relative to a control (e.g., a normal cell surface antigen-expressing cell) classifies the tumor as therapeutic antibody sensitive, whereas a detected ligand-induced cell surface antigen internalization that is the same as, similar to, or even greater than the control classifies the tumor as therapeutic antibody resistant. In some embodiments, impaired ligand-induced cell surface antigen internalization is indicated when, suitably after at least 10 minutes (e.g., 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or more minutes) in the presence of a ligand to the cell surface antigen: (a) at least 90% (e.g., 90%, 91%, 92%, 93%, 94%, 95%, 96%, 97%, 98%, 99% or 100%) of the EGFR in cell surface antigen-expressing cells of the tumor is localized or remains localized to the plasma membrane (e.g., basolateral membrane) of the cells; (b) the ratio of cell surface antigen localized to the plasma membrane of cell surface antigen-expressing cells of the tumor to cell surface antigen localized in the intracellular compartments of those cells (e.g., cytoplasm, nucleus etc.) is selected from 90:10, 91:9, 92:8, 93:7, 94:6, 95:5, 96:4, 97:3, 98:2, 99:1 or 100:0; or (c) the degree or quantum of ligand-induced cell surface antigen internalization in cell surface antigen-expressing cells of the tumor is less than 10%, 9%, 8%, 7%, 6%, 5%, 4%, 3%, 2%, 1% of the degree or quantum of ligand-induced cell surface antigen internalization in cell surface antigen-expressing normal cells.

In some embodiments, unimpaired ligand-induced cell surface antigen internalization is indicated when, suitably after at least 10 minutes (e.g., 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or more minutes) in the presence of a ligand to the cell surface antigen: (a) less than 100% (e.g., 99%, 98%, 97%, 96%, 95%, 94%, 93%, 92%, 91%, 90%, 85%, 80%, 75%, 70%, 65%, 60%, 55%, 50%, 45%, 40%, 35%, 30%, 25%, 20%, 15%, 10%, 5% or even less) of the cell surface antigen in cell surface antigen-expressing cells of the tumor is localized or remains localized to the plasma membrane (e.g., basolateral membrane) of the cells; (b) the ratio of cell surface antigen localized to the plasma membrane of cell surface antigen-expressing cells of the tumor to cell surface antigen localized in the intracellular compartments of those cells (e.g., cytoplasm, nucleus etc.) is selected from 99:1; 98:2, 97:3, 96:4, 95:5, 94:6, 93:7, 92:8, 91:9, 90:10, 85:15, 80:20, 75:25, 70:30, 65:35, 60:40, 55:45, 50:50, 45:55, 40:60, 35:65; 30:70, 25:75, 20:80, 15:85, 10:90, 5:95 or 0:100; (c) the degree or quantum of ligand-induced cell surface antigen internalization in cell surface antigen-expressing cells of the tumor varies by less than 10%, 9%, 8%, 7%, 6%, 5%, 4%, 3%, 2% or 1% as compared to the degree or quantum of ligand-induced cell surface antigen internalization in cell surface antigen-expressing normal cells; or (d) the degree or quantum of ligand-induced cell surface antigen internalization in cell surface antigen-expressing cells of the tumor is greater than the degree or quantum of ligand-induced cell surface antigen internalization in cell surface antigen-expressing normal cells.

In some embodiments, the methods comprise: (a) providing a tumor sample comprising one or a plurality of cell surface antigen-expressing tumor cells or putative cell surface antigen-expressing tumor cells, (b) contacting the tumor cell(s) with a labeled ligand to the cell surface antigen to form a labeled complex comprising the cell surface antigen and the labeled ligand, and (c) monitoring ligand-induced cell surface antigen internalization in the tumor cells by detecting cellular location of the labeled complex. Typically, the methods further comprise determining the degree of ligand-induced cell surface antigen internalization by comparing the amount of labeled complex bound to the surface of the tumor cells and the amount of labeled complex inside the tumor cells (e.g., intracellular compartment of the tumor cells including, but not limited to, cytoplasm, nucleus, endosomes, etc.). In some embodiments, ligand-induced cell surface antigen internalization is detected by qualitatively or quantitatively detecting a decrease of labeled complex on the surface of the tumor cells and/or qualitatively or quantitatively detecting an increase of labeled complex inside the tumor cells. Usually, ligand-induced cell surface antigen internalization in the tumor cells is monitored for at least 10 and less than 60 minutes, usually for at least 20 and less than 40 minutes.

Generally, the methods further comprise providing a control sample comprising one or a plurality of cell surface antigen-expressing control cells (e.g., normal cells), (b) contacting the control cell(s) with a labeled ligand to the cell surface antigen, which is generally the same as the one used for contacting the tumor cells, to form a labeled complex comprising the cell surface antigen and the labeled ligand, and (c) monitoring ligand-induced cell surface antigen internalization in the control cells by detecting cellular location of the labeled complex. Typically, these methods further comprise determining the degree of ligand-induced cell surface antigen internalization by comparing the amount of labeled complex bound to the surface of the control cells and the amount of labeled complex inside the control cells (e.g., intracellular compartment of the tumor cells including, but not limited to, cytoplasm, nucleus, endosomes, etc.). Usually, ligand-induced cell surface antigen internalization in the control cells is monitored for the same time employed for the tumor cells.

In some embodiments, the degree or amount of ligand-induced cell surface antigen internalization in the control cells is compared with the degree or amount of ligand-induced cell surface antigen internalization in the tumor cells to determine whether the tumor cells have impaired or unimpaired ligand-induced cell surface antigen internalization. In illustrative examples of this type, impaired ligand-induced cell surface antigen internalization in the tumor cells is determined when the ligand-induced cell surface antigen internalization in the tumor cells is less than 10%, 9%, 8%, 7%, 6%, 5%, 4%, 3%, 2%, 1% of the degree or quantum of ligand-induced cell surface antigen internalization in cell surface antigen-expressing normal cells. In other illustrative examples, unimpaired ligand-induced cell surface antigen internalization in the tumor cells is determined when the degree or quantum of ligand-induced cell surface antigen internalization in cell surface antigen-expressing cells of the tumor varies by less than 10%, 9%, 8%, 7%, 6%, 5%, 4%, 3%, 2% or 1% as compared to the degree or quantum of ligand-induced cell surface antigen internalization in cell surface antigen-expressing normal cells; or the degree or quantum of ligand-induced cell surface antigen internalization in cell surface antigen-expressing cells of the tumor is greater than the degree or quantum of ligand-induced cell surface antigen internalization in cell surface antigen-expressing normal cells.

In some embodiments, the methods further comprise obtaining the tumor sample from a subject with a cancer, suitably a cell surface antigen positive cancer. The sample may, for example, be a fresh biopsy sample, a fixed sample, e.g. a formalin fixed, paraffin-embedded (FFPE) sample, or a frozen sample. Non-limiting examples of cell surface antigen positive cancers include squamous cell carcinoma (e.g., epithelial squamous cell carcinoma), lung cancer including small-cell lung cancer (SCLC), non-small cell lung cancer (NSCLC), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer (including metastatic breast cancer), colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, testicular cancer, esophageal cancer, tumors of the biliary tract, as well as head and neck cancer. The tumor may be a metastatic or non-metastatic tumor.

Suitably, the methods further comprise classifying the tumor as a therapeutic antibody sensitive tumor if the detected ligand-induced cell surface antigen internalization in the tumor cells is impaired or abrogated relative to the control cells, or classifying the tumor as a therapeutic antibody resistant tumor if the detected ligand-induced cell surface antigen internalization in the tumor cells is the same as, similar to, or even greater than the control cells.

Ligand-induced cell surface antigen internalization may be carried out by any suitable means. Receptor internalization assays are well known in the art, representative examples of which are described in Fukunaga et al. (2006) *Life Sciences* 80(1):17-23; Bernhagen et al. (2007) *Nature Medicine* 13:587-596; natureprotocols.com/2007/04/18/receptor_internalization_assay.php). One well-known method to determine receptor internalization is to tag a ligand with a fluorescent label, e.g., a fluorescers or fluorescent dye such as Alexa Fluor 488, fluorescein isothiocyanate, Texas red, rhodamine, and the like, a fluorescent protein such as Green Fluorescent Protein (GFP), or other suitable labeling agent. Upon binding of the ligand to the receptor, fluorescence microscopy may be used to visualize receptor internalization. Similarly, a receptor (e.g., EGFR) may be tagged with a labeling agent and fluorescence microscopy may be used to visualize receptor internalization. If ligand-induced receptor internalization is reduced in tested cells, lessened internalization of fluorescence will be observed in those cells as compared to appropriate control cells (e.g., fluorescence may be observed only at the periphery of the cell where ligand binds the receptor rather than in endosomes or vesicles). Of course, other labels may be employed instead of fluorescent labels, including: chemiluminescent compounds such as luciferin; 2,3-dihydrophthalazinediones such as luminol; radioactive labels such as $^3$H, $^{125}$I, $^{35}$S, $^{14}$C, or $^{32}$P; enzymes such as horse radish peroxidase, alkaline phosphatase and others commonly used in immunoassays, and colorimetric labels such as colloidal gold or colored glass or plastic beads such as polystyrene, polypropylene or latex.

In some embodiments, receptor internalization assays may involve the detection or quantification of cell surface antigen using immunological binding assays (e.g., when using a radiolabeled antibody to detect the amount of ligand to the cell surface antigen or cell surface antigen on the cell surface during a receptor internalization assay). Immunological binding assays are widely described in the art (see, e.g., U.S. Pat. Nos. 4,366,241; 4,376,110; 4,517,288; and 4,837,168). For a review of the general immunoassays, see also Methods in Cell Biology: Antibodies in Cell Biology, volume 37 (Asai, ed. 1993); Basic and Clinical Immunology (Stites & Ten, eds., 7th ed. 1991). Commonly used immunoassays include noncompetitive assays, e.g., sandwich assays, and competitive assays.

In advantageous embodiments, the receptor internalization assays used for the tumor classification methods of the present invention are those described in the examples.

All the essential materials and reagents (e.g., labels, antibodies, ligands etc.) required for assaying internalization of a cell surface antigen/receptor (e.g., Her2/neu, EGFR, Epcam, VEGFR, FGFR, MUC-I, CA 125, CEA, MAGE, CD20, CD19, CD40, CD33, A3, antigen specific to A33 antibodies, BrE3 antigen, CD1, CD1a, CD5, CD8, CD14, CD15, CD16, CD21, CD22, CD23, CD30, CD33, CD37, CD38, CD40, CD45, CD46, CD52, CD54, CD74, CD79a, CD126, CD138, CD154, B7, Ia, Ii, HM1.24, HLA-DR (e.g., HLA-DR10), NCA95, NCA90, HCG and sub-units, CEA (CEACAM5), CEACAM-6, CSAp, EGP-I, EGP-2, Ba 733, KC4 antigen, KS-I antigen, KS1-4, Le-Y, MUC2, MUC3, MUC4, P1GF, ED-B fibronectin, NCA 66a-d, PAM-4 antigen, PSA, PSMA, RS5, S100, TAG-72, T101, TAG TRAIL-R1, TRAIL-R2, p53, tenascin, insulin growth factor-1 (IGF-I), Tn antigen etc.) may be assembled together in a kit. The kits may also optionally include appropriate reagents for detection of labels, positive and negative controls, washing solutions, blotting membranes, microtiter plates dilution buffers and the like. Such kits also generally will comprise, in suitable means, distinct containers for each individual reagent. The kit can also feature various devices and reagents for performing one of the assays described herein; and/or printed instructions for using the kit for assaying receptor internalization.

In some embodiments, the methods described herein are performed, at least in part, by a processing system, such as a suitably programmed computer system. A stand-alone computer, with the microprocessor executing applications software allowing the above-described methods to be performed, may be used. Alternatively, the methods can be performed, at least in part, by one or more processing systems operating as part of a distributed architecture. For example, a processing system can be used to assay receptor internalization. A processing system also can be used to determine the ligand-induced receptor internalization status of a tumor, and/or the receptor therapeutic antibody sensitivity of a tumor, and/or to stratify a subject into a treatment subgroup selected from receptor therapeutic antibody responders and non-responders, on the basis of the receptor internalization status. In some examples, commands inputed to the processing system by a user assist the processing system in making these determinations.

In one example, a processing system includes at least one microprocessor, a memory, an input/output device, such as a keyboard and/or display, and an external interface, interconnected via a bus. The external interface can be utilized for connecting the processing system to peripheral devices, such as a communications network, database, or storage devices. The microprocessor can execute instructions in the form of applications software stored in the memory to allow a process (e.g., determination of ligand-induced receptor internalization status, and/or determination of therapeutic antibody sensitivity of a tumor, and/or stratification of a subject into a treatment subgroup selected from therapeutic antibody responder and non-responder) to be performed, as well as to perform any other required processes, such as communicating with the computer systems. The applications software may include one or more software modules, and may be executed in a suitable execution environment, such as an operating system environment, or the like.

The tumor classification methods of the present invention are useful for stratifying cancer-affected subjects into therapeutic antibody responders and therapeutic antibody non-responders. Thus, when a subject's tumor is determined as having an impaired or abrogated ligand-induced cell surface antigen internalization status, the subject is stratified as a responder to therapeutic antibody therapy. Conversely, when a subject's tumor is determined as having an unimpaired ligand-induced cell surface antigen internalization status, the subject is stratified as a non-responder to therapeutic antibody therapy. In some embodiments, this stratification, in turn permits, better management of cancer-affected subjects in which non-responders are co-administered a receptor mediated endocytosis inhibitor with the therapeutic antibody. However, these methods for stratifying subjects into treatment subgroups are not necessary. Accordingly, the present invention further contemplates co-administering the therapeutic antibody and inhibitor of receptor-mediated endocytosis to subjects regardless of whether a subject is, is known or is suspected to be a responder or non-responder, as the administration of inhibitor of receptor-mediated endocytosis will stimulate the development, enhance or otherwise maintain an antibody responder status in the subject.

In order that the invention may be readily understood and put into practical effect, particular preferred embodiments will now be described by way of the following non-limiting examples.

EXAMPLES

Example 1

Disregulation of EGFR in Keratinocyte Tumors

Materials and Methods

Materials

Cell lines include seven lines from HNSCC including examples derived from the tongue, pharynx and hypopharynx; SCC-9, SCC-15, SCC-25, Detroit-562, Cal 27, FaDu, and Colo-16. In addition a further two lines have been used, KJD, derived from transformed human epidermal keratinocytes and A-431, derived from a vulval SCC and known to overexpress EGFR. Cell line identities were verified by SNP analysis. Cells were *mycoplasma* free and tested regularly. Cells were grown in Ham's F-12 media: DMEM supplemented with 10% FBS, 10 mM HEPES, 2 mM L-Glutamine, 1 mM Sodium pyruvate (Gibco, Invitrogen). For basal conditions cells were grown for 3 hrs in complete media but without 10% FBS. Other reagents included Alexa488-labelled EGF (Invitrogen), EGFR (clone 3107; Invitrogen) Alexa-594 goat anti-mouse IgG (A11005; Invitrogen), HRP-conjugated goat anti-mouse IgG (A10547; Invitrogen), Mouse anti-flotillin-1 IgG (610821; BD Transduction Laboratories).

Sample Acquisition

Patients with suspected SCC or intra-epidermal carcinoma (IEC) are identified by doctors. Live tissue samples are transported on ice to the department of anatomical pathology, where a trained pathologist dissects the sample and provides a suitable portion of tissue for laboratory investigation. Whilst actinic keratoses are not specifically sought for this study as they would not usually be excised, any biopsied lesions which subsequently prove to be actinic keratosis (AK) may be included and uninvolved skin tissue is acquired from the margins of excision specimens.

EGFR Stimulation and Uptake Studies

In brief, the technique used for sample preparation is as follows. Tissue samples are collected from clinical areas immediately after excision from the patient. A small, representative section is provided by the pathologist and this is sectioned in a particular manner. Samples are oriented in a petri dish such that they can be cut vertically producing section approximately 1 mm in thickness and encompassing the full thickness of the specimen less any subcutaneous fat which is excised prior to sectioning. Sectioning is performed by hand using a scalpel or razor blade. Samples are then treated in cold serum-free media washes for up to one hour. EGF (EGF-Alexa Fluor 488-Invitrogen) is added to the SFM and the samples incubated at 37° C. for various time points. Some samples do not have EGF added as a control and others first have cetuximab added and are incubated for 30 minutes prior to the addition of EGF as a control in which ligand binding should be blocked. After incubation for the appropriate time points, uptake is stopped by cooling in ice and washing in cold PBS with 0.1% Triton X-100 (PBTx). After several washes samples are fixed in 4% paraformaldehyde overnight.

Whole Mount Immunofluorescence

Samples are subjected to a bleaching protocol using Dent's bleach followed by a methanol series to bring the samples back to aqueous. Immunofluorescence can then be performed using various antibodies with excess binding blocked by incubation in 10% Horse serum in PBTx. In most cases anti-EGFR antibody (Mouse anti-EGFR, clone 31G7-Invitrogen) is used to visualize the receptors, however in the case of large tumor samples with multiple sections available, other antibodies may be used additionally such as anti-EEA1 and anti-clathrin antibodies. After this an appropriate secondary antibody conjugated to Alexa is used and DAPI is added for nuclear staining. Some samples are exposed to secondary antibody only serving as a staining control. Samples are then mounted on slides with a central depression using Prolong Gold™ anti-fade mounting reagent (Invitrogen) and sealed prior to imaging with the Zeiss confocal microscope.

Imaging

Slides were imaged using a Zeiss 510 Meta laser confocal microscope with a 63× objective with Zen 2008 software. Slides were examined for histological features to confirm localization to the epidermis at both 63× and 25×. Features noted were the presence of the dermo-epidermal junction and basement membrane, typical appearance of the dermis with autofluorescent collagen and paucity of cells, a typical appearance of the epidermis with stratified squamous epithelium and in dysplastic tissue, irregularity with nuclear pleomorphism. The thickness of the epidermis is significant as epidermal thickening and hyperplasia is a feature of dysplastic lesions. In the stratum corneum also, thickening can be seen as well as parakeratosis, both features of dysplastic lesions. Multiple regions of epidermis or nests of invasive keratinocytes are imaged at 63× to clearly show the distribution of EGF488. Where possible z-stack images are taken of representative tumor regions. Images are taken at 25× magnification or tile scans at 63× to show overall features of the specimen.

Image Analysis

Figure 1:
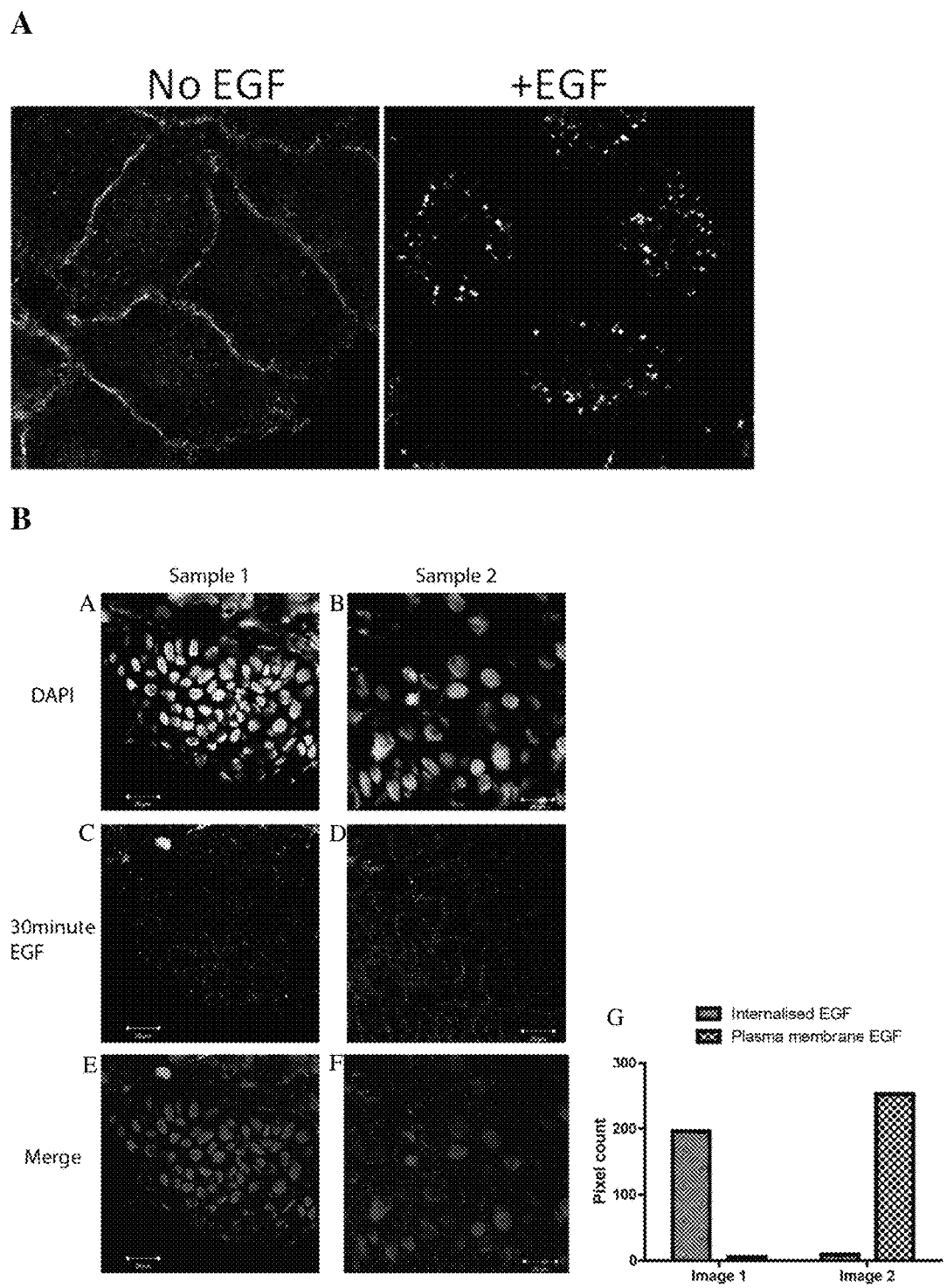
FIG. 1A is a photographic representation showing receptor endocytosis in cell lines by Alexa-fluor labeling of EGFR before and after the addition of EGF.
FIG. 1B is a photographic and graphical representation showing EGF uptake versus disregulation in representative skin tumor samples. Panels A and B show DAPI stained nuclei, Panels C and D show EGF-Alexa488 in green emission channel and Panels E and F show the merged images. Panel C shows internalized EGF in Sample 1 while Panel D shows non-internalizing plasma membrane localized EGF in Sample 2. Panel G shows quantitation of internalized versus plasma membrane bound EGF at 30 minute stimulation time point is shown for Sample 1 (Image 1) and sample 2 (Image 2).

Images were reviewed with an experienced researcher in the use of cellular immunofluorescence techniques (supervisor FS) and categorized on the basis of the principle appearance of the distribution of Alexa-EGF488 as either 'internalized' or 'disregulated'. Internalized tumor samples predominantly show a punctate staining pattern corresponding to internalized receptors grouped into endosomal structures at varying distances from the nucleus. After 30 minutes of stimulation with EGF-488, disregulated examples show punctate or semi-confluent staining in a distribution consistent with the location of the plasma membrane (FIG. 1).

Quantification of the degree of uptake was performed using Photoshop software. This process generated a data output which can be graphically represented to show degree of internalized versus disregulated for each tumor sample based on as many images as are available.

Nuclear morphometry analysis was performed using Image J software. Confocal images taken at 63× with a size of 142.6×142.6 micrometers were utilized. Tumor images were taken from representative portions of the tumor showing EGF-488 or EGFR positivity. A standard size area was taken from each image of 2500 $\mu m^2$, usually in the form of a 50×50 $\mu m^2$. The region sampled included a portion of the basal cell layer, where the highest level of EGF uptake was noted, wherever possible. Areas excluded regions of dermis or other areas of low cellularity and those with high levels of abnormal or non specific appearing coloration such as caused by autofluorescence. Images were thresholded to highlight as much of all the nuclei as possible and then converted to binary. The watershed tool was used to insert divisions between nuclei. The resultant image was checked for similarity with the original image. Adequate binary images were then analyzed automatically. This resulted in numbering of all nuclei included and generation of morphometric data set. These included; nuclear Cross-sectional area, Perimeter, Best fitting ellipse data (length of major and minor diameters and angle of major axis from the x axis of the image), Feret data (Longest caliper/feret distance,) and shape parameters principally Aspect ratio (length of major diameter of best fitting ellipse divided by length of minor diameter). Data generated from this analysis was plotted and analyzed using Graphpad Prism™ 5' software package. Comparisons between tumor tissue and adjacent skin controls and between different tumors were performed using Mann-Whitney U test for unpaired data.

EGFR expression was assessed digitally on images of tumor and control tissue after immunofluorescence with a specific antibody. Software package NIS-Elements™ (Nikon) was used with settings standardized against an example of a highly EGFR expressing SCC and a very low expressing control skin sample.

Results

Tumor Analysis and EGF Uptake

Figure 2:
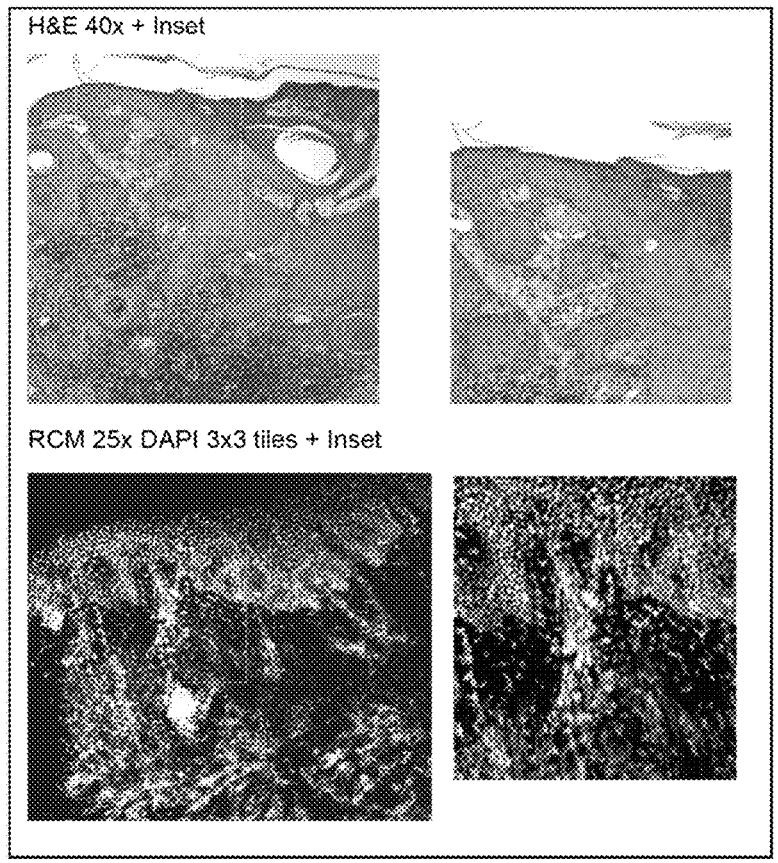
FIG. 2 is a photographic representation depicting an invasive SCC shown by H&E and confocal microscopy. The epidermis is thickened and dysplastic. Nuclear disorganization and invasion can be seen clearly in the RCM image in which nuclei stained with DAPI are shown. There is a dense inflammatory infiltrate in the dermis. Little stratum corneum is visualized in either image in this case.
Figure 3:
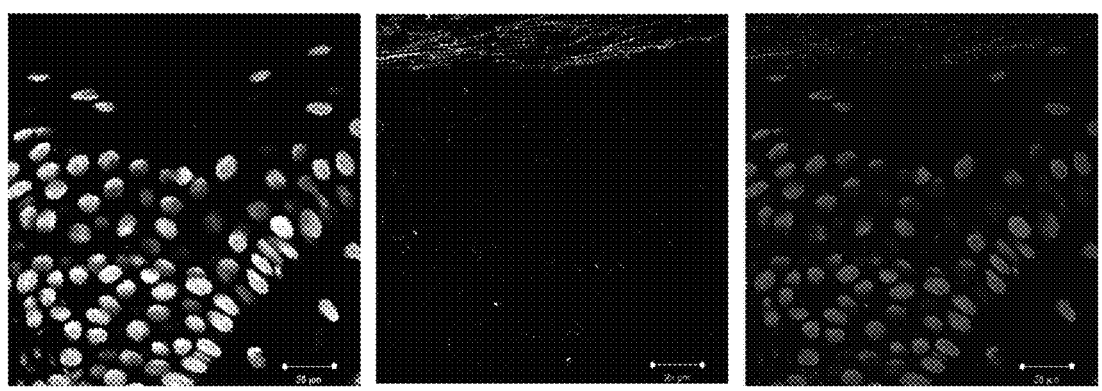
FIG. 3 is a photographic representation showing a normal skin sample panel, RCM 63×. Nuclei are stained with DAPI. The corneocyte envelopes strongly autofluoresce in the red emission spectrum. Panel A shows DAPI staining, panel B shows the red emission channel and Panel C shows a merged image of the two channels. Nuclei are sparse in comparison to dysplastic samples and are widely spaced. The epidermis is thin and there is a thin layer of normal orthokeratosis. There is a well demarcated basal layer with no invasion or inflammatory infiltrate visible.
Figure 4:
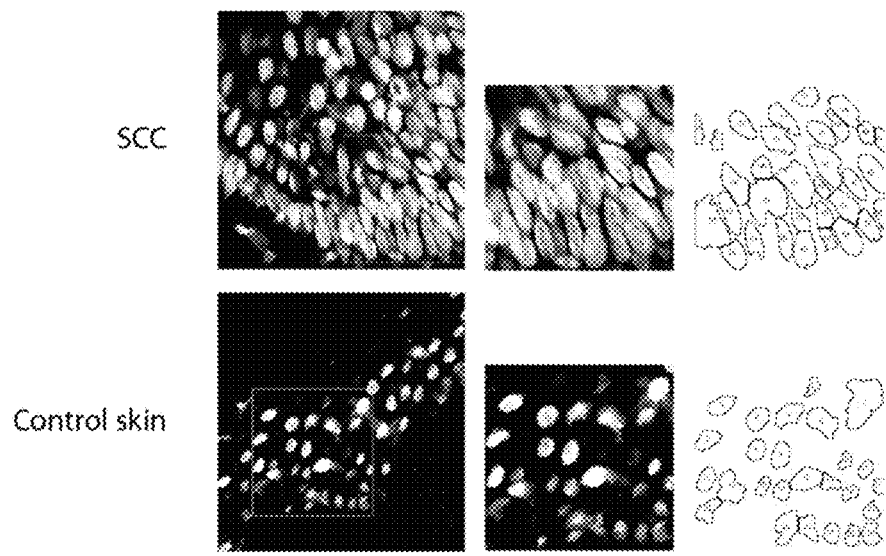
FIG. 4 is a photographic and graphical representation showing nuclear quantitation in SCC and normal skin. Assessment of mean cross sectional area and aspect ratio also demonstrates the expected difference between nuclei of normal and dysplastic keratinocytes. A larger aspect ratio indicates deviation away from a perfect circle. The upper panel shows SCC nuclei, a magnified area chosen for quantitation and the area picked by the imaging software for quantitation. The mid-panels show the same for a control 'normal' skin sample. The left graph shows the nuclear area quantitation of the two samples and the right graph shows quantitation of the nuclear aspect ratio.
Figure 4:
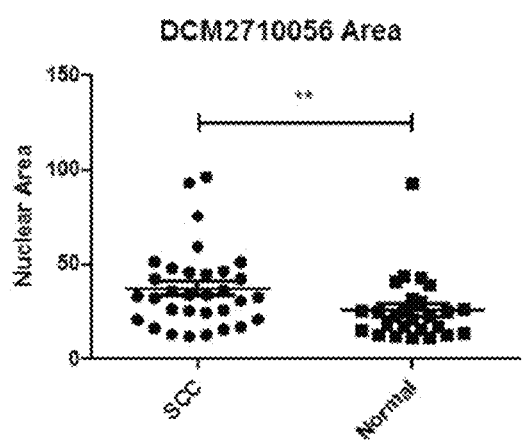
Figure 4:
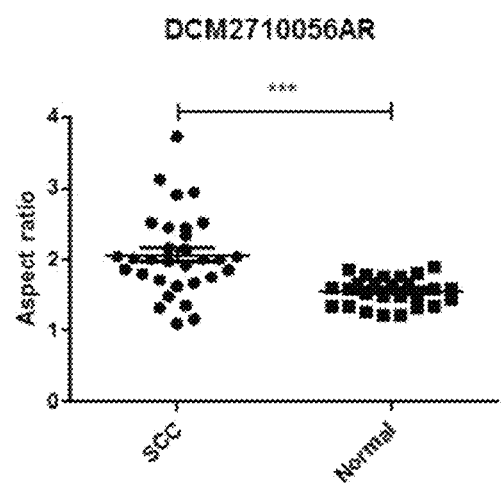
Figure 5:
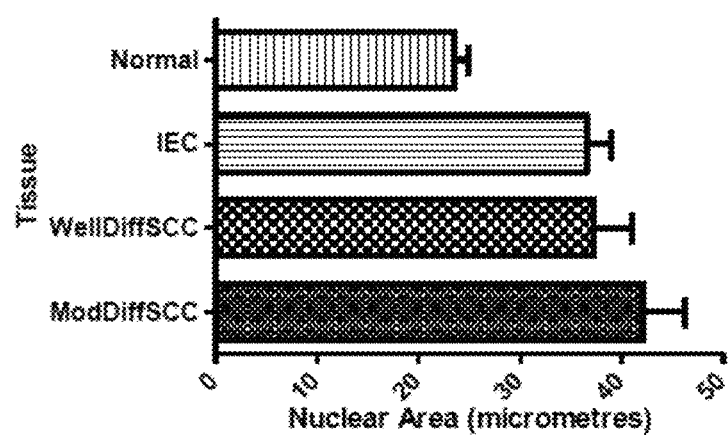
FIG. 5 is a graphical representation showing an example of nuclear morphometry data from 3 lesions with associated normal skin controls. Nuclear cross-sectional area for each lesion was significantly different from its matched control skin sample ($P<0.05$). Here normal skin is shown as the mean of the data from all three control samples. Although the lesions show the predicted increase in nuclear area with increasing invasiveness this was not significant.

Optimization of cutaneous sample analysis by whole mount confocal imaging was undertaken. Careful sectioning by hand was sufficient to demonstrate all vertical regions of the skin on processed and mounted samples. This allowed each section to be assessed for a limited array of histological features of the corresponding pathological diagnosis (FIGS. 2 and 3). In addition to this, initial analysis of nuclear morphometry demonstrated significant differences between tumor tissue and control skin (FIG. 4) and differences, although not significant in nuclear area between different pathological types of squamous lesions (FIG. 5).

Figure 6A:
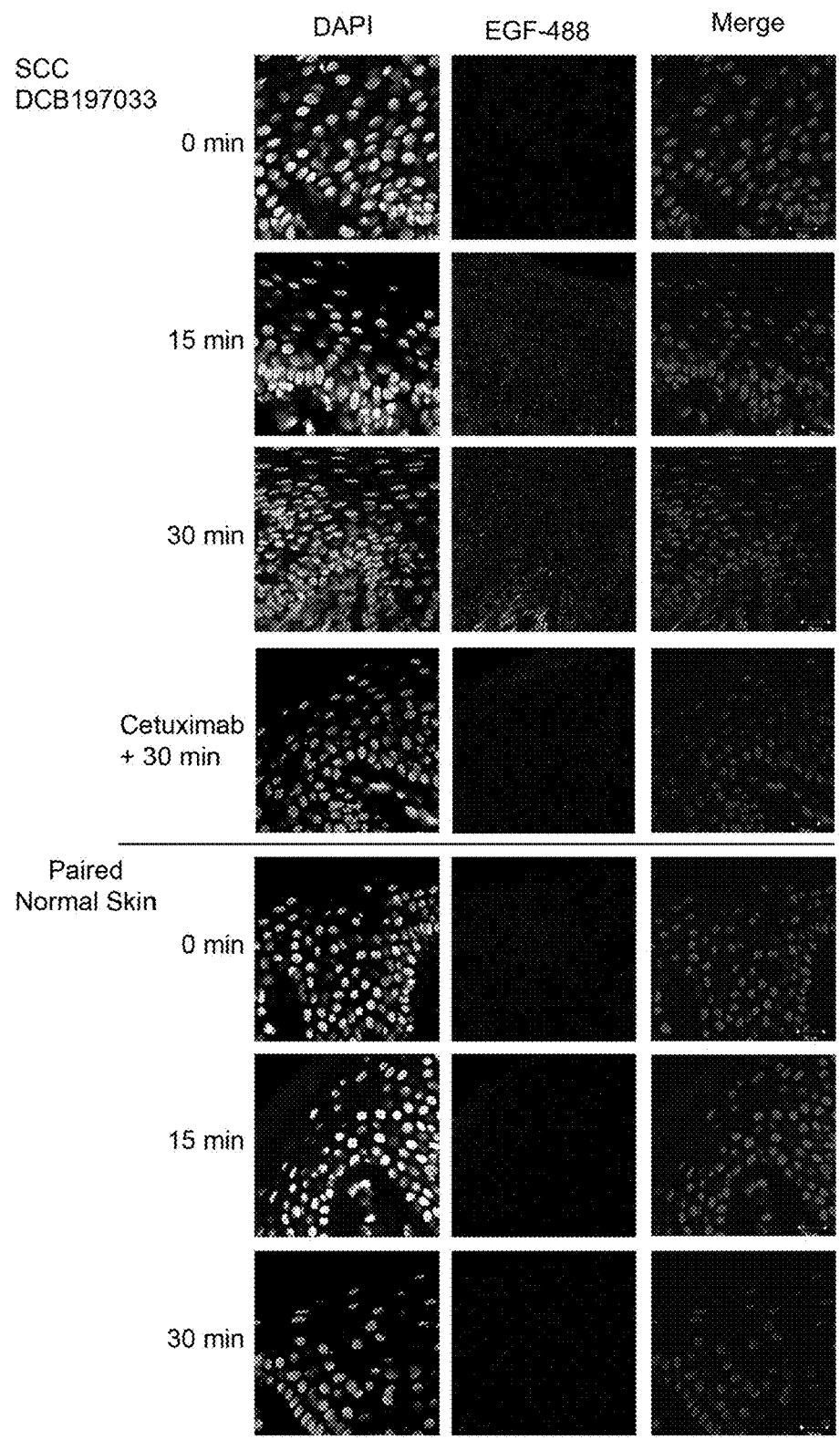
FIG. 6 is a photographic representation showing examples of tumors demonstrating normal ligand-induced receptor-mediated endocytosis of EGF. A. DCB177033 is a well differentiated SCC from the back of an elderly male. The tumor extended to the deep dermis. The difference in nuclear density and disorganization between the tumor sections and adjacent uninvolved skin is apparent. A small amount of specific EGF-488 binding is seen at the 15 minute time point. Normal ligand-induced EGF internalization is seen at the 30 minute time point. Cetuximab prevents uptake of EGF. There is minimal EGF-488 uptake in the control skin even at the 30 minute time point. B. DCV299052 is an IEC from the forearm of a female. The control skin from adjacent to the lesion showed marked variability. Some regions appeared normal in gross appearance and these demonstrated little EGF-488 uptake or EGFR positivity. C. Other sections of the control skin were atypical in nuclear appearance and demonstrated increased EGFR positivity and EGF uptake. As the control skin is taken from immediately adjacent to the tumor and judged to be non-involved by the naked eye only, there is potential for tumor tissue to be found also in these control samples. This may also reflect the severe photo-damage observed on a more exposed body site. Again normal internalization of EGF-488 is observed by 30 minutes unless tissue is first treated with cetuximab.
Figure 6B:
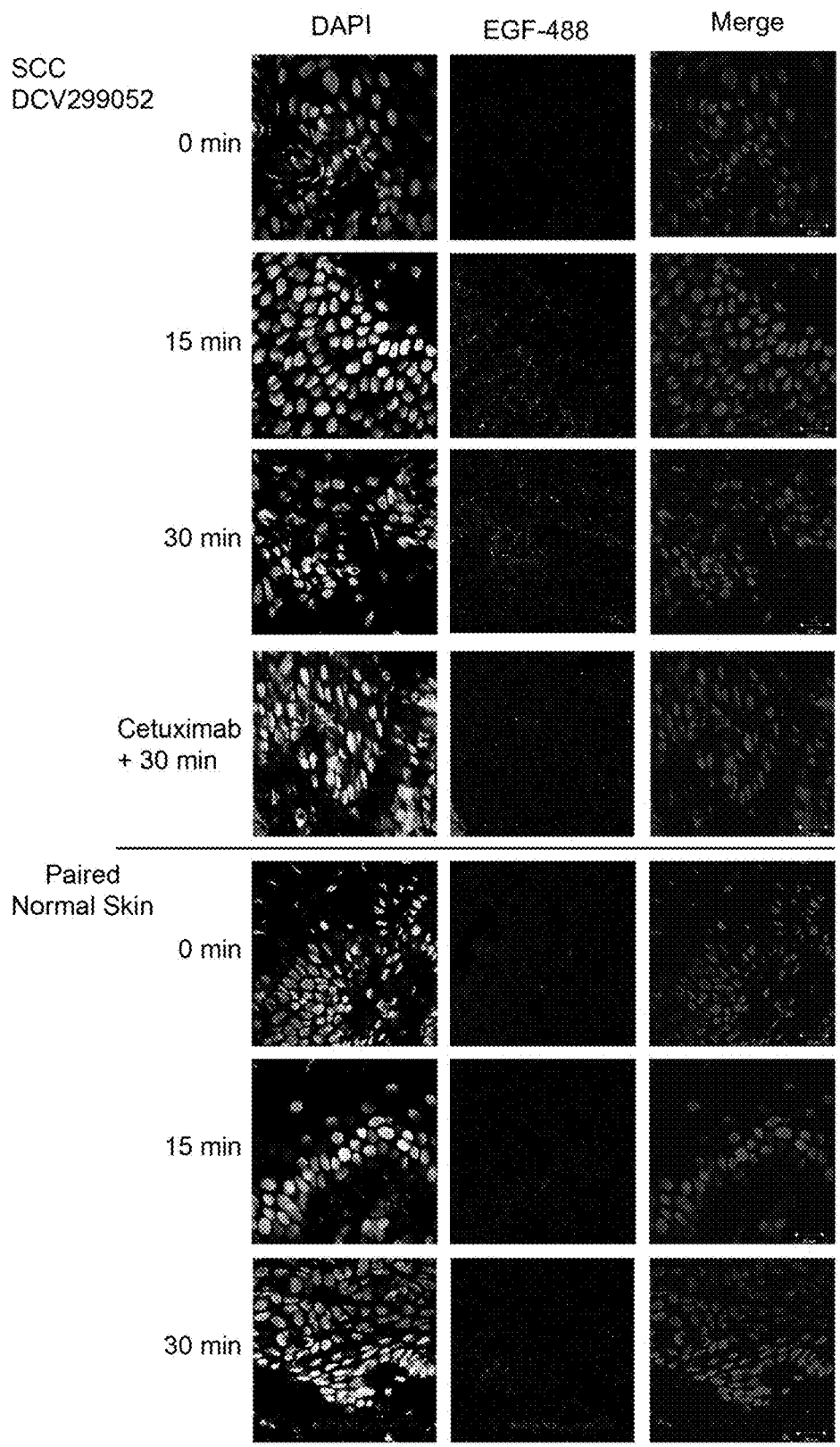
Figure 6C:
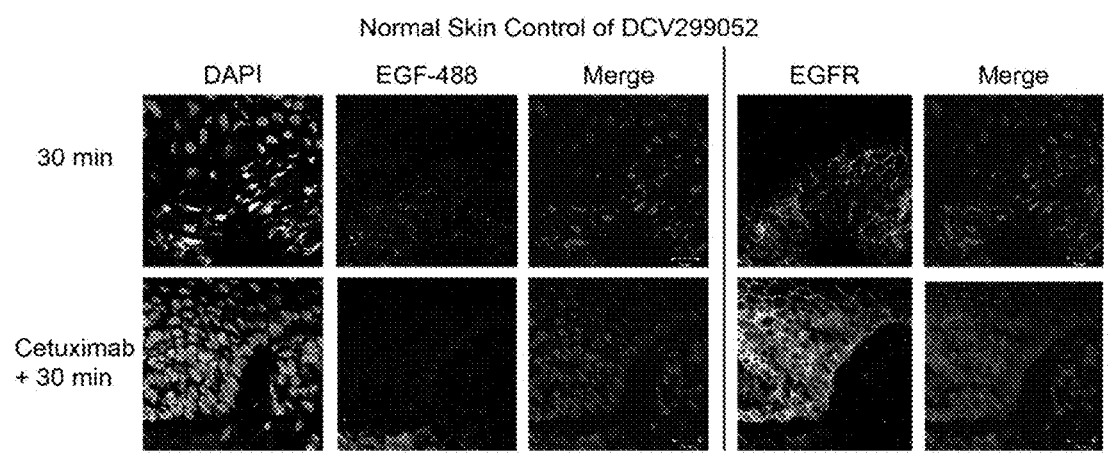
Figure 7A:
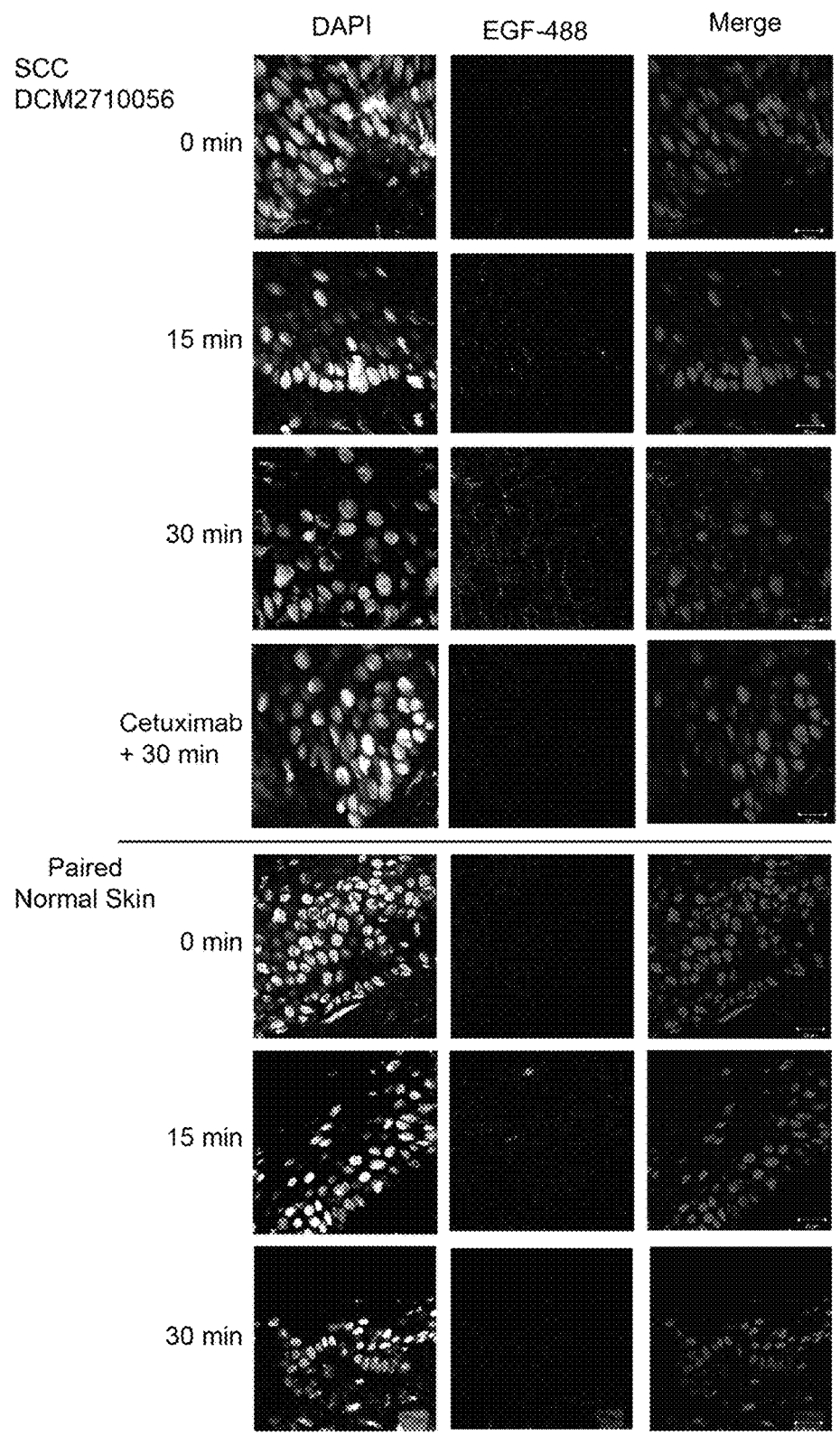
FIG. 7 is a photographic representation showing examples of tumors demonstrating loss of ligand-induced EGFR endocytosis, termed as 'disregulated.' EGF-Alexa488 remains localized at the plasma membrane at the 30 minute time point. DCM2710056 is an SCC from the forearm of a 60 year old man, while DCB238043 is an SCC from the neck of an 80 year old female. No significant EGF is seen in control normal skin samples.
Figure 7B:
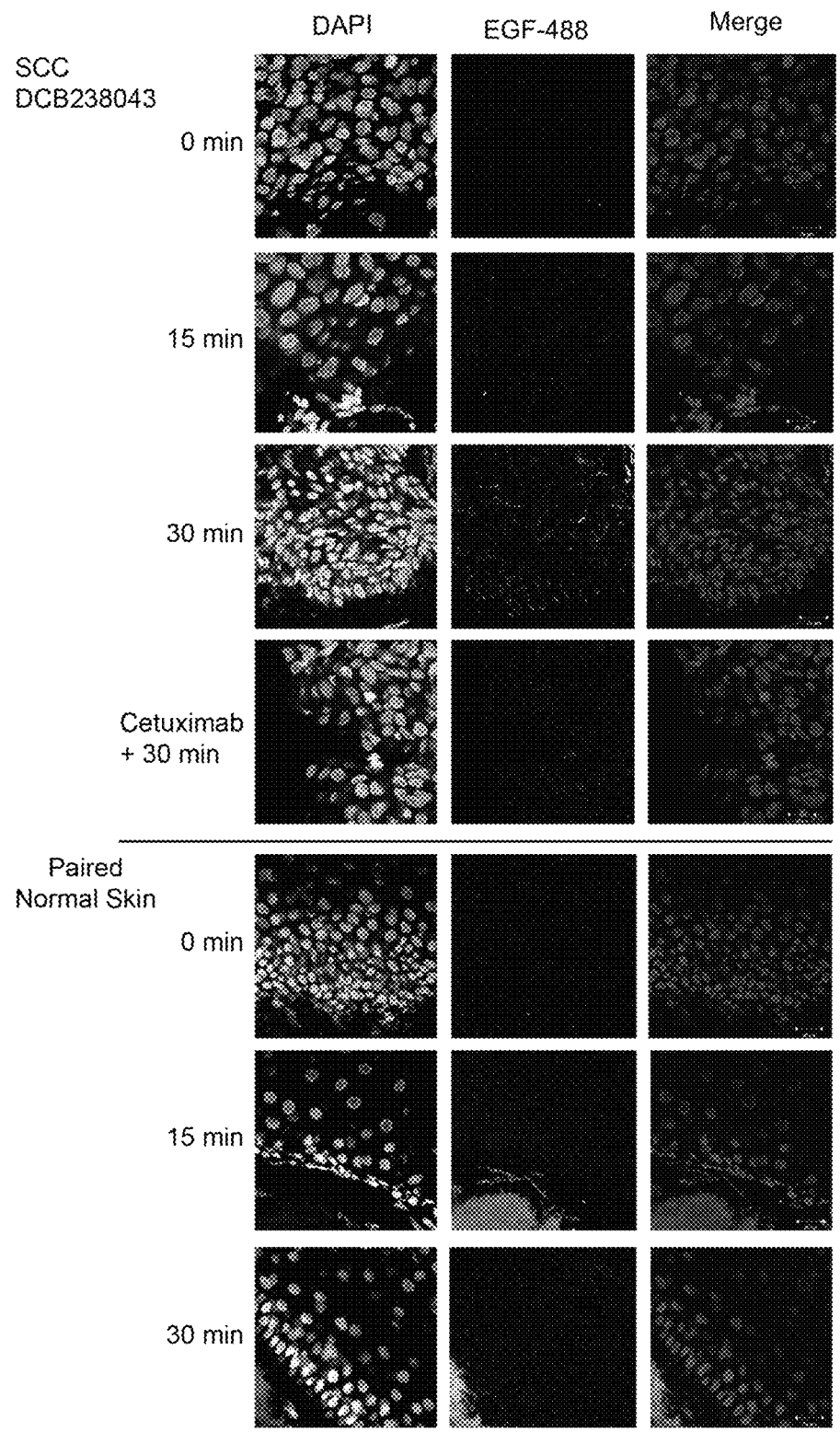
Figure 8:
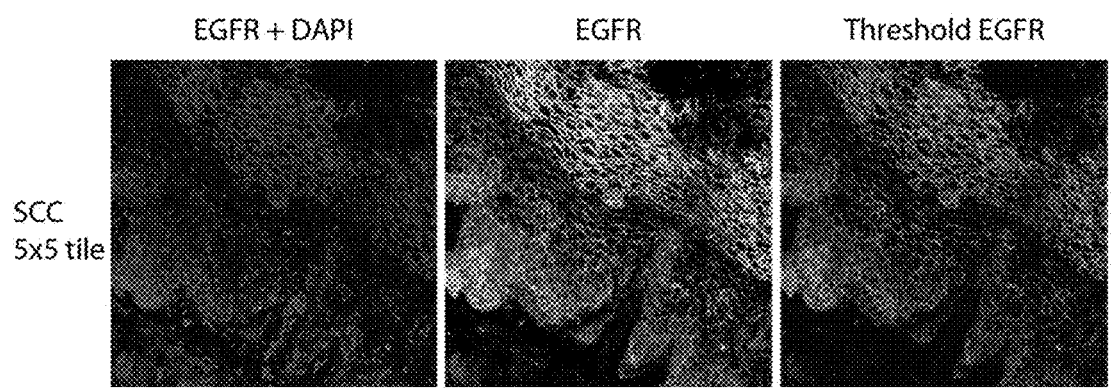
FIG. 8 is a photographic representation showing EGFR expression across the epidermis. EGFR expression in the epidermis is shown in red in the original image on the left. Expression can be seen more clearly in grayscale without nuclei. In the final image EGFR intensity has been thresholded to exclude staining in the upper levels of the epidermis. Strong expression can still be seen in the basal layers of the epidermis in several regions. The stratum corneum demonstrates bright autofluorescence in the red channel but does not express EGFR.

For each sample EGF uptake studies were performed on the fresh tumor specimens using the methods described. Control skin samples if available were also subjected to the protocol. Sample images were reviewed with a supervisor (FS) and a determination made as to the predominant localization of the labeled EGF at the 30-minute time point (FIG. 6). In a small number of cases adequate 30-min samples were not available and the determination was made on a 15-min time point sample. In the majority of cases with an adequate 30-min time point result a determination could be made at the 15-min time point which corresponded to the 30 min result. As a result, tumors were categorized as either 'internalized' if EGF is appreciably endocytosed on examination (FIG. 7) or 'disregulated' if the EGF appeared to be predominantly accumulated on the plasma membrane (FIG. 8).

Figure 9:
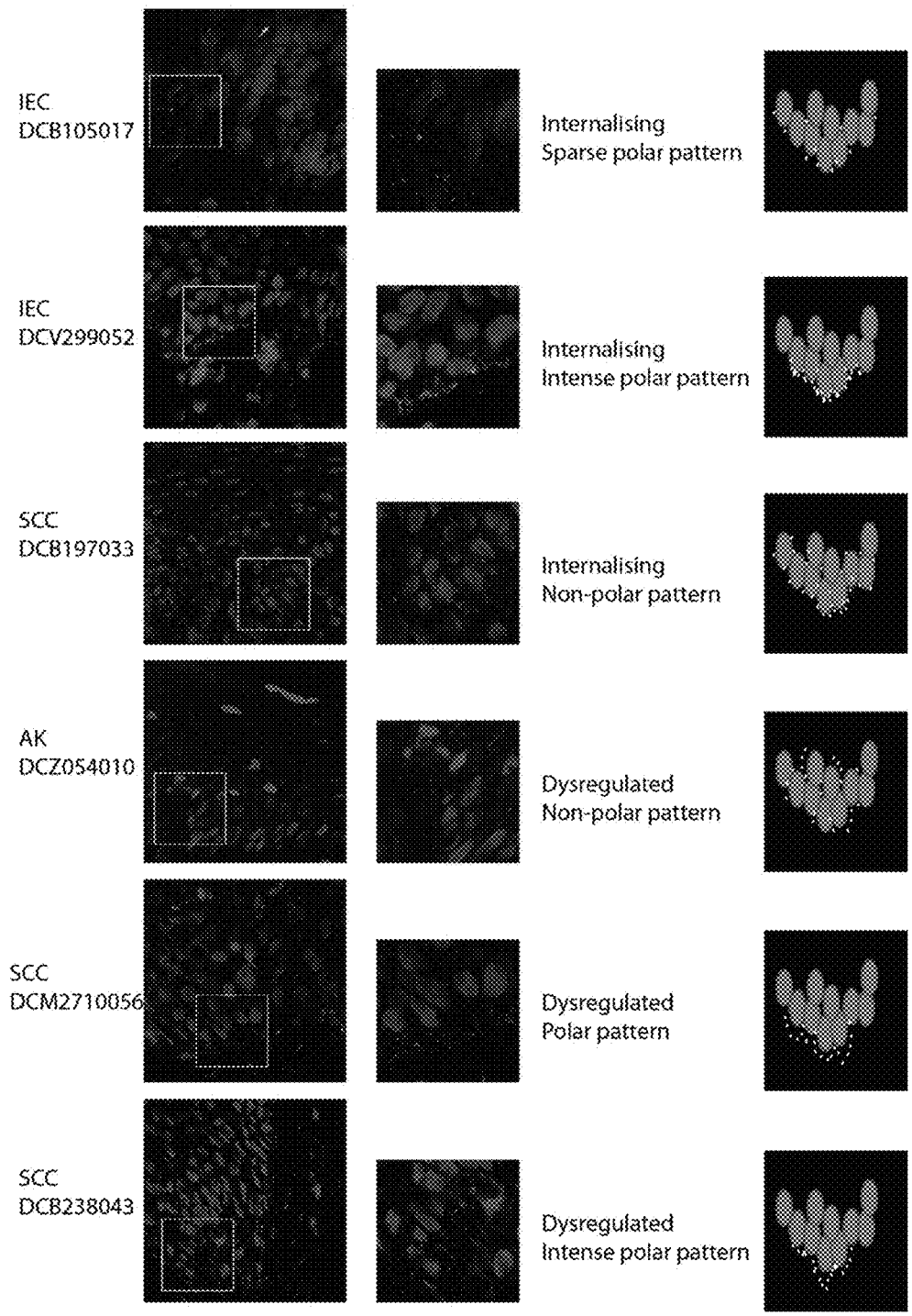
FIG. 9 is a photographic and diagrammatic representation showing predominant uptake in basal layers and leading edge of tumors. Various subtype patterns were seen. Some are not polarized while some show strong polarization of uptake to the basal pole of the cells. As EGFR signaling is known to be involved in metastasis and cytokinetic migration this may be a significant observation.
Figure 10:
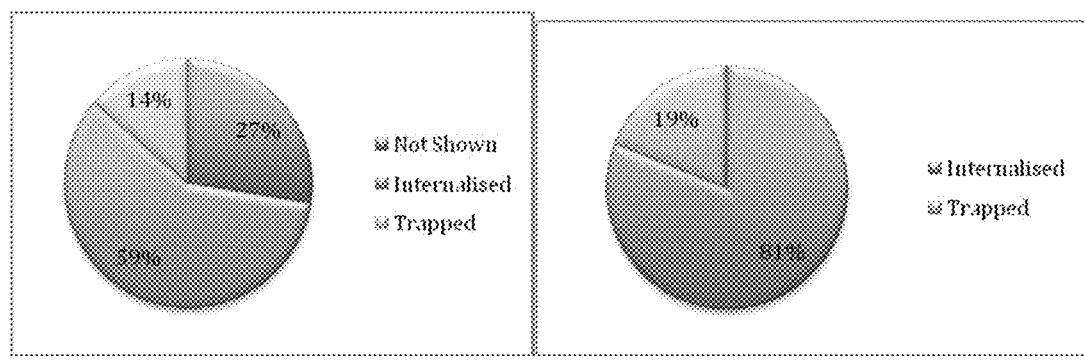
FIG. 10 is a photographic representation showing trafficking status of squamous lesions: pies charts. Trapped indicates tumors whose EGFR no longer undergoes ligand-induced endocytosis and remains localized to the plasma membrane. Internalized indicates tumors whose EGFR underwent ligand-induced receptor-mediated endocytosis and at 15 or 30 minute time-points showed endosomal localization of EGFR.

As expected, EGFR expression was most intense in the basal layers and at the invasive edges of tumors (FIG. 9). It was in this region that EGF-488 was usually visualized. Several different subtypes of EGF localization were noted in the most basal keratinocyte layers (FIG. 10). In particular, several tumors demonstrated marked basal polarization of EGF uptake. This is consistent with the invasive nature or potential of these lesions.

There were 26 patients who provided 29 lesions for examination. Patients were all of fair skin types I-III. Basic demographic information was collected along with significant data from the medical histories. Risk factors for the development of SCC and for advanced, recurrent or metastatic SCC were recorded wherever data was available. Important information regarding the patients' skin cancer history was also recorded. All patients had had a previous skin malignancy but not all had a previous SCC. Between 0-4 previous SCCs was most common with 11 patients having had >5 previous SCCs with a maximum of 18. A history of a previous high risk SCC was defined as a lesion which demonstrated any of the tumor-specific high risk factors outlined in Table 1.

TABLE 1

RISK FACTORS FOR RECURRENCE, METASTASES OR DEATH IN CUTANEOUS SQUAMOUS CELL CARCINOMA (CRANMER ET AL., 2010; WOLLINA, 2012)

| | |
|---|---|
| Gross/tumor factors | Lesion diameter >2 cm<br>Indistinct margins on clinical examination<br>Location at embryonic fusion planes or lips, ear or anogenital region<br>Associated with burn, chronic wound, ulcer or irradiated skin<br>Recurrent tumor |
| Histopathology | Depth >2 mm or Clark level IV (to reticular/deep dermis)<br>Poorly differentiated or infiltrating histology<br>Basosquamous or desmoplastic histology<br>Perineural or lymphovascular invasion<br>Positive surgical margins after resection of primary tumor |
| Host factors | Immunosuppression including organ transplantation<br>Chronic Lymphocytic Leukemia<br>Chronic dermatoses including; epidermolysis bullosa, xeroderma pigmentosum, epidermodysplasia verruciformis, albinism, pansclerotic morphea, hidradenitis suppurativa |

Sample characteristics are summarized in Table 2.

TABLE 2

PATIENT CHARACTERISTICS

| | |
|---|---|
| Age | Age mean 73.8 years (range 46-87) |
| Gender | M:F = 18:8 |
| High risk host features | Concurrently or previously immunosuppressed (n = 4, Indications-Vasculitis, Rheumatoid Arthritis, Nephrotic Syndrome, Lymphoma) CLL (n == 1) |
| Other SCC features in history | Number of previous SCC<br>History of ≥1 previous high risk SCC |

Results of Tumor EGFR Trafficking Analysis

Figure 11:
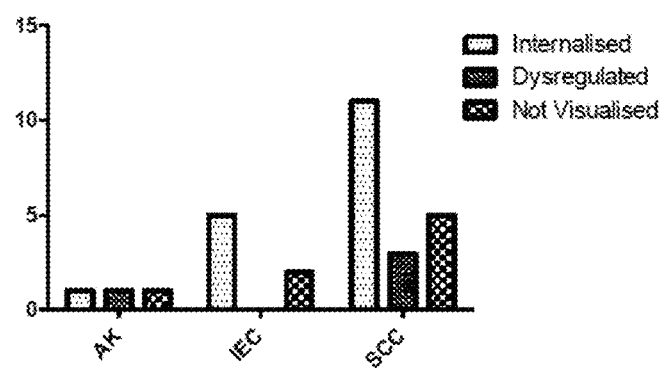
FIG. 11 is a graphical representation showing a tumor data set according to trafficking status and lesion type. No disregulated IECs were identified.

Tumors were characterized according to the grade or invasion stage noted on pathology and the EGF uptake status as outlined above. In eight cases (27%) EGF-488 was not seen and these could not be determined to be either internalizing or disregulated. There are a number of possibilities for this, including that the tissue was not viable by the time it reached the lab and uptake studies were performed. Of the remaining cases, 17 (59%) were seen to be EGF internalizing while 4 (14%) were disregulated (FIG. 11). A summary of tumor type and patient risk factors and trafficking status is shown in Table 3.

TABLE 3

TUMOR CHARACTERISTICS
The lesions coded as DCN124011 and DCN124012, and the lesions coded
as DCS124013 and DCS124013 are from a single patient. Tumor
risk factors marked with *, patient hgh risk factors marked with **.
EGFR trafficking status is designated as Internalized (I) ,Disregulated (D) or Not visualized (N).

| Lesion code | Diagnosis | Grade | Deeply Invasive | Other High Risk Tumor Features | Body site | High risk patient features & significant SCC history (# previous SCCs) | EGFR |
|---|---|---|---|---|---|---|---|
| DCW042001 | SCC | P | Y | | | (0) | I |
| DCH013002 | SCC | M | N | | | IS, HRx3, (5 + SCC) ** | I |
| DCD113006 | SCC | M | Y | | | | N |
| DCT243009 | AK | NA | NA | | | HRx3, (5 + SCC) ** | I |
| DCZ054010 | AK | NA | NA | | | (5 + SCC) | D |
| DCN124011 | SCC | W | N | | | IS ** | N |
| DCN124012 | SCC | M | N | | | IS ** | D |
| DCS124013 | SCC | M | Y | | | HRx1, (5 + SCC) * | I |
| DCS124013 | AK | NA | NA | | | HRx1, (5 + SCC) * | N |
| DCP105016 | IEC | NA | NA | | | HRx2, (5 + SCC) * | N |
| DCB105017 | IEC | NA | N | | | CLL,HRx3, (5 + SCC) ** | I |
| DCG125018 | SCC | W | VS | | | | N |
| DCJ275021 | SCC | W | N | | | | N |
| DCB197033 | SCC | W | Y | | | (0) | I |
| DCF217034 | SCC | M | VS | | | (0) | I |
| DCS227035 | IEC | NA | N | | | HRx1* | I |
| DCI227036 | SCC | P | N | | | | I |
| DCM267037 | SCC | M | N | | | (0) | I |
| DCK287038 | SCC | M | N | | | HRx1, (5 + SCC) * | N |
| DCF287039 | IEC | NA | N | | | PS | I |
| DCM159049 | IEC | NA | N | | | IS (0) ** | I |
| DCV299052 | IEC | NA | N | | | HRx2, (5 + SCC) | I |
| DCM2710056 | SCC | W | VS | | | IS, (5 + SCC) ** | D |
| DCB1111058 | SCC | M | Y | | Ear | PS, (5 + SCC) * | I |
| DCB1111059 | SCC | M | Y | | | PS, (5 + SCC) * | I |
| DCN2211060 | SCC | M | N | PNI, PS | | HRx1, (5 + SCC) * | I |
| DCB238043 | SCC | P | Y | | | (5 + SCC) | D |
| DCR242062 | IEC | NA | N | | | | N |
| DCE238042 | SCC | M | VS | | | HRx1 8 * _ | I |

HR = High Risk SCC, Ag = Aggressive SCC, PNI = Perineural Invasion, IS = Immunosuppressed, PS = Possibly recurrent SCC
(Not taken as independent evidence of HR unless confirmed)

Figure 12:
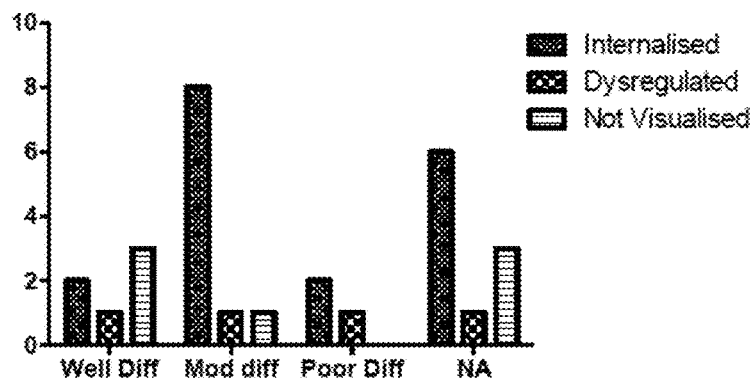
FIG. 12 is a graphical representation showing trafficking status and tumor grade frequency. Non-invasive precursor lesions are not assigned a pathological grade and so are not applicable (NA). The trafficking status of all poorly differentiated samples could be identified whereas in all other groups at least one lesion was in the not visualized category.
Figure 13:
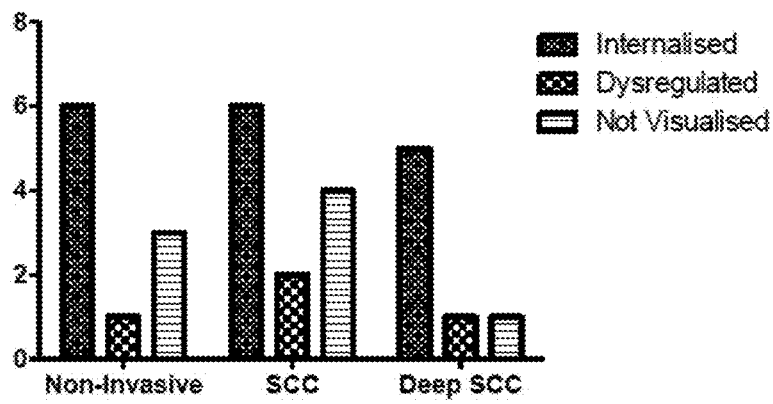
FIG. 13 is a graphical representation showing trafficking status and tumor type by depth of invasion.
Figure 14:
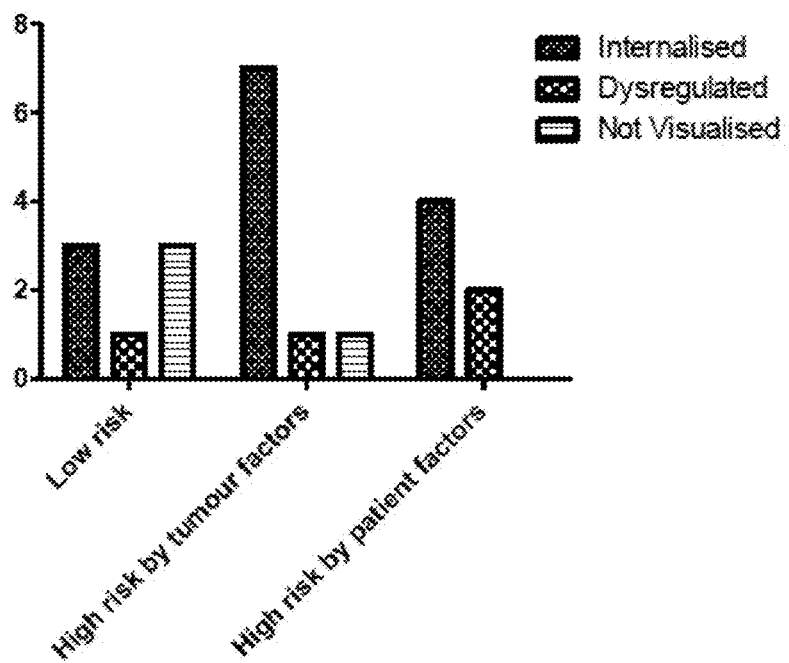
FIG. 14 is a graphical representation showing trafficking status and correlation with multifactorial risk stratification.

One AK out of three and three SCCs out of 19 were of the disregulated phenotype (FIG. 11). None of the seven IECs were disregulated, with five internalizing and two not visualized. Five of the SCCs were also in the not visualized category. Most tumors were classified as moderately differentiated. Most of the samples which could not be categorized as endocytosing or not were in the well differentiated grade tumors (FIG. 12). All the poorly differentiated tumors could be classified. This may relate to either EGFR expression or other particular features of the tumor tissue. Of the three disregulated SCCs, each was in a tumor of a different grade. Of 12 SCCs which were not reported as invasive to deep levels in histology, two were disregulated while one of seven deeply invasive SCCs was disregulated (FIG. 13). Approximately half (15/29) of the tumors could be classified as 'high risk' based on either tumor or patient factors (FIG. 14). Only one (25%) of the disregulated tumors was high risk by tumor factors as opposed to eight of the 1.7 internalizing lesions (47.1%). However, half (2) of the disregulated tumors occurred in high risk patients as opposed to just 23.5% (4) of the internalizing lesions.

Figure 15:
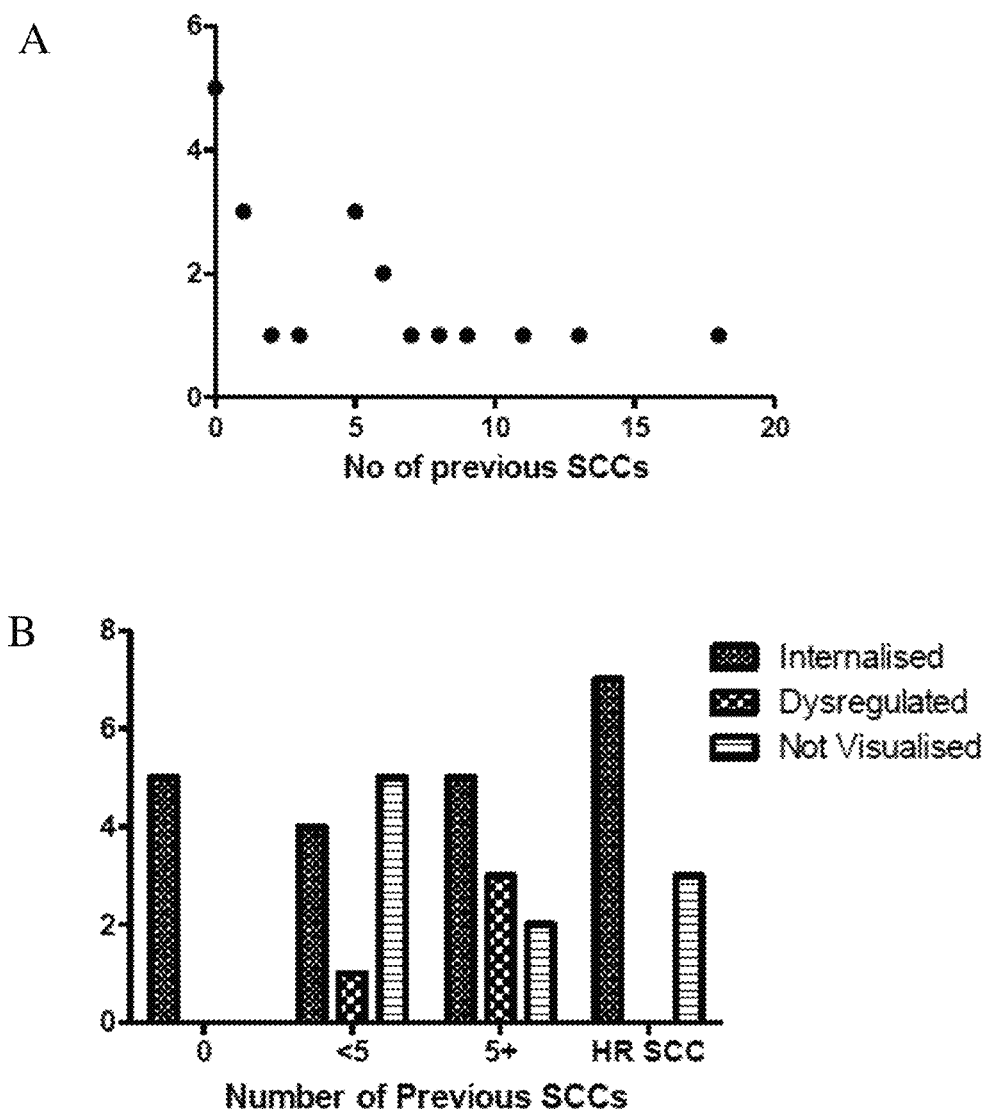
FIG. 15 is a graphical representation showing: A Plot of number of previous SCCs in sample population. Peaks are seen at Zero and five creating three 1.5 subgroups. B. Trafficking status compared to subgroup of prior history of SCC. Disregulated tumors were not seen in patients who had no previous SCCs. Disregulation was most common in patients with five or more previous SCCs. EGFR internalizing tumors occurred at a steady frequency across frequency groups. When high risk tumors are considered separately these were seen in the history of more than one third of internalizing cases but no patients with disregulated tumors fell into this category.

When SCC history was assessed, the data lent itself to division into three subgroups based on peaks in the numbers of previous lesions (FIG. 15A). Previous IEC and AK were not considered as these data are extremely difficult to obtain. None of the disregulated tumors occurred in patients who had no previous SCCs. Three quarters of the disregulated tumors were found in patients with a history of five or more SCCs and none of the disregulated tumors occurred in patients who had a previous high risk SCC (FIG. 15B).

Figure 16:
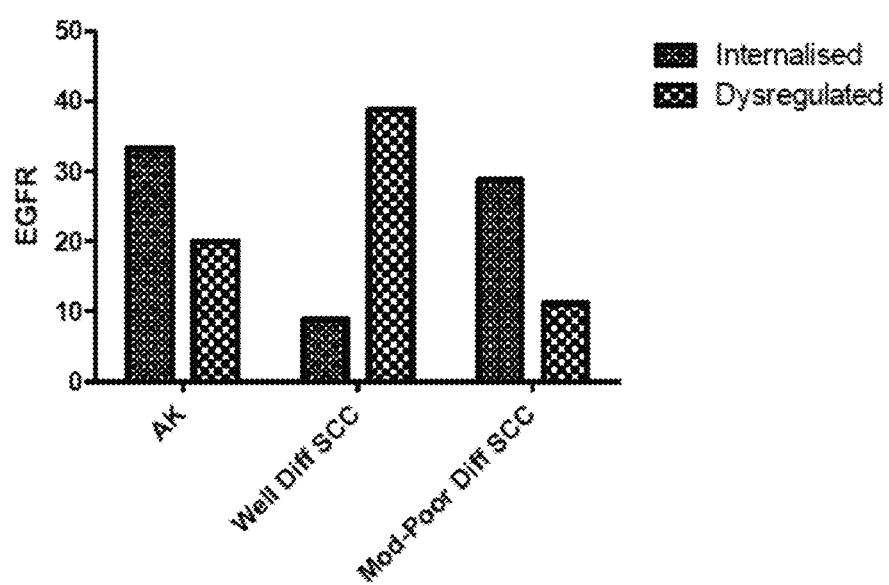
FIG. 16 is a graphical representation showing expression of total EGFR by quantification of tumor section immunofluorescence. Basal layers of the epidermis were analyzed in matched pairs of internalizing and disregulated tumors with similar histopathological tumor features. Total. EGFR expression levels did not increase with increasing tumor invasiveness or grade. There was no correlation between trafficking status and EGFR total expression levels.

Digital analysis of EGFR total expression levels in basal and invasive regions of keratinocytes was performed on matched pairs of internalizing and disregulated tumors (FIG. 16). This included one example in each category of an AK, a well differentiated SCC and a moderately to poorly differentiated SCC. There was no correlation between trafficking status and total EGFR expression.

Conclusions

A live human tissue EGF uptake study has been performed. Analysis has been performed by whole mount laser confocal fluorescent imaging. This technique can be used to determine trafficking status in early SCC and precursor lesions. Pathological features can be determined and dysplastic keratinocyte populations have been determined by subjective and objective measures. From this data set the following conclusions can be made:

Disregulation may be an early event in the development of SCC

Disregulation is more commonly seen in SCC with low risk characteristics

Disregulation occurs in patients who have had previous SCC and is more commonly seen in patients with multiple previous SCCs Disregulation occurs in patients who are at high risk for SCC Disregulation is not dependent on EGFR total expression level.

It is proposed therefore that:
Disregulation may occur in high risk individuals with previous SCC and is associated with a preponderance of less aggressive tumors
Disregulation does not appear to correlate strongly with aggressive tumor characteristics and is independent of total EGFR expression level.

Example 2

EGRF Endocytosis is Disregulated in Human Squamous Cell Carcinoma

Material and Methods

Cell Lines

Cell line identities were verified by SNP analysis. Cells were *mycoplasma* free and tested regularly. Cells were grown in Ham's F-12 media: DMEM supplemented with 10% FBS, 10 mM HEPES, 2 mM L-Glutamine, 1 mM Sodium pyruvate (Gibco, Invitrogen). Normal Human Embryonic Keratinocytes (HEKs) from neonatal foreskins were cultured as described in (11). HEK cultures were grown and maintained in low-calcium serum-free KC culture medium (Gibco, Invitrogen) supplemented with 2.5 µg EGF and 25 mg BPE. For basal conditions cells were grown for 3 hrs in complete media but without 10% FBS.

Antibodies

Primary Ab: AKT (C67E6; Cell Signaling Technology), Clathrin (BF-06; EXBIO) EGFR (528; Cell Signaling Technology), EGFR (31G7; Invitrogen), ERK2 (c-14; Santa Cruz), phospho-EGFR (Tyr1068, D7A5; Cell Signaling Technology), phospho-AKT (Ser473, D9E; Cell Signaling Technology), phospho-44/42 MAPK (ERK1/2, Thr202/Tyr204, E10, Cell Signaling Technology) and β-tubulin (2-28-33, Zymed). Secondary Ab: Alexa 488 goat anti-mouse IgG (A11001; Invitrogen), Alexa 594 donkey anti-rabbit IgG (A21207; Invitrogen), Alexa 594 goat anti-human IgG (A11014; Invitrogen), Alexa 594 goat anti-mouse IgG (A11005; Invitrogen), HRP-conjugated goat anti-mouse (F21453; Invitrogen), HRP-conjugated goat anti-rabbit (A10547; Invitrogen).

Fluorescent EGF Internalization Assay on Mouse Xenografts and Patient SCC Samples Tumor samples were collected, with PA Hospital consent and ethics approval, on ice either from PAH Pathology (post-surgery) or from procedure room (biopsy). Samples were sliced into ~1 mm sized pieces and washed three times for 10 min in basal media at 4° C. 20 ng/mL of EGF-Alexa488 (E-13345; Invitrogen) was added to the final wash for 5, 15 or 30 min and placed at 37° C. In addition, sample was left untreated, treated with 25 µg/mL of cetuximab (Erbitux; MerckSerono) for 30 min prior to addition of EGF for 15 min or treated with 10 µg/mL Tfn-Alexa$^{555}$ (Invitrogen, T-35352) or 10 µg/mL Dextran-Alexas94 (Invitrogen, D-22913). Samples were washed five times at 4° C. in PBS+0.1% Triton X-100 (PBTX) for 30 min and then fixed in 4% PFA/PBS overnight (O/N) at 4° C. Samples were washed twice in PBS and placed in 100% MeOH at 4° C. for 2 hrs. Tissue autofluorescence was reduced using Dent's bleach (4 MeOH: 1 DMSO: 1 30%1-1202) (12) for 2 hrs at room temperature (RT). Samples were rehydrated using a methanol/PBTX series. Samples were incubated with DAPI (50 mM) for 10 min, washed for 2 hrs with PBTX, washed twice in PBS, rinsed with $H_2O$ and mounted in Prolong Gold (Invitrogen) on concave microscope slides. Images were acquired using a Zeiss 510 Meta confocal with a 63× objective with Zen 2008 software.

Whole Mount Immunofluorescence (IF) on Patient SCC Samples

Whole Mount samples were processed as described above however following bleaching step, samples were blocked for 4 hrs in 10% horse serum/PBTX and incubated with primary Ab in block O/N at 4° C. Following 5×20 min washing in PBTX, the corresponding Alexa Fluor 594 secondary Ab in block was applied for 1 hr at RT. Samples were incubated with DAPI (50 mM) for 10 min, mounted and imaged as above.

Section IF and H&E Staining

Formaldehyde fixed tumor samples were paraffin embedded and sectioned at 4 µm. Sections were incubated in a heating oven (56° C.) for 1 hr prior to rehydration. For IF, sections were xylene treated and rehydrated through a standard alcohol series. Following antigen retrieval using pH 9.0 Tris-EDTA buffer sections were blocked in 4% Horse Serum/1% BSA/PBS for 1 hr at RT and primary Ab incubated O/N at 4° C. Following washes in block the Alexa fluor 488 secondary Ab was added for 1 hr at RT. After washing sections were DAPI stained and mounted as described above. Images were acquired using a Zeiss 510 Meta confocal with a 25× objective with Zen 2008 software. A standard H&E staining protocol was performed by Pathology Queensland at PA Hospital and images acquired on a Nikon Eclipse 50i microscope using a 4× or 20× objective.

Quantitative EGF Internalization Assay

The SCC cell lines were plated in 100 mm dishes at 80% confluency. A modified version of ligand internalization assay as described in (13) was performed to measure EGF internalization. After basaling cells were treated with 1 ng/mL of Biotin-EGF (E3477; Invitrogen) at 37° C. for 0, 5, 15 or 30 min. Internalization was stopped by placing cells on ice and washing with ice cold PBS. Non-internalized and membrane bound Biotin-EGF was blocked by washing with 1 µg/mL avidin (Sigma) followed by quenching with 10 µg/mL Biotin (Sigma). A non avidin-biotin blocked control was included to determine total EGF levels at 15 min. Cells were then washed three times in cold PBS and lysed in 150 µL of RIPA buffer containing protease and phosphatase inhibitors (Calbiochem). EGF levels were measured using Human EGF ELISA Kit (KHG0061; Invitrogen) with some modifications. Protein lysate (10 µg) in sample diluent and a two-fold dilution series (1 ng/ml to 15.6 pg/mL) of Biotin-EGF (standard curve) were plated onto a human EGF coated 96-well plate and incubated for 2 hrs. Following washes, streptavidin-HRP was added and the plate incubated for 30 min at RT. Stabilized Chromogen was added after washing and the plate incubated in dark. After 30 min a Stop solution was added to each well and absorbance was read at 450 nm. The assay was performed three times in technical duplicate.

Fluorescent EGF/Tfn Internalization Assay

Cells were plated at 80% confluency on coverslips. Following basaling cells were treated with 10 ng/mL of EGF-Alexa$^{488}$ or 25 µg/ml TFN-Alexa$^{555}$ at 37° C. for 5, 15 or 30 min or left untreated. Cells were washed three times in cold PBS and fixed in 3% PFA. After further washing cells were DAPI stained and mounted onto glass slides and imaged using a Zeiss 510 Meta confocal with a 63× objective.

EGFR level Elisa Assay

SCC cell lines and HEKs were plated in 100 mm dishes. Cells were washed three times in cold PBS and lysed in 1501.11 of RIPA buffer containing protease and phosphatase inhibitors (Calbiochem). EGFR levels were measured from 12-15 μg of total protein lysate using STAR EGFR ELISA Kit (Millipore). The assay was performed three times in technical duplicate. An unpaired Student's T-test was performed to compare levels of EGFR of each SCC lines compared to HEKs using GraphPad Prizm 5.

Immunoblotting

SCC cell lines were plated in 100 mm dishes at 80% confluency. After basaling cells were treated with 1 ng/mL of EGF-Alexa[488] at 37° C. for 5, 15 or 30 min or left untreated (control and EGFR). Cells were then washed three times in cold PBS and lysed in 4 mL lysis buffer [50 Mm Tris-HCl pH7.5, 100 mM NaCl, 1% Triton X-100, protease and phosphatase inhibitors (Calbiochem)]. For immunoblotting equal concentrations, as determined by BCA assay (Pierce), of protein lysates were separated by SDS-PAGE, semi-dry transferred to PDVF membranes (Millipore). Membranes were blocked in 2% BSA in TBS+0.1% Tween-20 (TBST) and probed with primary Ab O/N at 4° C. and then washed with TBST three times for 10 min. The membranes were incubated with corresponding secondary Ab in block for 1 hr. After washing the membranes were incubated with ECL (1:1 of Supersignal West Pico and Supersignal Dura; Thermo Scientific) and exposed to film (FUGI). Each experiment was performed three times.

Results

Ligand-dependent receptor endocytosis has not previously been examined in viable human tumors before. Therefore, the present inventors sought to develop a method in which one could image, in real time, EGFR endocytosis in viable human tumors. Previous studies have characterized EGFR endocytosis in established cell line models in two dimensional tissue culture systems (12). However, there are reports suggesting that the biology of receptor trafficking observed in vitro may not reflect receptor trafficking in vivo (13). In vivo, tumor cells exist within a three-dimensional micro-environment surrounded by non-transformed cells and connective tissue elements. Interactions between tumor cells and their stromal environment (cellular and non-cellular) will dictate cellular behavior and will likely influence receptor biology. Therefore, the present inventors developed a method to examine ligand-dependent EGFR endocytosis in ex vivo samples of fresh living human tumors.

Ligand-Stimulated EGFR Uptake can be Visualized in Live Xenograft Tissue

Figure 17:
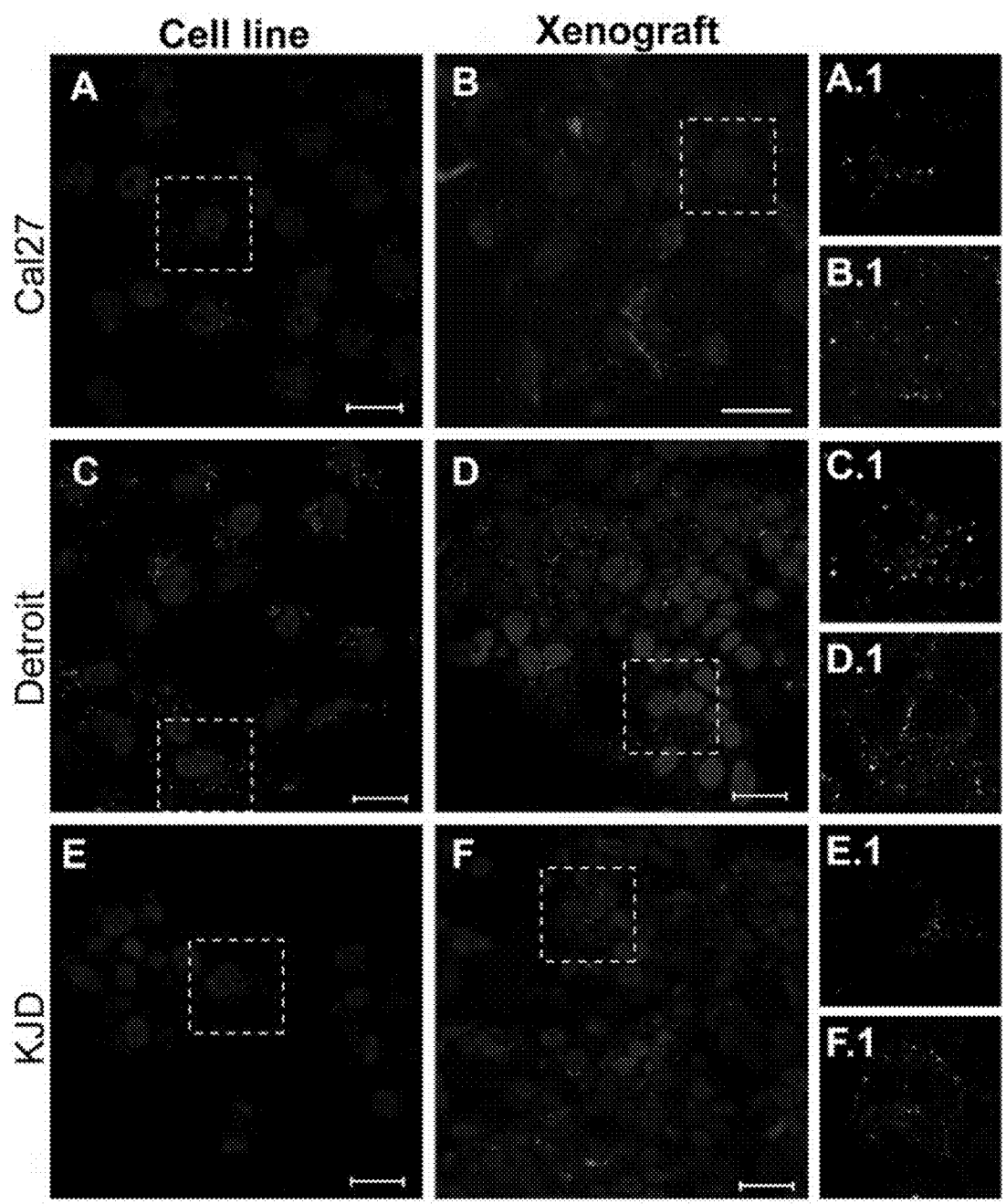
FIG. 17 is a photographic representation showing the distribution of EGF-Alexa$^{488}$ after 15 min stimulation in SCC cell monolayer is comparable to the SCC-derived mouse xenograft. (A, B) Images of Ca127 cell line and xenograft derived from Ca127 both stimulated with EGF-Alexa$^{488}$ for 15 min. Nuclei are shown in blue and EGF-Alexa$^{488}$ in green. (A.1, B.1) Higher magnification image of EGF-Alexa$^{488}$ of selected cell as indicated by the box corresponding to image A and B, respectively. (C, D) Images of Detroit cell line and xenograft derived from Detroit cells both stimulated with EGF-Alexa$^{488}$ for 15 min. (C.1, BA) Higher magnification image of EGF-Alexa$^{488}$ of selected cell as indicated by the insert corresponding to image C and D respectively. (E, F) Images of KJD cell line and xenograft derived from KJD cells both stimulated with EGF-Alexa$^{488}$ for 15 min. (E.1, F.1) Higher magnification image of EGF-Alexa$^{488}$ of selected cell as indicated by the insert corresponding to image E and F respectively. (Cell line: n=3; Xenograft: n=2, representative image shown). (Scale bars, 20 µm).

Prior to using human tumors the present inventors optimized their methodology using xenograft models of established SCC cell lines injected into NOD/SCID mice (14). Tumors were removed and processed as described in Materials and Methods for this example. After uptake the tissue was fixed and bleached as described. The samples were then mounted in microscopy wells and analyzed by confocal microscopy (FIG. 17). All xenograft tumors demonstrated specific EGF binding and varying degrees of receptor internalization at 15 min in vitro and in vivo (FIG. 17). The xenograft tumors showed similar uptake to their monolayer cultured counterparts.

Figure 18:
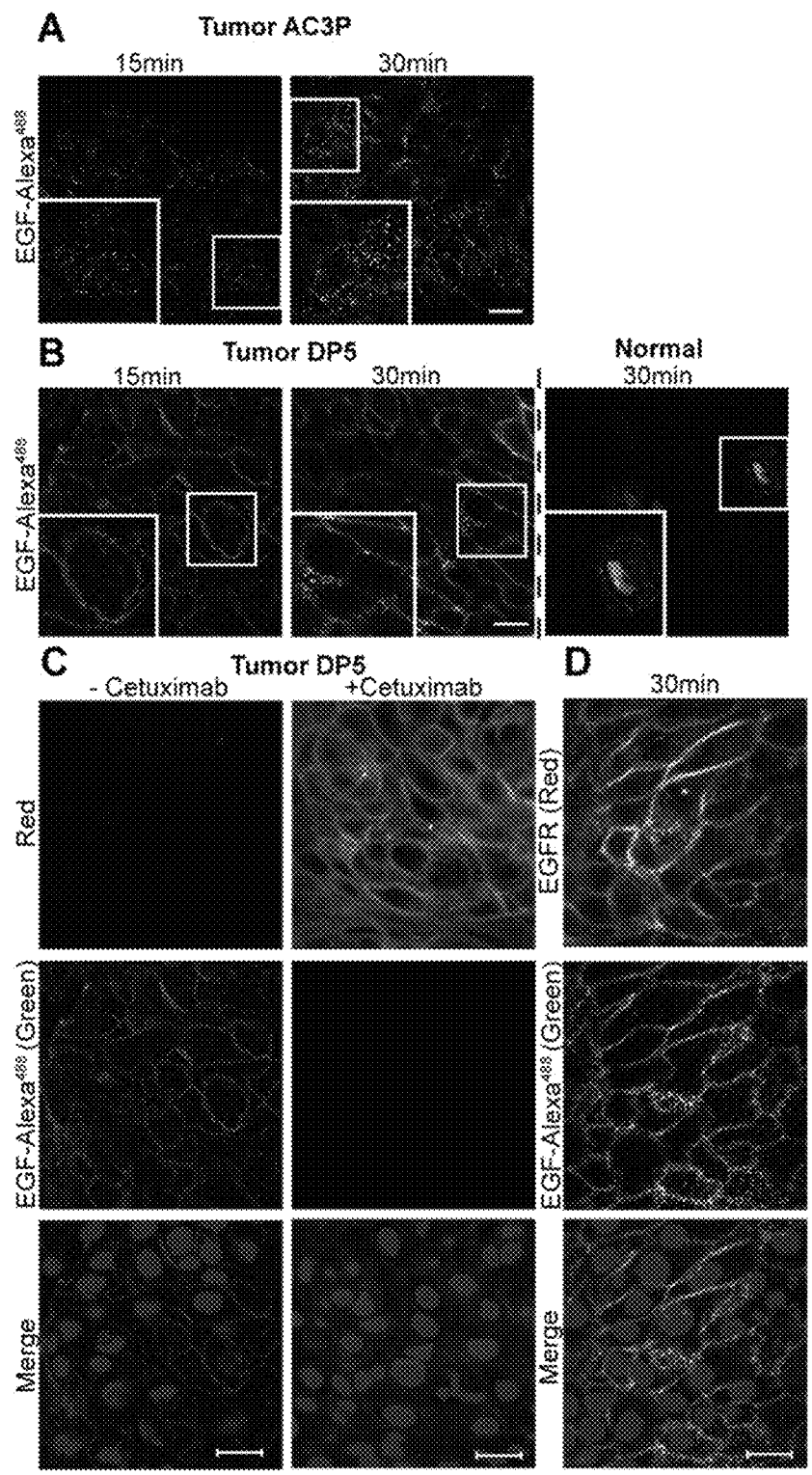
FIG. 18 is a photographic representation showing that internalization of EGF-Alexa$^{488}$ differs between patient SCC. (A) EGF-Alexa488 distribution in patient SCC after 15 min and 30 min stimulation. Inserts are higher magnification of the region shown by the smaller box. Uptake of EGF into endosomal structures is observed and this phenotype is seen in approximately 40% of patients (refer to table 1). (B) EGF-Alexa488 distribution in patient SCC after 15 min and 30 min stimulation. Inserts are a higher magnification image of the region indicated by the smaller box. Plasma membrane binding of EGF is observed but with little internalization. This is representative of approximately 60% of patients (see Table 1). EGF-Alexa$^{488}$ distribution in corresponding normal patient epithelial tissue is shown at 30 min. (C) Pre-treatment with cetuximab prior to EGF addition inhibits EGF binding. cetuximab was labeled post-fixation using anti-human Alexa 594 secondary. In the merged images cetuximab is shown in red, EGF in green and nuclei in blue. (D) Post-fixation labeling of the EGFR (red) shown in the merged image co-localizes with EGF ligand (green). (Scale bars, 20 µm).
Figure 19:
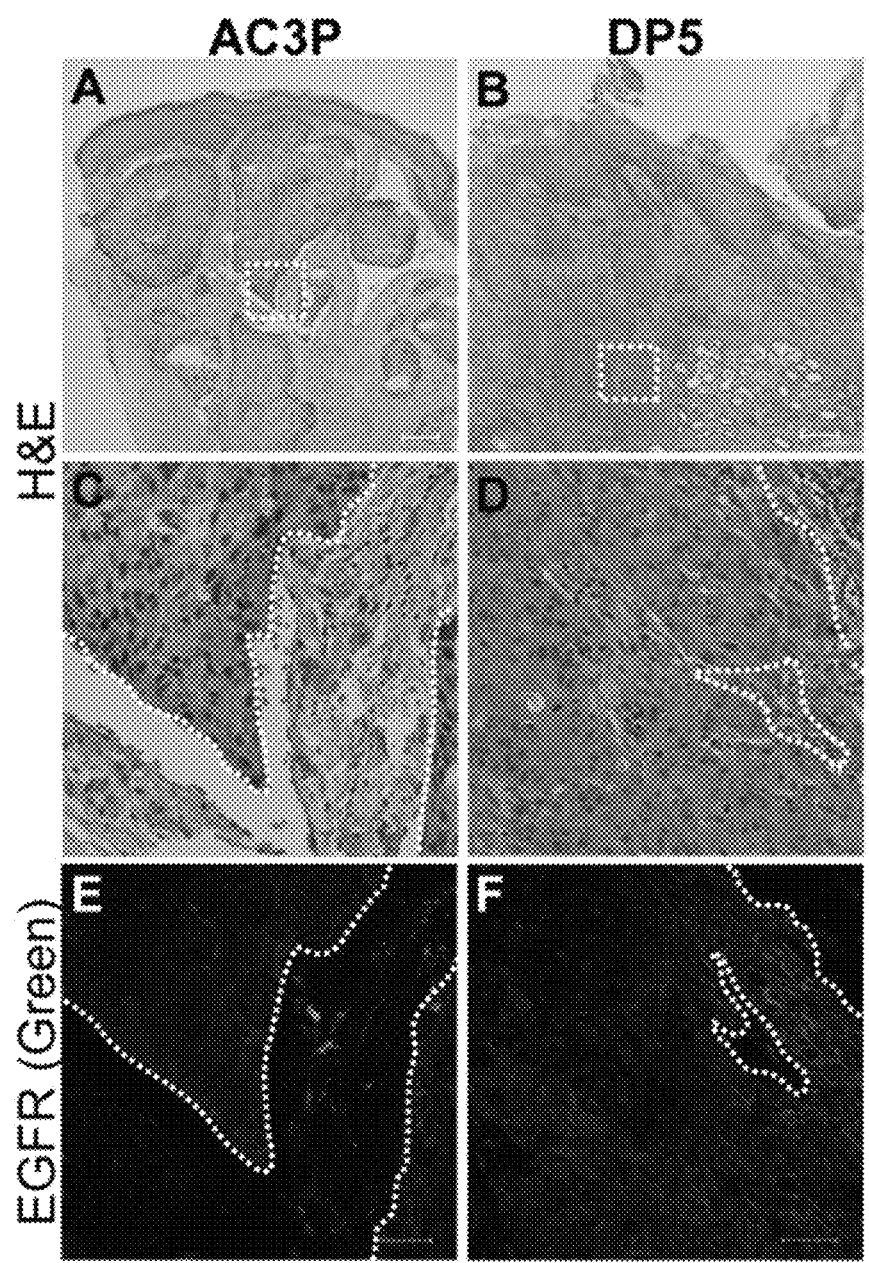
FIG. 19 is a photographic representation showing the dysplastic cells within patient SCC samples as identified by H&E staining over-express the EGFR. (A, B) H&E staining of 4 µm sections from patient tumors taken at 4× magnification (Scale bar, 200 µm). (C, D) 25× magnification images of region indicated by white box in panels A and B respectively. (E,F) Successive sections of C and D fluorescently labeled with EGFR (green) and DAPI stained (blue) (Scale, 50 µm).

EGFR Ligand-Induced Endocytosis is Disregulated in Approximately 60% of Human SCC Having validated their method in xenografts, the present inventors analyzed the ligand-dependent EGFR internalization in human tumors (FIG. 18). They examined eight viable SCC tumor samples excised at surgery or obtained from core biopsies. In these embodiments, tissue should be non-frozen, non-fixed and non-necrotic for uptake to occur. In three of the eight patients uptake of EGF into endosomal structures was observed, as shown for patient AC3P (FIG. 18A). Five of the eight tumors show plasma membrane binding of EGF but little internalization (FIG. 18B, Table 4), however after 30 min internalization is observed in a small subpopulation of cells (approx. 2-5% of total tumor cells). The lack of internalization cannot be attributed to the loss of viability of the patient samples since the present inventors were able to show both Dextran uptake and/or transferrin receptor (TfnR) internalization in these same samples. Non-viable samples showed no binding or uptake above tissue autofluorescent levels. Controls included no EGF addition and 4° C. To further validate the specificity of EGF fluorescence tumor samples were pre-incubated with high concentrations of cetuximab, the monoclonal antibody which binds to the ligand—binding domain of EGFR and is used in SCC therapy. It was found that prior binding of cetuximab prevented EGF-Alexa[488] binding and uptake (FIG. 18C). Post-fixation labeling of the samples with anti-EGFR showed co-localization with the EGF-Alexa[488] (FIG. 18D). Finally, to confirm that the EGF binding and uptake observed occurred only in the dysplastic/tumorigenic cells, serial sections of untreated tissue (formalin fixed on removal) samples for patients AC3P and DP5 were stained with Hematoxylin and Eosin (H&E) or fluorescently labeled anti-EGFR Ab. EGFR staining was demonstrable to detectable levels only in the dysplastic cells, as shown by the H&E staining (FIG. 19).

TABLE 4

TUMOR CHARACTERISTICS

| [a]ID | [b]Site | [c]EGF |
|---|---|---|
| RW2 | Tonsil | Plasma membrane |
| JT3 | Tongue | Plasma membrane |
| DP5 | Larynx | Plasma membrane |
| EG7 | Tonsil | Internalized |
| BV8 | Oral Cavity | Plasma Membrane |
| SW1P | Cutaneous | Internalized |
| AC3P | Cutaneous | Internalized |
| JM2P | Cutaneous | Plasma membrane |

Figure 20:
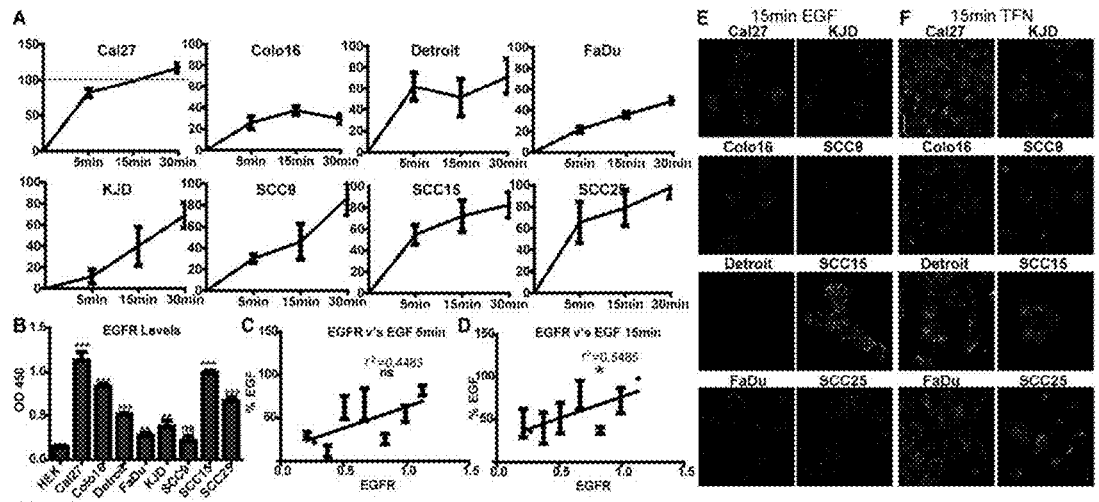
FIG. 20 is a graphical and photographic representation showing the rates of EGF internalization in SCC cell lines is variable and exhibit disregulation in initial uptake. (A) Biotin-EGF uptake was performed in SCC cell lines for the time points indicated. Endocytosis was measured as avidin inaccessibility as a percentage of total at 15 min. Assays were performed as described in Materials and methods. Data shown are the average of 3 experiments+/−SEM. (B) Levels of EGFR expression in SCC cell lines are increased compared to HEK cells. Equal protein concentrations of SCC and HEK cell lysates were subjected to ELISA assay for EGFR levels (Materials and Methods). Data shown are an average of 3 experiments+/−SEM by non-paired T-test. *: P<0.001; : P<0.01; *: P<0.05. ns: no significance. (C and D) Correlation graphs of internalized EGF (y-axis) versus EGFR expression level (x-axis) at 5 minute (C) and 15 minute (D) time points of EGF internalization. (E and F) EGF-Alexa$^{488}$ (E) or Tfn-Alexa$^{594}$ uptake was performed in SCC cell lines as described in Materials and Methods. Coverslips were fixed and imaged by confocal microscopy at 15 min.

[a]De-identified patient code
[b]Site from which tumor was excised
[c]Status of ligand-induced EGFR endocytosis after EGF stimulation EGFR Internalization in SCC Cell Lines is Disregulated in the Initial Receptor Concentration and Recruitment Stages of Endocytosis Next, the present inventors examined whether there was a relationship between ligand-dependent EGFR trafficking status and EGFR expression levels or ligand-induced signal transduction. Both human SCC samples as well as established human SCC cell lines were shown to display varying degrees of ligand-dependent EGFR internalization dysfunction (FIGS. 17 and 18). Thus, the SCC cell lines are a useful model to interrogate the relationship between EGFR internalization dysfunction and EGFR expression or signaling activity. Low concentrations of recombinant EGF ligand were used to ensure that uptake was mediated via clathrin-coated pits (15). For each of the indicated cell lines the internalization of biotinylated EGF was measured using standard endocytosis assays as described (Materials and Methods for Example 2). Receptor internalization, as a percentage of total EGF binding at 15 min, was measured over a 30-min time-course for each cell line (FIG. 20A). Fifteen minutes was chosen as the time-point for measurement of total binding as after this time-point degradation of the receptor increases. Ligand-stimulated EGFR internalization in the first five minutes provides an estimate of the initial rate of ligand binding and the efficiency with which ligand binding stimulates receptor endocytosis. In contrast, internalization measured at 15 min reflects the relative capacity of the cells to bind and internalize the EGFR. The eight human SCC cell lines varied considerably in their ability to bind and internalize ligand within five minutes and interestingly showed less disregulation than the human tumor samples, reflecting previously observed differences between cell line responses in culture as opposed to xenograft or tumor models (16).

Disregulation of EGFR Internalization does not Correlate in the Initial Stages with EGFR Expression Level EGFR expression level in each cell line was measured by ELISA assay (FIG. 20B). There was no correlation between EGFR expression and initial rates (5 min) of EGF-dependent receptor internalization (FIG. 20C). However, there was an association between EGFR expression levels and the total capacity (15 min) of the cell lines to internalize EGFR (FIG. 20D). EGF-Alexa$^{488}$ was added to the cells on coverslips as for Biotin-EGF in biochemical experiments. Time points were fixed and imaged. Immunofluorescence uptake in each cell line correlated with the assay levels of uptake (FIG. 20E). Thus, initial rate constants for ligand binding and internalization appear to be independent of receptor number suggesting that proximate effects associated with coupling of ligand binding and internalization may be disregulated within SCCs.

Figure 21:
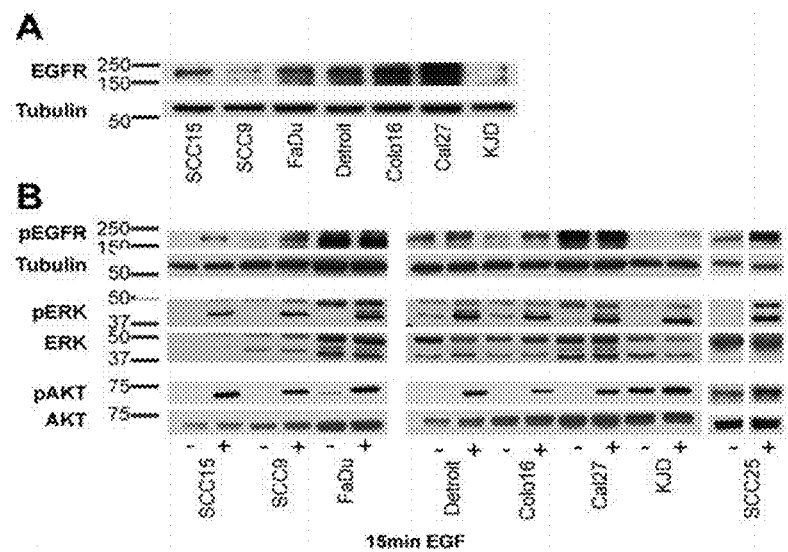
FIG. 21 is a photographic representation illustrating that SCC cell lines show differing levels of activation of the EGFR and downstream pathway signaling targets. (A) Western analysis of SCC cell lysates. 10 µg of cell lysates indicated were loaded per well. Levels of EGFR expression are shown along with tubulin loading control. (B) Western analysis of EGFR phosphorylation, AKT phosphorylation relative to total AKT and ERK phosphorylation relative to total ERK levels. Cells were basalled by incubation for four hours in serum free media or basalled and then stimulated with low concentration of EGF (1 ng/mL) for 15 min then washed in cold PBS. Cell lysates were prepared as described in Methods and subjected to SDS-PAGE and Western analysis. Full time-courses of stimulation were completed and analyzed.

Disregulation does not Correlate with any Single Signaling Defect but does Correlate with Pathway Defects The uncoupling of EGFR expression and initial internalization rates is suggestive of defects in ligand-induced recruitment into clathrin coated vesicles (CCVs) or disregulation of CCV formation. However, analysis of TfnR internalization showed normal uptake suggesting the defect in endocytosis is specific to the ligand-induced uptake of EGFR in the SCC cell lines (FIG. 20F). These data show that the disregulation is not a global defect in ligand-dependent receptor endocytosis. Defects in ligand-dependent receptor endocytosis would be expected to be reflected in defects in ligand-induced signaling events. Therefore, all cell lines were examined by Western analysis for signaling output (FIG. 21). Cells were stimulated with EGF as described for the endocytosis assays above over the same time-course. Three biological replicates were probed for each time-point and for each cell line. Lysates were probed for EGFR, phospho-EGFR, tubulin, total ERK, phospho-ERK, total AKT and phospho-AKT (FIG. 21). Although large variability in signaling between cell lines was observed, no correlation between this and EGFR levels was observed and no single signaling alteration correlated with endocytic defects.

Analysis indicated no clear relationship between constitutive phosphorylation of the EGFR and EGFR internalization rate or capacity (FIG. 21). There was no association between the ability of ERK and AKT to respond to EGF binding and EGFR internalization rates or capacity (FIG. 21). There was no correlation between the expression of total AKT or ERK levels and EGFR internalization rates or capacity (FIG. 21). A similar relationship was observed in the xenograft samples examined by immunohistochemistry for phospho-AKT. These data suggest that ligand-dependent EGFR internalization is not due to a single defect in ligand-stimulated EGFR phosphorylation or ligand-coupled ERK and AKT signaling.

However, each cell line which showed EGFR internalization changes also had one or more alterations in signaling; thus changes in EGFR internalization may be an overall biomarker for signaling pathway disruption due to the intricate feedback mechanisms.

Figure 22:
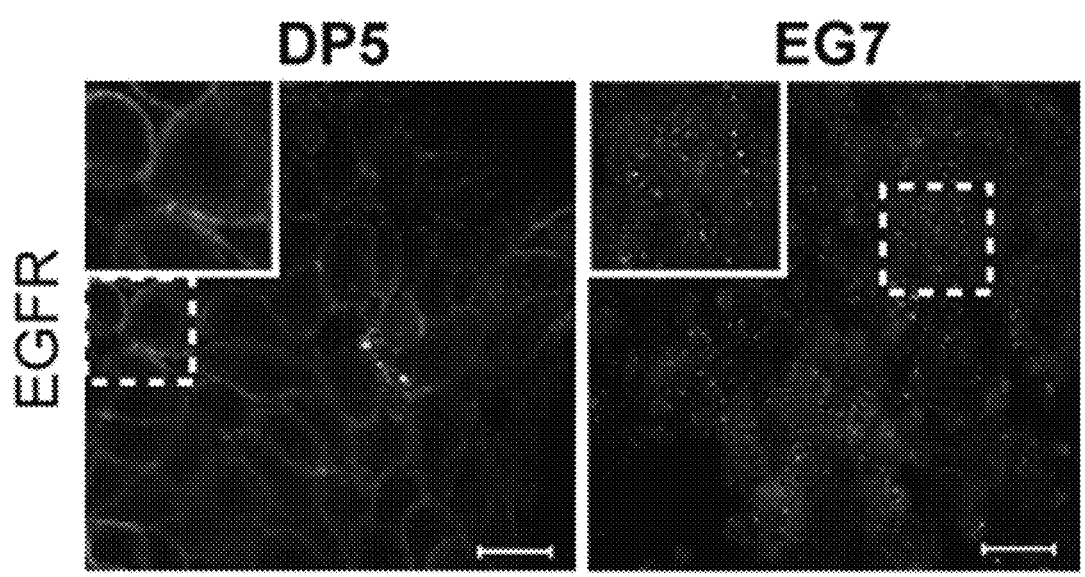
FIG. 22 is a photographic representation showing that EGFR staining can be used as a marker to visualize endocytosis differences in patient samples stimulated with EGF ligand. Samples DP5 and EG7 have been stimulated with EGF ligand for 30 min prior to fixation and EGFR labeling. Post-fixation labeling of the EGFR is shown. Inserts are a higher magnification of the region indicated by the smaller box. (Scale bars, 20 µm).

Disregulation of EGF Internalization can be Visualized Using Post-Fixation EGFR Labeling of Pre-Stimulated Tissue Finally, the present inventors examined whether receptor trafficking defects in tumor samples can be visualized in normal histopathological specimens. In particular, they tested post-fixation labeling of tumor samples stimulated with EGF for 15 min, processed the tissue as described in materials and methods for the present example and labeled the sample with anti-EGFR Ab (FIG. 22). Stimulation was carried out simply by adding EGF to fresh tumor samples in serum free media. Localization of the EGFR, as observed by post-fixation labeling, reflected the results the present inventors had observed with direct imaging of the EGF ligand (FIGS. 18A and B). Thus, after stimulation, labeling of the EGFR can also be used to classify SCC as endocytosis competent or disregulated with the advantage of increased fluorescence from secondary Ab labeling as opposed to direct labeling of the EGF.

Discussion

Substantial international effort has gone into proteomics, genomics and transcriptomics to try to determine a correlation between patient response to anti-EGFR therapy and tumor biology. However, it has not been possible to characterize the trafficking and spatiotemporal regulation of receptors in human tumors. The present inventors have developed a method to investigate ligand binding and receptor-mediated endocytosis of EGF/EGFR in human tumor samples in an ex vivo context. They have demonstrated that EGFR endocytosis is frequently disregulated in human SCC. Interrogation of human. SCC cell lines also revealed disregulation of EGFR endocytosis which appeared to impact the initial stages of ligand-induced recruitment of EGFR. Finally, EGFR endocytic dysfunction showed no single correlation with EGFR expression level, EGFR phosphorylation or with the activation of downstream effectors such as AKT or ERK but EGFR endocytic disregulation may be a biomarker for overall signaling dysfunction. This now enables one to examine the potential relationship between EGFR trafficking and prognosis, tumor progression and EGFR inhibitor resistance and acquired resistance in epithelial tumors.

In particular, the present inventors found that in 60% of the human SCC tumors EGFR is not endocytosed in response to ligand induction. Breakdown of endocytosis in the oncogenic activation of receptor tyrosine kinases (RTKs) has been reviewed in detail recently (17) and has been highlighted in a recent report showing enhancement of tumorigenesis via RTK MET is dependent on its endocytic rates and localization (18). In cells where EGFR levels are enriched at the plasma membrane EGF stimulation results in sustained activation of both MAPK and PI3K pathways (17). Under hypoxic conditions many RTKs exhibit prolonged activation and while the mechanism for this is unknown the effect is increased oncogenesis (19). Thus it may be that inhibition of EGFR internalization is a mechanism of oncogenesis or progression.

The instant analysis of endocytosis in SCC cell lines shows that the main disregulation of EGFR uptake occurs in the initial 5 min after ligand addition. This fits with the inventors' observations in human tumors where receptor-mediated internalization of EGFR from the plasma membrane does not occur. The initial stage of stimulation corresponds to the time taken for recruitment of activated EGFR from membrane domains to the CCVs and encompasses EGFR oligomerization, ubiquitination, alterations in cortical actin and the diffusion of EGFR away from lipid-rich domains. Consistent with this no alteration in the internalization of the constitutively endocytosed TfnR was found, suggesting that clathrin-mediated endocytosis remains functionally intact.

The present analysis of EGFR expression level and signaling in SCC cell lines indicates that endocytic disregulation does not correlate with EGFR expression level in the recruitment phase. Cells with normal endocytosis also tended to show normal signaling outputs while cells with disregulated internalization had disrupted signaling output. However, no single signaling output could be correlated to endocytic disregulation. Increased expression of other Erb-B receptor family members and changes in cholesterol levels leading to increased lipid rafts would also affect EGFR retention on the plasma membrane. As therapies are directed against the EGFR itself, this alteration in localization and exposure of the EGFR will likely impact therapeutic response (20) and it may be that diagnosis of the endocytic capacity of EGFR in response to ligand binding in epithelial cancer will function as an overall biomarker for a number of intracellular changes leading to alteration in therapy response or tumor progression.

Example 3

Manipulation of EGFR Trafficking for Improving Anti-EGFR Monoclonal Antibody Therapies Materials & Methods Cetuximab Mediated Growth-Inhibition MTS Assay The Cetuximab mediated growth-inhibitory effect was measured by the CellTiter96 Aqueous One Solution Cell Proliferation Assay (Promega). A431 cells (number=1000, 2500 and 5000 per well) were seeded in 96-well flat bottom plates and incubated overnight to allow adherence. The cells were then exposed to cetuximab at various concentrations ranging from 0 to 100 µg/mL for 48 hours. 20 µL MTS reagent was added into each well and incubated at 37° C. in 5% $CO_2$ for 2 hours. The optical density (OD value) was read at 490 nm by a microplate spectrophotometer. The percentage cell growth was indicated by comparison of OD value of treated cells versus untreated controls.

Cetuximab Mediated ADCC MTS Assay

The Cetuximab mediated ADCC effect was measured by the CellTiter96 Aqueous One Solution Cell Proliferation Assay (Promega). Target cells (A431, number=2,500 per well) were seeded in 96-well round bottom plates and allowed to settle down for 2 hours. The target cells were then incubated with effector cells (PBMCs) at E/T (effector/target) ratios of 50/1 with/without cetuximab (60 µg/mL) at 37° C. in 5% $CO_2$. After 24 hours incubation, 20 µL MTS reagent was added into each well and incubated at 37° C. in 5% $CO_2$ for 2 hours. The optical density (OD value) was read at 490 nm by a microplate spectrophotometer. The percentage of cell viability was indicated by comparison of cetuximab-treated versus untreated cells.

Flow Cytometry-Based ADCC Assay

Flow cytometry was performed on triplicate tubes per treatment. Target cells were harvested and labeled with 0.5 µM CFSE (Life technologies) for 10 minutes, followed by washing to remove excess dye. The CFSE labeled target cells were then plated at a concentration of 20,000 cells per tube and incubated with 60 µg/mLs Cetuximab and fresh PBMCs (E/T=50/1) for 4 hours. 30 µM Dyngo4a was added at given time points as described in figure legends. After the incubation, 5 ul of 7-AAD (BD Pharmingen) was added into each tube to indicate the target cells that were killed. Samples were analyzed by flow cytometry (BD FACSCanto). The percentage of specific target cell death was calculated using the following formula:

$$\% \text{ Specific Cell Death} = \frac{[\%7\text{-}AAD^+CFSE^+ \text{ (dead) targets}] - [\% \text{ spontaneous } 7\text{-}AAD\ CFSE \text{ (dead) targets}]}{100 - [\% \text{ spontaneous } 7\text{-}AAD^+CFSE^+ \text{ (dead) targets}]} \times 100\%$$

Immunofluorescence of Dyngo4a Inhibitory Effect

A431 cells were seeded on-coverslips in 12-well plates and incubated overnight to reach 80% confluence. The cells were treated with different concentrations of dynasore (0 and 30 µM) for 30 minutes after a 3 hour-serum starvation, followed by 15 minutes EGF-Alexa$^{488}$ (100 ng/mL) uptakes. The EGF uptakes were stopped by three times washing in ice cold PBS. The cells fixed in 4% PFA/PBS for 30 minutes and washed three times in PBS before 30 minute-DAN staining. The coverslips were mounted on slides in Prolong Gold (Life technologies). Images were acquired using a Zeiss 510 Meta confocal with a 63× objective.

Immunofluorescence of Cetuximab-EGFR Internalization

A431 cells were seeded on coverslips in 12-well plates and incubated overnight to reach 80% confluence. The cells were incubated with 60 µg/mL Cetuximab for 4 hours. 30 µM dyngo4a was added at given time points as described in figure legends. The cells were then washed three times in ice cold PBS and fixed in 4% PFA/PBS for 30 minutes, followed by permeabilization in 0.1% TritonX/PBS (PBTX) for 20 minutes. Cetuximab was labeled by incubation with a secondary antibody (Alexa$^{647}$ goat anti-human IgG, Life technologies) for 1 hour, followed by 2% BSA/PBS blocking and 30 minute-DAPI staining. The coverslips were mounted on slides in Prolong Gold (Life technologies). Images were acquired using a Zeiss 510 Meta confocal with a 63× objective.

Results

The present inventors correlated EGFR trafficking and MHC I & II expression in SCC cells since MHC molecules play an important role in tumor cell evasion of the immune system. In particular they tested whether inhibition of endocytosis caused altered MHC I & II levels and/or distribution in A431 cells versus HeLa cells by immunofluorescence (IF). These cell lines were chosen as A431 are an SCC cell line with high EGFR expression levels and are oncogenically addicted to RTK signaling. A431 cells are also used as a model cetuximab sensitive cell line with regards to inhibition of proliferation (21, 22). HeLa cells are non SCC cell lines which have no up-regulation of the EGFR.

Dynasore, a cell-permeable dynamin inhibitor (23, 24), was used to manipulate EGFR trafficking. The large GTPase dynamin is important for endocytosis, since it functions a key mediator in clathrin-coated vesicle formation at plasma membrane (23). Dynasore is a small molecule that inhibits the GTPase activity of dynamin and therefore capable to completely block dynamin-dependent endocytosis at an intermediate stage by arresting the vesicles at plasma membrane (24). Dynasore has been commonly used in endocytosis studies (23-26), it acts fast (seconds) and in vitro its inhibitory effect can be reversed by washout (23). The dynasore protocol was designed according to a previous study, in which the dynasore mediated endocytosis inhibition in HeLa cells was dose dependent with an IC50 around 15 μM (23). EGF-Alexa$^{488}$ uptake was conducted to monitor the translocation of EGF-bound EGFRs in ligand-induced internalization.

Figure 23:
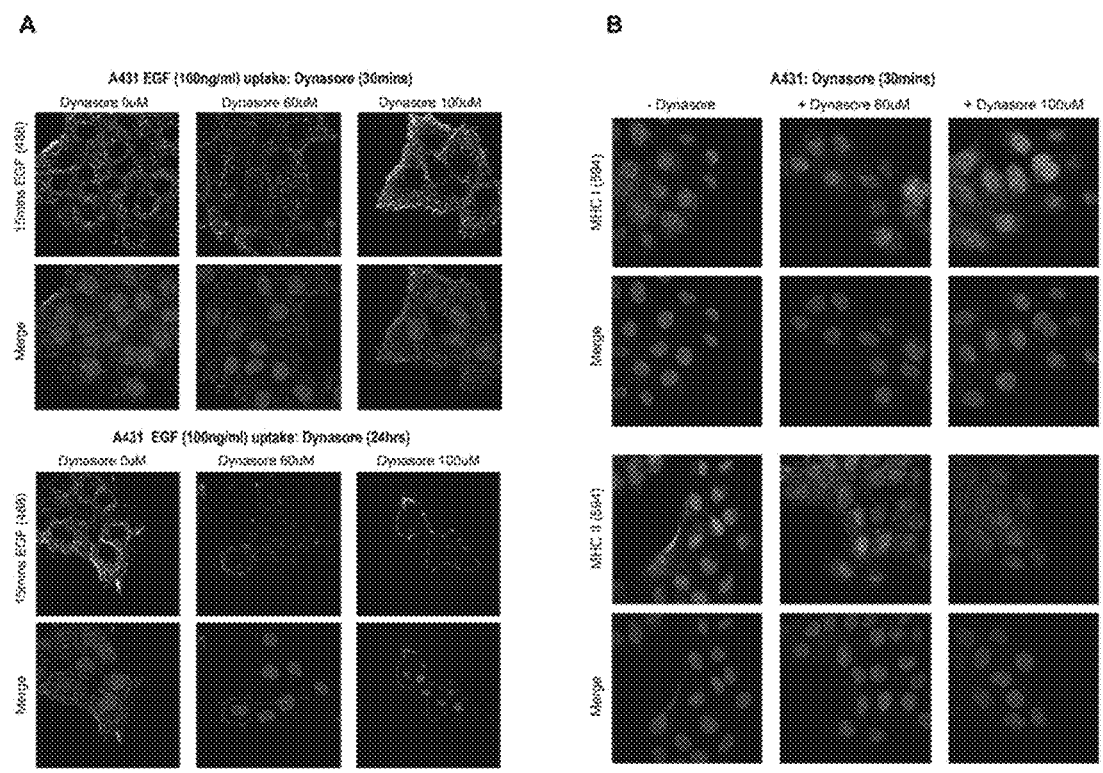
FIG. 23 is a photographic representation showing example panels for correlation between inhibited EGFR endocytosis and MHC class I and class II status. (A) Immunofluorescence showing manipulation of EGFR trafficking using a dynamin inhibitor. A431 cells were serum-starved for 3 hours and then treated with different concentrations of dynasore (0, 60 and 100 µM) for 0.5 and 24 hours. 15 minutes EGF-Alexa488 (100 ng/mL) uptakes were performed to monitor the trafficking of the ligand bound EGFRs (in green). The nuclei are shown in blue. (B) immunofluorescence showing changes in MHC class I and class II distributions caused by altered EGFR trafficking. A431 cells were treated with different concentrations of dynasore (0, 60 and 100 µM) for 0.5 hours, followed by fixation and permeabilization. MHC class I and class II were then labeled with primary antibodies PE-HLA-ABC and PE-HLA-DR, respectively, followed by secondary antibody labeling (Alexa 594). MHC I and II are shown in red while the nuclei are shown in blue.

FIG. 23A shows that dynasore successfully functioned as an endocytosis inhibitor resulting in increased EGFR levels accumulating on the plasma membrane when compared with the dynasore negative control. The upper panel of FIG. 23B shows increasing MHCI signal with increasing addition of dynasore while the lower panel shows a decrease in MHCII signal. Over an analysis of different experimental conditions, including with or without EGF, dynasore, IFNγ and Triton permeabilization, comprising multiple panels the present inventors concluded the following:

In A431 Cells:
  Addition of IFNγ had no effect on overall results obtained, but did increase total levels of MHC expression allowing easier visualization.
  A slight decrease in plasma membrane staining of MHCI was observed after EGF stimulation. Plasma membrane levels of MHCI were no longer detectable when EGF stimulation was coupled with dynasore inhibition. This was of interest as high levels of EGFR expression in SCC may lead to loss of surface expression of MHCI, increasing tumor evasion.
Dynasore 24 Hour Treatments:
  In A431 cells dynasore treatment over 24 hours showed cellular nuclear condensation (FIG. 24A lower panel) while HeLa cells appeared apoptotic or to have cytokinetic defects.

Figure 24:
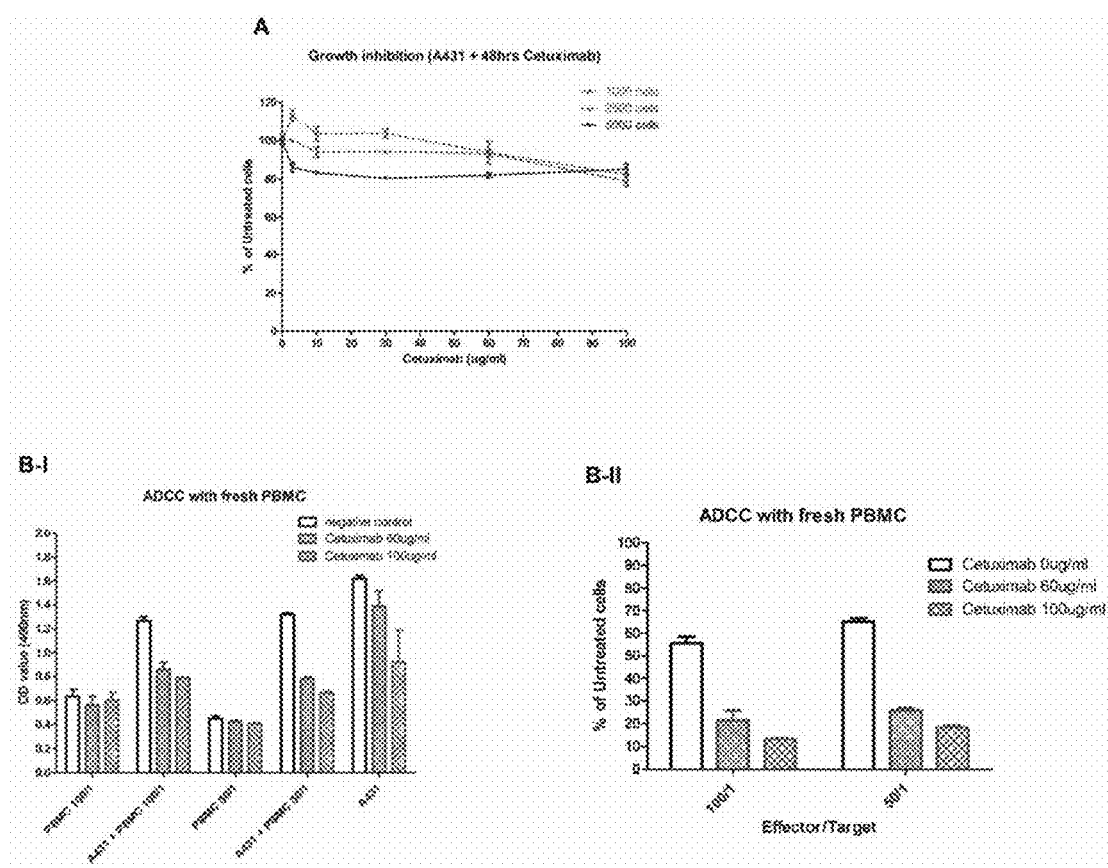
FIG. 24 is a graphical representation showing that cetuximab did not show a clear growth inhibitory effect, but triggered antibody dependent cellular cytotoxicity (ADCC) against A431 cells. (A) For the growth-inhibition assays, A431 cells (number-1000, 2500 and 5000 per well) were incubated with various concentrations of cetuximab (0, 3, 10, 30, 60 and 100 µg/mL) for 48 hours. MTS assays were performed to measure absorbance at 490 nm. The cell viability is presented as the percentage of untreated viable cells. (B-I, II) For the ADCC assays, A431 cells (number=5000 per well) were incubated with fresh PBMCs at different E/T ratio of 50/1 and 100/1 in the presence of 60 µg/mL cetuximab for 48 hours. (B-I) MTS assays were performed to measure absorbance at 490 nm. (B-II) The target cell viability is presented as the percentage of untreated viable cells and calculated following the formula.

To investigate the main effector of cetuximab induced response in cell lines, the present inventors tested the effect of cetuximab on tumor cells as a single treatment and also in the presence of immune effector cells. A431 cells which have been used as a cetuximab sensitive cell line in previous studies were first challenged with cetuximab alone for 48 hours. Cell viability was measured using the MTS assay to indicate growth inhibition effect. Overall cetuximab did not induce a significant cell viability reduction in a dose-dependent manner (FIG. 24A). Although cetuximab showed more inhibitory effect on A431 with increasing cell number, this may be due to the cell culture reaching 100% confluence during the treatment causing contact inhibition of growth. Then, A431 cells were treated with cetuximab in the presence of PBMCs (peripheral blood mononuclear cells) isolated from fresh whole blood of healthy volunteers for 48 hours. Cell viability was measured using MTS assay to indicate ADCC effect. FIG. 25B shows that cetuximab induced ADCC effect against A431 cells. Interestingly, 100 μg/mL cetuximab did not cause a significant increased cell viability reduction compared with 60 μg/ml. This may be due to fact that the concentrations used in the experiment were both much higher than the effective concentration (10-0.01 μg/mL) that has been reported in the literature (27), suggesting additional experiments may be needed for dose optimization. The above results lead to a conclusion that the cetuximab effect is more immune response dependent, rather than signaling inhibition dependent in our A431 cells.

Next, the present inventors tested cetuximab mediated ADCC against A431 cells in the presence of the dynamin inhibitor, dyngo4a, using an MTS assay. Of note, Dyngo4a alone and with cetuximab did not cause large cell viability reduction in PBMCs compared with the negative and cell death (10% Triton) controls (FIG. 25A-II), but cells lost more viability when cetuximab and Dyngo4a were added in combination, as compared with cetuximab single treatment (FIG. 25A-III).

Example 4

Figure 27A:
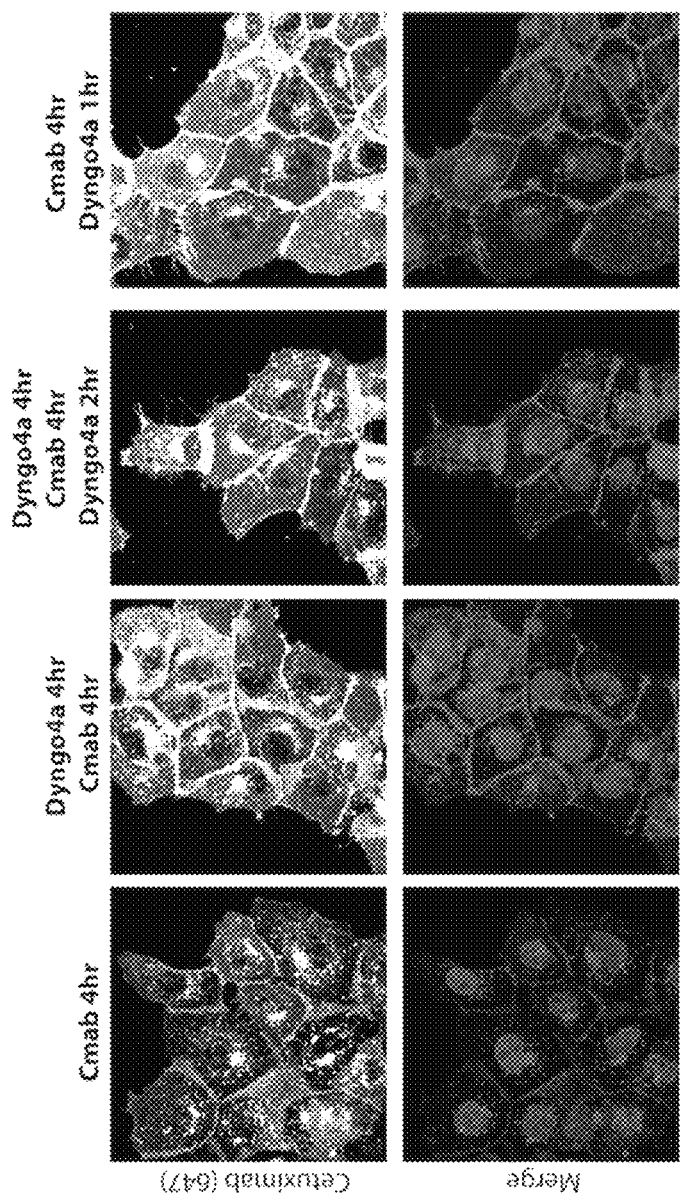
Figure 27B:
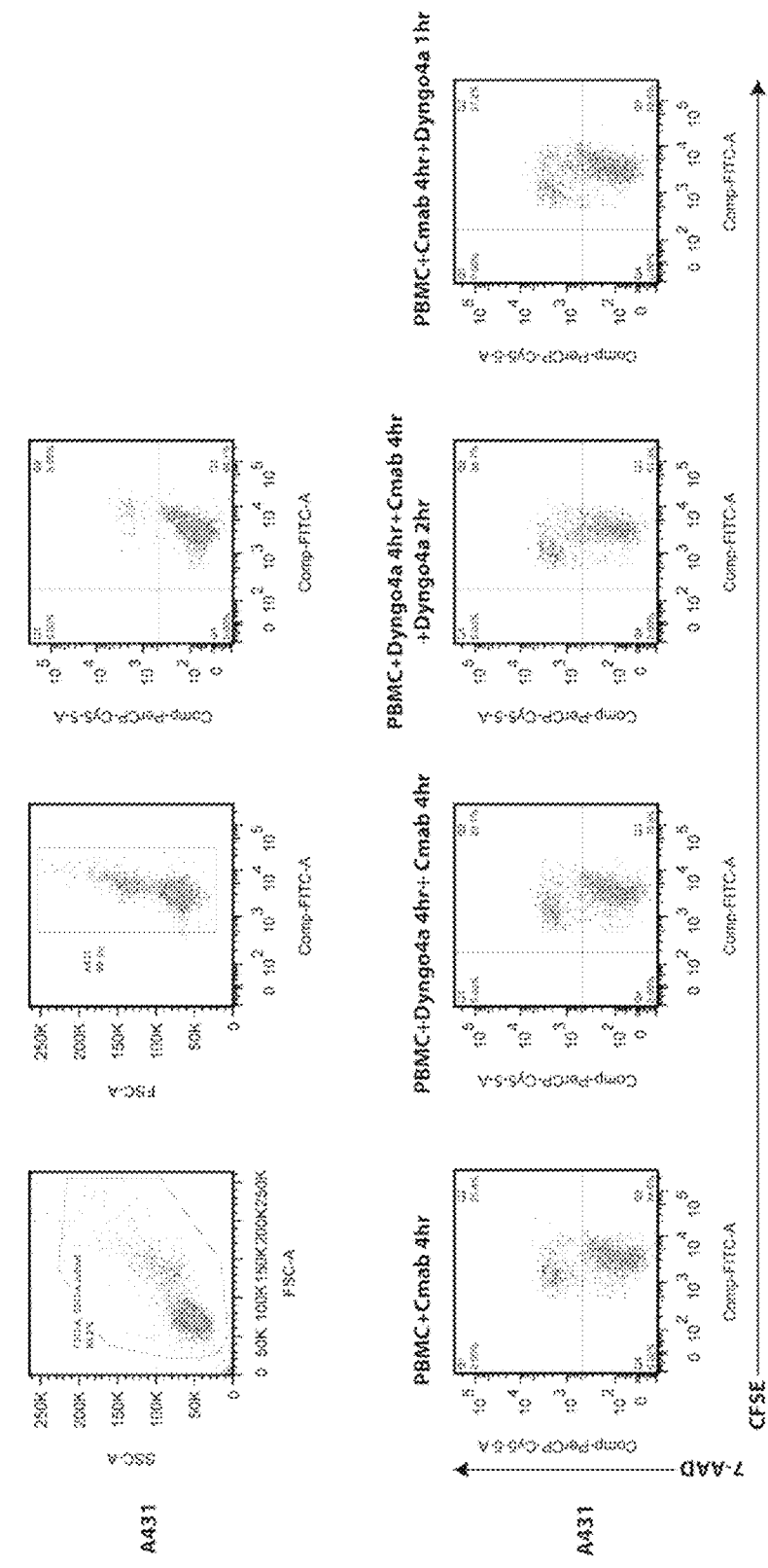
Figure 27C:
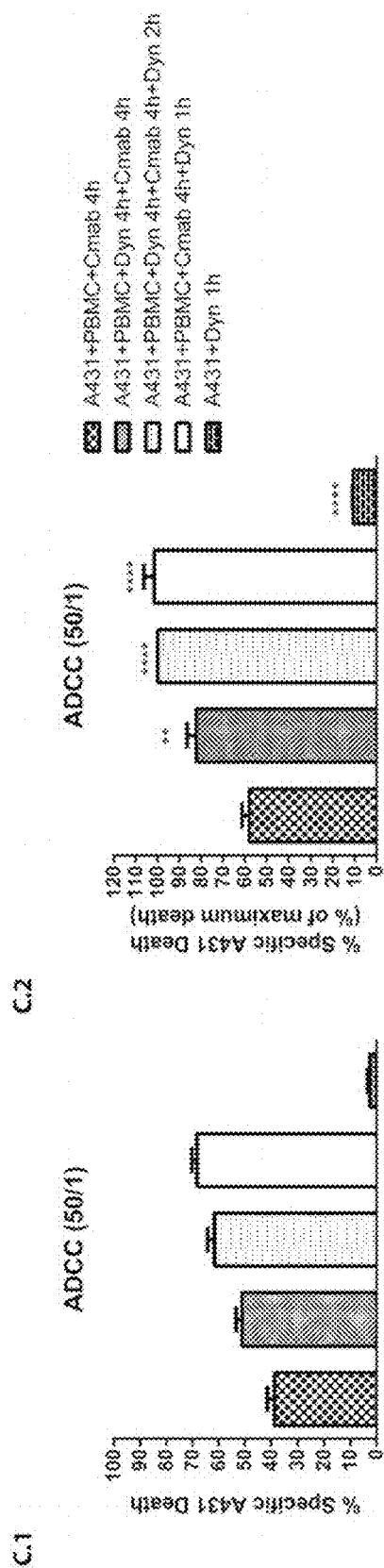
Figure 28C:
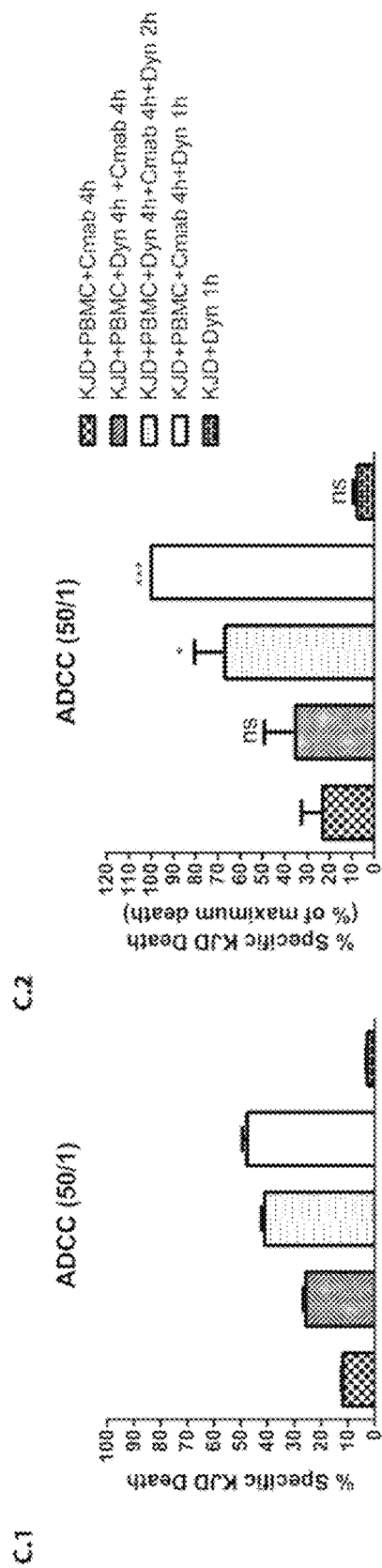

Dynamin Inhibitor, Dyngo4a, Significantly Improves Efficacy of Anti-EGFR Monoclonal Antibody Therapy on Cells with Increased EGFR Internalization Comparison experiments were performed on the cetuximab binding cell line, A431 (FIG. 26, FIG. 27A), and also a cell line, KJD, which showed low levels of plasma membrane bound cetuximab (FIG. 26, FIG. 28A) for further analysis. The present inventors' hypothesis predicted that if EGF-stimulated EGFR trafficking was inhibited, this would result in a proportional increase in plasma membrane levels of EGFR and a similar proportional increase in ADCC. Accordingly, the effect of a reversible small molecular weight inhibitor of dynamin, Dyngo4a was tested on cetuximab-induced ADCC in both A431 cells and KJD cells. FIG. 27A shows that in A431 cells cetuximab can be localized both to the plasma membrane and internalized structures over the 4-hour time-course of the ADCC assay. Cetuximab is still surface exposed at 4 hours which would allow ADCC. Addition of Dyngo4a increases surface levels of cetuximab and decreases internalized levels. FIGS. 27B and 27C show that approximately 38% of A431 died as result of cetuximab-induced ADCC. As predicted, inhibition of EGFR endocytosis by Dyngo4a increased the plasma membrane levels of EGFR and resulted in an increased level of cetuximab-induced ADCC. ADCC assay repeat experiments were expressed as % of maximum specific tumor cell death to allow statistical analysis across multiple assays. The data show that a significant increase in specific tumor cell death was observed across multiple protocols of Dyngo4a addition, with addition of the highly reversible Dygno4a during the last hour of the 4 hours ADCC assay showing highest efficacy. MD cells are resistant to cetuximab mediated ADCC. As predicted, KJD cells, which express low levels of EGFR on the plasma membrane after a 4 hour incubation with cetuximab (FIG. 28A), display relatively low levels of cetuximab-induced ADCC (approximately 10% cell killing; FIGS. 28C.1 and C.2). Addition of IgG isotype control in place of cetuximab showed no improved ADCC above PBMC alone (data not shown). Significantly, incubation with Dyngo4a increased the plasma membrane expression of EGFR (FIG. 28A) and increased cetuximab-induced ADCC to greater than 40% cell killing (FIGS. 28C1 and 4C2). Dyngo4a alone again did not kill tumor cells. Similar to the effects seen on A431 cells, increased KJD cell death was maximal when Dyngo4a was added only for the last hour of the 4 hour ADCC assay. Immunofluorescence analysis (FIG. 29) clearly shows that Dyngo4a has an inhibitory effect on the ligand-induced EGFR endocytosis.

Example 5

Figure 30A:
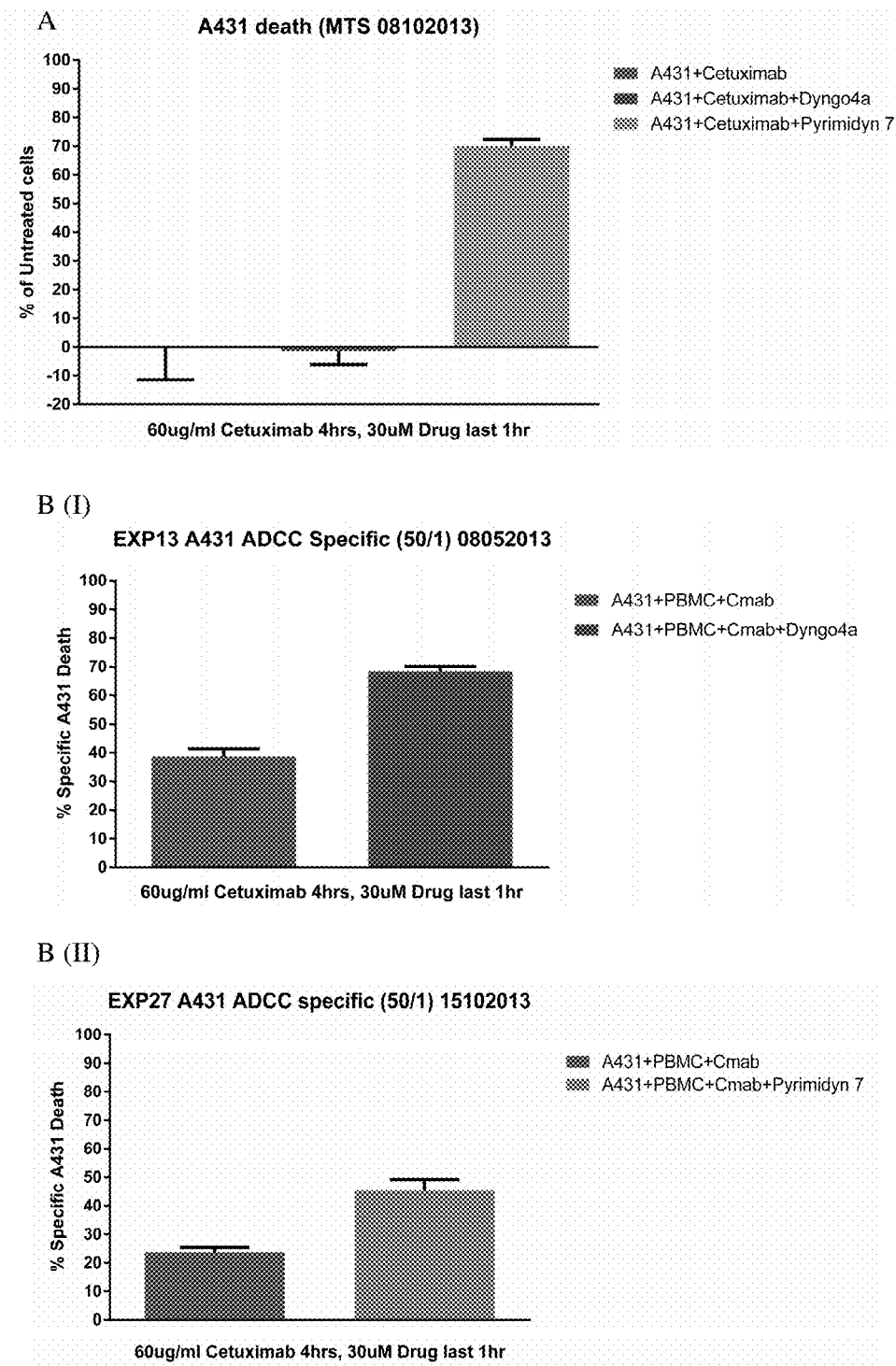
Figure 30B:
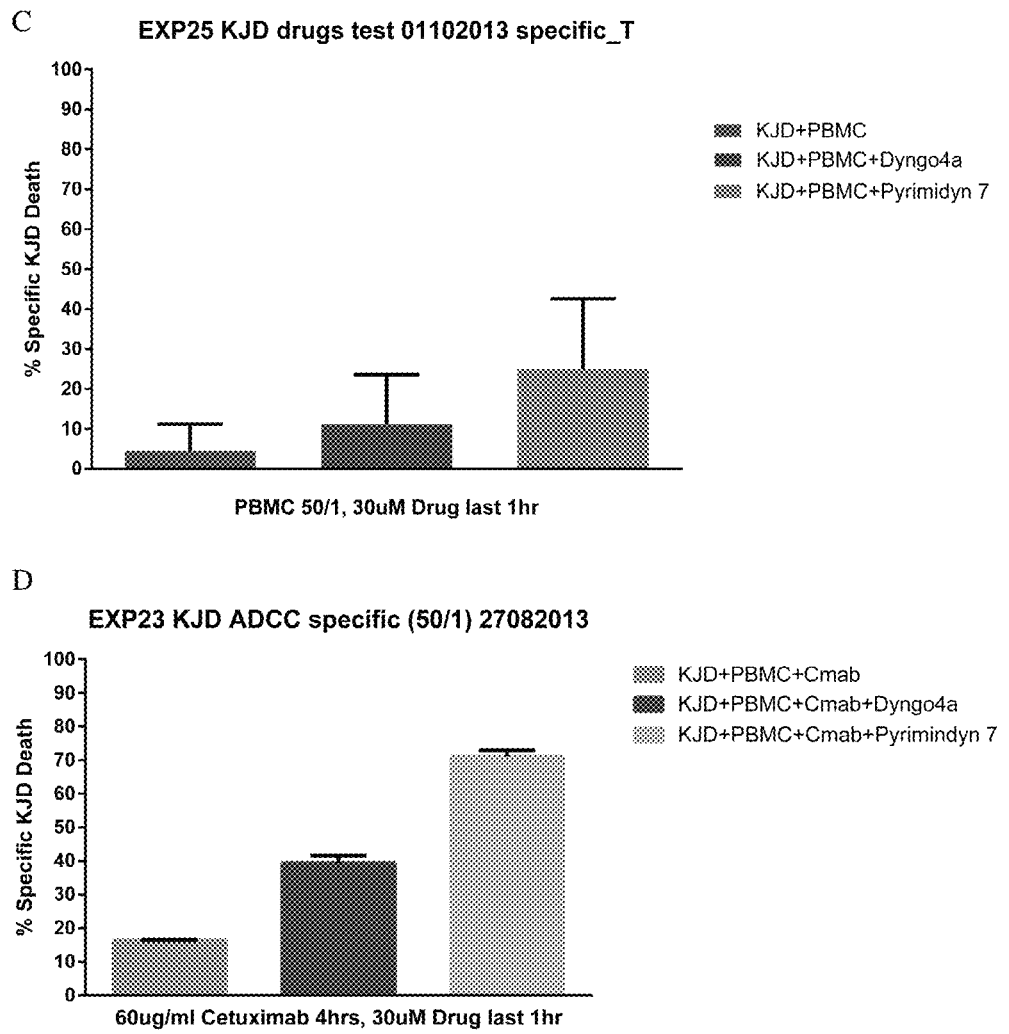
Figure 30C:
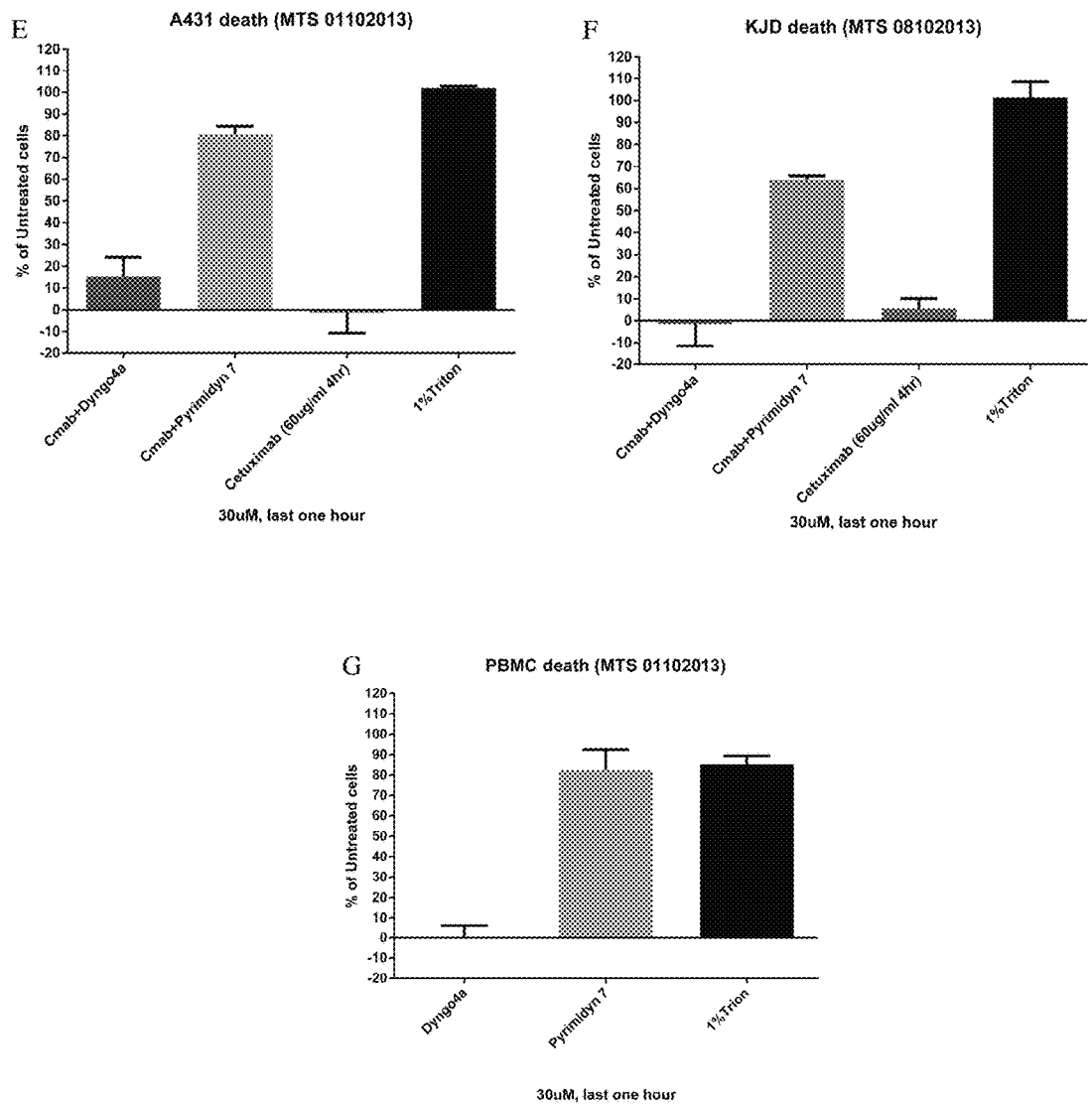

Dynamin Inhibitors, Dyngo4a and Pyrimidyn-7, Enhance Efficacy of Anti-EGFR Monoclonal Antibody Therapy on Cetuximab-Sensitive and Cetuximab-Resistant Cells Compounds Dyngo4a and Pyrimidyn-7 were tested in both multi-variant FACS analysis assay as described in Example 4 and by MTT assay. In particular, compounds were tested for improvement of cetuximab-dependent ADCC against cetuximab-sensitive A431 cells and cetuximab-resistant KJD cells and for single agent toxicity. By multi-variant FACs analysis both Dyngo4a and Pyrimidyn-7 were found to improve cetuximab-dependent ADCC (FIG. 30A-D). For Dyngo4a, all improvement in ADCC was dependent on the presence of cetuximab and PBMC (FIG. 30B). Some increase in cell death was observed by ADCC in the absence of cetuximab when Pyrimidyn-7 was introduced (FIG. 30C). MTT assays showed that Dyngo4a has no toxicity as a single agent when added to either PBMC, KJD or A431 cells (FIG. 30E-F). Pyrimidyn-7 showed single agent toxicity to both tumor cell lines and the PBMC (FIG. 30E-F). Thus, both dynamin inhibitors are able to improve cetuximab-mediated ADCC, although Dyngo4a showed the least single compound toxicity in these experiments.

Example 6

Dynamin Inhibitors Enhance Efficacy of Anti-Herceptin Monoclonal Antibody Therapy on Herceptin-Sensitive and -Resistant Cells Dyngo4a was tested in a multi-variant FACS analysis assay as described in Examples 4 and 5 for improving cetuximab-dependent and Herceptin-dependent ADCC against A431 cells and KJD cells. Of note, Dyngo4a was found to enhance both cetuximab-dependent and Herceptin-dependent ADCC of A431 cells and KJD cells (FIG. 31A-B). As was the case with cetuximab-dependent ADCC, Dyngo4a was found to enhance Herceptin-dependent ADCC of KJD cells even more so than Herceptin-dependent ADCC of A431 cells, because KJD cells have less Her2 receptor on their surface than A431 cells and are consequently more resistant to Herceptin mediated ADCC than A431 cells.

Example 7

Analysis of EGFR Trafficking by Three Dimensional Structured Illumination (Super Resolution) Microscopy (3D-SIM)

Materials & Methods

Super-Resolution Microscopy

For three dimensional structured illumination microscopy (3D-SIM), images were captured on a Deltavision OMX V3 Imaging System (Applied Precision), EMCCD cameras (CascadeII 512×512 Photometrics) and using a 60×1.4-NA UPlanSApo oil-immersion objective (Olympus) with oil of a refractive index of 1.524. Images were acquired with a Z-step 0.125 µm with 23-53 steps over thickness of 3-6.5 µm at a laser power of 10%. Images were computationally reconstructed using Deltavision SoftWorX6.0 Beta19 (Applied Precision).

Results

The present inventors also analyzed tumor samples by three dimensional structured illumination (super resolution) microscopy (3D-SIM) to more clearly show the EGFR trafficking differences within patient samples. FIG. 32A shows a patient whose EGFR does not undergo EGF-induced internalization and only plasma membrane localization can be observed while FIG. 32A also shows a normally internalizing EGFR patient, where the human cell endosomes can be clearly observed. Co-localization of EGFR with clathrin (FIG. 32B) demonstrated that in patient samples which failed to internalize EGFR, clathrin recruitment to the membrane was decreased in response to EGFR ligand stimulation and appeared to have increased distribution to the Trans-Golgi Network.

Summary

In summary, the present inventors describe herein a novel imaging assay to monitor EGF-induced EGFR internalization in living human tumor samples. They show that human SCCs can be categorized as either EGFR trafficking-competent or EGFR trafficking-incompetent. In addition, they show that EGFR trafficking status can contribute to EGFR plasma membrane expression levels, which in turn is predictive of cetuximab-induced ADCC of the target SCC cells. Moreover, the present inventors show that endocytosis inhibitors such as inhibitors of dynamin (including reversible inhibitors of dynamin such as Dyngo4a) can be used to increase specific tumor cell killing in cetuximab-sensitive SCC cells and importantly can convert an SCC cell which is insensitive to cetuximab-induced ADCC to a cell that is sensitive to cetuximab-induced SCC. Based on these findings it is predicted predict that patients whose EGFR receptor is trapped on the plasma membrane will respond best to monoclonal antibody therapy. The present inventors also propose that concurrent administration of endocytosis inhibitors with cetuximab in patients could act to enhance EGFR plasma membrane expression and cetuximab sensitivity. The present inventors propose that this principal will apply to other antibody therapies such as anti-VEGFR, anti-FGFR, anti-CD20 and anti-Her2/neu (e.g., Herceptin), antibody therapies, as evidenced for instance in Example 6.

The disclosure of every patent, patent application, and publication cited herein is hereby incorporated herein by reference in its entirety.

The citation of any reference herein should not be construed as an admission that such reference is available as "Prior Art" to the instant application.

Throughout the specification the aim has been to describe the preferred embodiments of the invention without limiting the invention to any one embodiment or specific collection of features. Those of skill in the art will therefore appreciate that, in light of the instant disclosure, various modifications and changes can be made in the particular embodiments exemplified without departing from the scope of the present invention. All such modifications and changes are intended to be included within the scope of the appended claims.

BIBLIOGRAPHY

1. Bonner J A, et al. (2006) Radiotherapy plus cetuximab for squamous-cell carcinoma of the head and neck. *New Engl J Med* 354(6):567-578.
2. Montagut C, et al. (2012) Identification of a mutation in the extracellular domain of the Epidermal Growth Factor Receptor conferring cetuximab resistance in colorectal cancer. *Nat Med* 18(2):221-223.
3. Ang M K & Hayes D N (2010) Imaging: Mass spectrometry in HNSCC—a peek at response prediction? *Nat Rev Clin Oncol* 7(4):193-195.
4. Gumuskaya B, et al. (2010) EGFR expression and gene copy number in triple-negative breast carcinoma. *Cancer Genet Cytogenet* 203(2):222-229.
5. Saridaki Z, Georgoulias V, & Souglakos J (2010) Mechanisms of resistance to anti-EGFR monoclonal antibody treatment in metastatic colorectal cancer. *World J Gastroenterol* 16(10):1177-1187.
6. Martinelli E, De Palma R, Orditura M, De Vita F, & Ciardiello F (2009) Anti-epidermal growth factor receptor monoclonal antibodies in cancer therapy. *Clin Exp Immunol* 158(1):1-9.
7. Siena S, Sartore-Bianchi A, Di. Nicolantonio F, Balfour J, & Bardelli A (2009) Biomarkers predicting clinical outcome of epideimal growth factor receptor-targeted therapy in metastatic colorectal cancer. *J Natl Cancer Inst* 101(19):1308-1324.
8. Moroni M, et al. (2005) Somatic mutation of EGFR catalytic domain and treatment with gefitinib in colorectal cancer. *Ann Oncol* 16(11):1848-1849.
9. Moroni M. et al. (2005) Gene copy number for epidermal growth factor receptor (EGFR) and clinical response to antiEGFR treatment in colorectal cancer: a cohort study. *Lancet Oncol* 6(5):279-286.
10. Lievre A, et al. (2006) KRAS mutation status is predictive of response to cetuximab therapy in colorectal cancer. *Cancer Res* 66(8):3992-3995.
11. Di Nicolantonio F, et al. (2008) Wild-type BRAF is required for response to panitumumab or cetuximab in metastatic colorectal cancer. *J Clin Oncol* 26(35):5705-5712.
12. Vieira A V, Lamaze C, & Schmid S L (1996) Control of EGF receptor signaling by clathrin-mediated endocytosis. *Science* 274(5295):2086-2089.
13. Rudnick S I, et al. (2011) Influence of affinity and antigen internalization on the uptake and penetration of Anti-HER2 antibodies in solid tumors. *Cancer Research* 71(6):2250-2259.
14. Cameron S R, et al. (2010) Tumor-initiating activity and tumor morphology of HNSCC is modulated by interactions between clonal variants within the tumor. *Lab Invest* 90(11):1594-1603.
15. Sigismund S, et al. (2008) Clathrin-mediated internalization is essential for sustained EGFR signaling but dispensable for degradation. *Dev Cell* 15(2):209-219.
16. Matsuo T, et al. (2011) Analysis of the anti-tumor effect of cetuximab using protein kinetics and mouse xenograft models. *BMC Res Notes* 4(1):140.
17. Abella J V & Park M (2009) Breakdown of endocytosis in the oncogenic activation of receptor tyrosine kinases. *Am J Physiol Endocrinol Metab* 296(5):E973-984.
18. Joffre C, et al. (2011) A direct role for Met endocytosis in tumorigenesis. *Nat Cell Biol*.
19. Franovic A, Holterman C E, Payette J, & Lee S (2009) Human cancers converge at the HIF-2alpha oncogenic axis. *Proceedings of the National Academy of Sciences of the United States of America* 106(50):21306-21311.
20. Spangler J B, et al. (2010) Combination antibody treatment down-regulates epidermal growth factor receptor by inhibiting endosomal recycling. *Proc Natl Acad Sci USA* 107(30):13252-13257.
21. Goldstein, N I., et al. (1995) Biological efficacy of a chimeric antibody to the epidermal growth factor receptor in a human tumor xenograft model. Clinical cancer research: an official journal of the American Association for Cancer Research 1: 1311-1318.
22. Schlaeth et al. (2010) Fc-engineered EGF-R antibodies mediate improved antibody-dependent cellular cytotoxicity (ADCC) against KRAS-mutated tumor cells. *Cancer Sci* 101: 1080-1088.
23. Kirchhausen et al. (2008) Use of dynasore, the small molecule inhibitor of dynamin, in the regulation of endocytosis. *Methods Enzymol* 438: 77-93.
24. Douthitt et al. (2011) Dynasore, an inhibitor of dynamin, increases the probability of transmitter release. *Neuroscience* 172: 187-195.
25. Tsai et al. (2009) Dynasore inhibits rapid endocytosis in bovine chromaffin cells. *Am J Physiol Cell Physiol* 297: C397-406.
26. Macia et al. (2006) Dynasore, a cell-permeable inhibitor of dynamin. *Dev Cell* 10: 839-850.
27. Kimura et al. (2007) Antibody-dependent cellular cytotoxicity of cetuximab against tumor cells with wild-type or mutant epidermal growth factor receptor. *Cancer Sci* 98: 1275-1280.

What is claimed is:

1. A composition comprising, consisting or consisting essentially of an antibody that binds to a cell surface antigen of a tumor, which antigen is subject to receptor-mediated endocytosis, and an inhibitor of receptor-mediated endocytosis, wherein the inhibitor of receptor-mediated endocytosis is a dynamin-dependent endocytosis inhibitor that (i) acts by inhibiting a GTPase domain of dynamin or (ii) is a hydrophobic amine; with the proviso that when the dynamin-dependent endocytosis inhibitor is a hydrophobic amine, the antibody does not bind CD20, Her2/neu or CD33.

2. A composition according to claim 1, wherein the dynamin-dependent endocytosis inhibitor is selected from the group consisting of dynamin GTPase activity inhibitors and dynamin ring stabilizers.

3. A composition according to claim 1, wherein the cell surface antigen is a tumor-associated antigen.

4. A composition according to claim 3, wherein the tumor-associated antigen is Epidermal Growth Factor Receptor (EGFR).

5. The composition of claim 1, wherein the dynamin-dependent endocytosis inhibitor in (ii) is a phenothiazine inhibitor.

6. The composition of claim 5, wherein the dynamin-dependent endocytosis inhibitor in (ii) is prochlorperazine.

7. A kit comprising an antibody that binds to a cell surface antigen of a tumor, which antigen is subject to receptor-mediated endocytosis, and an inhibitor of receptor-mediated endocytosis, wherein the inhibitor of receptor-mediated endocytosis is a dynamin-dependent endocytosis inhibitor that (i) acts by Inhibiting a GTPase domain of dynamin or (ii) is a hydrophobic amine; with the proviso that when the dynamin-dependent endocytosis inhibitor is a hydrophobic amine, the antibody does not bind CD20, Her2/neu, or CD33.

8. The kit according to claim 7, further comprising instructions for use in a method for enhancing an immune response to a tumor in a subject, the method comprising, consisting or consisting essentially of administering concurrently to the subject an effective amount of an inhibitor of receptor-mediated endocytosis, wherein the inhibitor of receptor-mediated endocytosis is a dynamin-dependent endocytosis inhibitor that (i) acts by inhibiting a GTPase domain of dynamin or (ii) is a hydrophobic amine, and an effective amount of an antibody that binds to a cell surface antigen of the tumor, which antigen is subject to receptor-mediated endocytosis; with the proviso that when the dynamin-dependent endocytosis inhibitor is a hydrophobic amine, the antibody does not bind CD20, Her2/neu, or CD33.

9. A method for enhancing an immune response to a tumor in a subject, the method comprising administering concurrently to the subject an effective amount of an inhibitor of receptor-mediated endocytosis, wherein the inhibitor of receptor-mediated endocytosis is a dynamin-dependent endocytosis inhibitor that (i) acts by inhibiting a GTPase domain of dynamin or (ii) is a hydrophobic amine, and an effective amount of an antibody that binds to a cell surface antigen of the tumor, which antigen is subject to receptor-mediated endocytosis; with the proviso that when the dynamin-dependent endocytosis inhibitor is a hydrophobic amine, the antibody does not bind CD20, Her2/neu or CD33.

10. A method according to claim 9, wherein the enhanced immune response comprises an enhanced antibody-dependent cellular cytotoxicity response.

11. A method according to claim 9, wherein the enhanced immune response comprises stimulating or enhancing the expression of MHC class II on the surface of cells of the tumor.

12. A method according to claim 9, further comprising classifying the tumor into a subtype selected from the group consisting of an antibody sensitive subtype and an antibody resistant subtype, and co-administering the inhibitor of receptor-mediated endocytosis and the antibody on the basis that the tumor is classified as an antibody resistant subtype.

13. A method according to claim 12, wherein the classification is carried out by a method comprising analyzing the ligand-induced cell surface antigen internalization status of the tumor, wherein an impaired or abrogated ligand-induced cell surface antigen internalization status indicates that the tumor is an antibody sensitive subtype and wherein an unimpaired ligand-induced cell surface antigen internalization of status indicates that the tumor is an antibody resistant subtype.

14. A method according to claim 12, wherein the classification is carried out by a method comprising analyzing the ligand-induced cell surface antigen internalization status of the tumor, wherein an impaired or abrogated ligand-induced cell surface antigen internalization status indicates that the tumor is an antibody sensitive subtype and wherein an unimpaired ligand-induced cell surface antigen internalization of status indicates that the tumor is an antibody resistant subtype, wherein an impaired or abrogated ligand-induced cell surface antigen internalization is indicated when, after at least 10 minutes in the presence of a ligand of the cell surface antigen, at least 90% of the cell surface antigen in cells of the tumor is localized or remains localized to the plasma membrane of the cells.

15. A method according to claim 12, wherein the classification is carried out by a method comprising analyzing the ligand-induced cell surface antigen internalization status of the tumor, wherein an impaired or abrogated ligand-induced cell surface antigen internalization status indicates that the tumor is an antibody sensitive subtype and wherein an unimpaired ligand-induced cell surface antigen internalization of status indicates that the tumor is an antibody resistant subtype, wherein an unimpaired ligand-induced cell surface antigen internalization is indicated when, after at least 10 minutes in the presence of a ligand to the cell surface antigen, less than 90% of the cell surface antigen in cell surface antigen-expressing cells of the tumor is localized or remains localized to the plasma membrane of the cells.

16. A method according to claim 9, wherein the tumor is a cell surface antigen positive tumor.

17. A method according to claim 9, wherein the tumor is selected from the group consisting of pre-cancerous, non-metastatic, metastatic, and cancerous tumors.

18. A method according to claim 9, wherein the tumor is associated with a cancer selected from the group consisting of carcinoma, lymphoma, blastoma, sarcoma, neuroendocrine tumors, mesothelioma, schwannoma, meningioma, adenocarcinoma, melanoma, leukemia, and lymphoid malignancies.

19. A method according to claim 18, wherein the cancer is selected from the group consisting of lung cancer, hepatocellular cancer, gastric or stomach cancer, pancreatic cancer, glioblastoma, cervical cancer, ovarian cancer, liver cancer, bladder cancer, hepatoma, breast cancer, colon cancer, rectal cancer, colorectal cancer, endometrial and uterine carcinoma, salivary gland carcinoma, kidney cancer, prostate cancer, vulval cancer, thyroid cancer, hepatic carcinoma, anal carcinoma, penile carcinoma, testicular cancer, esophageal cancer, tumors of the biliary tract, and head and neck cancer.

20. A method according to claim 18, wherein the cancer is squamous cell carcinoma (SCC).

21. A method according to claim 9, further comprising stratifying the subject into a treatment subgroup selected from the group consisting of responder to the antibody and non-responder to the antibody, and co-administering the inhibitor of receptor-mediated endocytosis and the antibody on the basis that the subject is stratified as a non-responder.

22. A method according to claim 9, further comprising stratifying the subject into a treatment subgroup selected from the group consisting of responder to the antibody and non-responder to the antibody, and co-administering the inhibitor of receptor-mediated endocytosis and the antibody on the basis that the subject is stratified as a non-responder, wherein the stratification is carried out by a method comprising classifying the tumor by a method comprising analyzing the ligand-induced cell surface antigen internalization status of the tumor, wherein an impaired or abrogated ligand-induced cell surface antigen internalization status indicates that the tumor is an antibody sensitive subtype and wherein an unimpaired ligand-induced cell surface antigen internalization of status indicates that the tumor is an antibody resistant subtype, and identifying the subject as a responder to the antibody if the tumor of the subject is analyzed as having an impaired or abrogated ligand-induced cell surface antigen internalization status or identifying the subject as a non-responder to the antibody if the tumor of the subject is analyzed as having an unimpaired ligand-induced cell surface antigen internalization status.

23. A method according to claim 22, further comprising obtaining a tumor sample from the subject for the analysis.

24. A method according to claim 22, further comprising administering an ancillary cancer therapy to the subject.

25. A method according to claim 22, further comprising administering an ancillary cancer therapy to the subject, wherein the ancillary therapy is selected from the group consisting of radiotherapy, surgery, chemotherapy, hormone ablation therapy, pro-apoptosis therapy, and immunotherapy other than the antibody.

26. A method according to claim 12, wherein the classifying of the tumor is performed by a processing system.

27. A method for treating a cancer in a subject, the method comprising concurrently administering to the subject an inhibitor of receptor-mediated endocytosis, wherein the inhibitor of receptor-mediated endocytosis is a dynamin-dependent endocytosis inhibitor that (i) acts by inhibiting a GTPase domain of dynamin or (ii) is a hydrophobic amine, and an antibody that binds to a cell surface antigen of a tumor associated with the cancer, which antigen is subject to receptor-mediated endocytosis, wherein the dynamin-dependent endocytosis inhibitor and the antigen are in amounts effective for treatment or prevention of the cancer; with the proviso that when the dynamin-dependent endocytosis inhibitor is a hydrophobic amine, the antibody does not bind CD20, Her2/neu or CD33.

28. A method for enhancing the efficacy of an antibody that binds to a cell surface antigen of a tumor in a subject, which antigen is subject to receptor-mediated endocytosis, the method comprising administering to the subject an inhibitor of receptor-mediated endocytosis, wherein the inhibitor of receptor-mediated endocytosis is a dynamin-dependent endocytosis inhibitor that (i) acts by inhibiting a GTPase domain of dynamin or (ii) is a hydrophobic amine, in an effective amount to enhance the efficacy of the antibody; with the proviso that when the dynamin-dependent endocytosis inhibitor is a hydrophobic amine, the antibody does not bind CD20, Her2/neu or CD33.

* * * * *